United States Patent [19]

Nohr et al.

[11] Patent Number: 6,127,073

[45] Date of Patent: Oct. 3, 2000

[54] METHOD FOR CONCEALING INFORMATION AND DOCUMENT FOR SECURELY COMMUNICATING CONCEALED INFORMATION

[75] Inventors: Ronald Sinclair Nohr, Alpharetta; John Gavin MacDonald, Decatur, both of Ga.; Jeffrey Dean Lindsay, Appleton, Wis.

[73] Assignee: Kimberly-Clark Worldwide, Inc., Neenah, Wis.

[21] Appl. No.: 09/204,875

[22] Filed: Dec. 3, 1998

Related U.S. Application Data

[62] Division of application No. 08/946,953, Oct. 8, 1997, and a continuation of application No. 08/462,105, Jun. 5, 1995, abandoned, and a continuation-in-part of application No. 08/336,813, Nov. 9, 1994, abandoned, application No. 08/403,240, Mar. 10, 1995, abandoned, application No. 08/373,958, Jan. 17, 1995, abandoned, application No. 08/360,501, Dec. 21, 1994, Pat. No. 5,865,471, and application No. 08/359,670, Dec. 20, 1994, abandoned, said application No. 08/360,501, is a continuation-in-part of application No. 08/258,858, Jun. 13, 1994, abandoned, said application No. 08/359,670, Dec. 20, 1994, abandoned, is a continuation-in-part of application No. 08/258,858, which is a continuation-in-part of application No. 08/119,912, Sep. 10, 1993, abandoned, and application No. 08/103,503, Aug. 5, 1993, abandoned.

[51] Int. Cl.[7] ..................................................... B42D 15/00
[52] U.S. Cl. .............................. 430/19; 430/339; 283/85; 283/901; 283/903; 427/145; 427/553; 427/160
[58] Field of Search ........................ 430/19, 339; 283/85, 283/901, 903; 427/145, 553, 160

[56] References Cited

U.S. PATENT DOCUMENTS

| | | |
|---|---|---|
| Re. 28,225 | 11/1974 | Heseltine et al. . |
| Re. 28,789 | 4/1976 | Chang . |
| 575,228 | 1/1897 | von Gallois . |

(List continued on next page.)

FOREIGN PATENT DOCUMENTS

| | | |
|---|---|---|
| 103085 | 4/1937 | Australia . |
| 12624/88 | 9/1988 | Australia . |
| 620075 | 5/1962 | Belgium . |
| 637169 | 3/1964 | Belgium . |
| 413257 | 10/1932 | Canada . |
| 458808 | 12/1936 | Canada . |
| 460268 | 10/1949 | Canada . |
| 461082 | 11/1949 | Canada . |
| 463021 | 2/1950 | Canada . |
| 463022 | 2/1950 | Canada . |
| 465495 | 5/1950 | Canada . |
| 465496 | 5/1950 | Canada . |
| 465499 | 5/1950 | Canada . |
| 483214 | 5/1952 | Canada . |
| 517364 | 10/1955 | Canada . |

(List continued on next page.)

OTHER PUBLICATIONS

Kubat et al. "Photophysical properties of metal complexes of meso–tetrakis (40sulphonatophenyl) porphyrin," *J. Photochem. and Photobiol.* 96 93–97 1996.

(List continued on next page.)

*Primary Examiner*—John A. McPherson
*Attorney, Agent, or Firm*—Jones & Askew, LLP

[57] ABSTRACT

Applications of photoerasable colorant composition include photoerasable price markings for pricing goods, documents such as gaming tickets for securely communicating concealed information, photoerasable paint for temporary markings on terrain and structures such as signs, roadways, trees, and buildings, marking instruments such as pens, and wick or felt markers, ultraviolet light exposure indicators, and dry printing. The photoerasable or mutable colorant composition comprises a mutable colorant and an ultraviolet radiation transorber which, upon irradiation with ultraviolet radiation, interacts with the colorant to irreversibly mutate the colorant and thereby render the colorant substantially colorless. The mutable colorant composition may also include a molecular includant.

20 Claims, 8 Drawing Sheets

U.S. PATENT DOCUMENTS

| | | |
|---|---|---|
| 582,853 | 5/1897 | Feer . |
| 893,636 | 7/1908 | Maywald . |
| 1,013,544 | 1/1912 | Fuerth . |
| 1,325,971 | 2/1919 | Akashi . |
| 1,364,406 | 1/1921 | Olsen . |
| 1,436,856 | 11/1922 | Brenizer et al. . |
| 1,744,149 | 1/1930 | Staehlin . |
| 1,803,906 | 5/1931 | Krieger et al. . |
| 1,844,199 | 2/1932 | Bicknell et al. . |
| 1,876,880 | 9/1932 | Drapal . |
| 1,880,572 | 10/1932 | Wendt et al. . |
| 1,880,573 | 10/1932 | Wendt et al. . |
| 1,916,350 | 7/1933 | Wendt et al. . |
| 1,916,779 | 7/1933 | Wendt et al. . |
| 1,955,898 | 4/1934 | Wendt et al. . |
| 1,962,111 | 6/1934 | Bamberger . |
| 2,005,378 | 6/1935 | Kiel . |
| 2,005,511 | 6/1935 | Stoll et al. . |
| 2,049,005 | 7/1936 | Gaspar . |
| 2,054,390 | 9/1936 | Rust et al. . |
| 2,058,489 | 10/1936 | Murch et al. . |
| 2,062,304 | 12/1936 | Gaspar . |
| 2,090,511 | 9/1937 | Crossley et al. . |
| 2,097,119 | 10/1937 | Eggert . |
| 2,106,539 | 1/1938 | Schnitzspahn . |
| 2,111,692 | 3/1938 | Saunders et al. . |
| 2,125,015 | 7/1938 | Gaspar . |
| 2,130,572 | 9/1938 | Wendt . |
| 2,132,154 | 10/1938 | Gaspar . |
| 2,145,960 | 2/1939 | Wheatley et al. . |
| 2,154,996 | 4/1939 | Rawling . |
| 2,159,280 | 5/1939 | Mannes et al. . |
| 2,171,976 | 9/1939 | Erickson . |
| 2,181,800 | 11/1939 | Crossley et al. . |
| 2,185,153 | 12/1939 | Lecher et al. . |
| 2,220,178 | 11/1940 | Schneider . |
| 2,230,590 | 2/1941 | Eggert et al. . |
| 2,237,885 | 4/1941 | Markush et al. . |
| 2,243,630 | 5/1941 | Houk et al. . |
| 2,268,324 | 12/1941 | Polgar . |
| 2,281,895 | 5/1942 | van Poser et al. . |
| 2,328,166 | 8/1943 | Poigar et al. . |
| 2,346,090 | 4/1944 | Staehle . |
| 2,349,090 | 5/1944 | Haddock . |
| 2,356,618 | 8/1944 | Rossander et al. . |
| 2,361,301 | 10/1944 | Libby, Jr. et al. . |
| 2,364,359 | 12/1944 | Kienle et al. . |
| 2,381,145 | 8/1945 | von Glahn et al. . |
| 2,382,904 | 8/1945 | Federsen . |
| 2,386,646 | 10/1945 | Adams et al. . |
| 2,402,106 | 6/1946 | von Glahn et al. . |
| 2,416,145 | 2/1947 | Biro . |
| 2,477,165 | 7/1949 | Bergstrom . |
| 2,527,347 | 10/1950 | Bergstrom . |
| 2,580,461 | 1/1952 | Pearl . |
| 2,601,669 | 6/1952 | Tullsen . |
| 2,612,494 | 9/1952 | von Glahn et al. . |
| 2,612,495 | 9/1952 | von Glahn et al. . |
| 2,628,959 | 2/1953 | von Glahn et al. . |
| 2,647,080 | 7/1953 | Joyce . |
| 2,680,685 | 6/1954 | Ratchford . |
| 2,728,784 | 12/1955 | Tholstrup et al. . |
| 2,732,301 | 1/1956 | Robertson et al. . |
| 2,744,103 | 5/1956 | Koch . |
| 2,757,090 | 7/1956 | Meugebauer et al. . |
| 2,763,550 | 9/1956 | Lovick . |
| 2,768,171 | 10/1956 | Clarke et al. . |
| 2,773,056 | 12/1956 | Helfaer . |
| 2,798,000 | 7/1957 | Monterman . |
| 2,809,189 | 10/1957 | Stanley et al. . |
| 2,827,358 | 3/1958 | Kaplan et al. . |
| 2,834,773 | 5/1958 | Scalera et al. . |
| 2,875,045 | 2/1959 | Lurie . |
| 2,892,865 | 6/1959 | Giraldi et al. . |
| 2,897,187 | 7/1959 | Koch . |
| 2,936,241 | 5/1960 | Sharp et al. . |
| 2,940,853 | 6/1960 | Sagura et al. . |
| 2,955,067 | 10/1960 | McBurney et al. . |
| 2,992,129 | 7/1961 | Gauthier . |
| 2,992,198 | 7/1961 | Funahashi . |
| 3,030,208 | 4/1962 | Schellenberg et al. . |
| 3,071,815 | 1/1963 | MacKinnon . |
| 3,075,014 | 1/1963 | Palopoli et al. . |
| 3,076,813 | 2/1963 | Sharp . |
| 3,104,973 | 9/1963 | Sprague et al. . |
| 3,114,634 | 12/1963 | Brown et al. . |
| 3,121,632 | 2/1964 | Sprague et al. . |
| 3,123,647 | 3/1964 | Duennenberger et al. . |
| 3,133,049 | 5/1964 | Hertel et al. . |
| 3,140,949 | 7/1964 | Sprague et al. . |
| 3,154,416 | 10/1964 | Fidelman . |
| 3,155,509 | 11/1964 | Roscow . |
| 3,175,905 | 3/1965 | Wiesbaden . |
| 3,178,285 | 4/1965 | Anderau et al. . |
| 3,238,163 | 3/1966 | O'Neill . |
| 3,242,215 | 3/1966 | Heitmiller . |
| 3,248,337 | 4/1966 | Zirker et al. . |
| 3,266,973 | 8/1966 | Crowley . |
| 3,282,886 | 11/1966 | Gadecki . |
| 3,284,205 | 11/1966 | Sprague et al. . |
| 3,300,314 | 1/1967 | Rauner et al. . |
| 3,304,297 | 2/1967 | Wegmann et al. . |
| 3,305,361 | 2/1967 | Gaynor et al. . |
| 3,313,797 | 4/1967 | Kissa . |
| 3,320,080 | 5/1967 | Mazzarella et al. . |
| 3,330,659 | 7/1967 | Wainer . |
| 3,341,492 | 9/1967 | Champ et al. . |
| 3,359,109 | 12/1967 | Harder et al. . |
| 3,361,827 | 1/1968 | Biletch . |
| 3,363,969 | 1/1968 | Brooks . |
| 3,385,700 | 5/1968 | Willems et al. . |
| 3,397,984 | 8/1968 | Williams et al. . |
| 3,415,875 | 12/1968 | Luethi et al. . |
| 3,418,118 | 12/1968 | Thommes et al. . |
| 3,445,234 | 5/1969 | Cescon et al. . |
| 3,453,258 | 7/1969 | Parmerter et al. . |
| 3,453,259 | 7/1969 | Parmerter et al. . |
| 3,464,841 | 9/1969 | Skofronick . |
| 3,467,647 | 9/1969 | Benninga . |
| 3,479,185 | 11/1969 | Chambers . |
| 3,502,476 | 3/1970 | Kohei et al. . |
| 3,503,744 | 3/1970 | Itano et al. . |
| 3,514,597 | 5/1970 | Haes et al. . |
| 3,541,142 | 11/1970 | Cragoe, Jr. . |
| 3,546,161 | 12/1970 | Wolheim . |
| 3,547,646 | 12/1970 | Hori et al. . |
| 3,549,367 | 12/1970 | Chang et al. . |
| 3,553,710 | 1/1971 | Lloyd et al. . |
| 3,563,931 | 2/1971 | Horiguchi . |
| 3,565,753 | 2/1971 | Yurkowitz . |
| 3,574,624 | 4/1971 | Reynolds et al. . |
| 3,579,533 | 5/1971 | Yalman . |
| 3,595,655 | 7/1971 | Robinson et al. . |
| 3,595,657 | 7/1971 | Robinson et al. . |
| 3,595,658 | 7/1971 | Gerlach et al. . |
| 3,595,659 | 7/1971 | Gerlach et al. . |
| 3,607,639 | 9/1971 | Krefeld et al. . |
| 3,607,693 | 9/1971 | Heine et al. . |
| 3,607,863 | 9/1971 | Dosch . |
| 3,615,562 | 10/1971 | Harrison et al. . |
| 3,617,288 | 11/1971 | Hartman et al. . |
| 3,617,335 | 11/1971 | Kumura et al. . |

| | | | | | |
|---|---|---|---|---|---|
| 3,619,238 | 11/1971 | Kimura et al. . | 4,107,733 | 8/1978 | Schickedanz . |
| 3,619,239 | 11/1971 | Osada et al. . | 4,110,112 | 8/1978 | Roman et al. . |
| 3,637,337 | 1/1972 | Pilling . | 4,111,699 | 9/1978 | Krueger . |
| 3,637,581 | 1/1972 | Horioguchi et al. . | 4,114,028 | 9/1978 | Baio et al. . |
| 3,642,472 | 2/1972 | Mayo . | 4,126,412 | 11/1978 | Masson et al. . |
| 3,647,467 | 3/1972 | Grubb . | 4,141,807 | 2/1979 | Via . |
| 3,652,275 | 3/1972 | Baum et al. . | 4,144,156 | 3/1979 | Kuesters et al. . |
| 3,660,542 | 5/1972 | Adachi et al. . | 4,148,658 | 4/1979 | Kondoh et al. . |
| 3,667,954 | 6/1972 | Itano et al. . | 4,162,162 | 7/1979 | Dueber . |
| 3,668,188 | 6/1972 | King et al. . | 4,171,977 | 10/1979 | Hasegawa et al. . |
| 3,669,925 | 6/1972 | King et al. . | 4,179,577 | 12/1979 | Green . |
| 3,671,096 | 6/1972 | Mackin . | 4,181,807 | 1/1980 | Green . |
| 3,671,251 | 6/1972 | Houle et al. . | 4,190,671 | 2/1980 | Vanstone et al. . |
| 3,676,690 | 7/1972 | McMillin et al. . | 4,197,080 | 4/1980 | Mee . |
| 3,678,044 | 7/1972 | Adams . | 4,199,420 | 4/1980 | Photis . |
| 3,689,565 | 9/1972 | Hoffmann et al. . | 4,229,172 | 10/1980 | Baumann et al. . |
| 3,694,241 | 9/1972 | Guthrie et al. . | 4,232,106 | 11/1980 | Iwasaki et al. . |
| 3,695,879 | 10/1972 | Laming et al. . | 4,238,492 | 12/1980 | Majoie . |
| 3,697,280 | 10/1972 | Strilko . | 4,239,843 | 12/1980 | Hara et al. . |
| 3,705,043 | 12/1972 | Zablak . | 4,239,850 | 12/1980 | Kita et al. . |
| 3,707,371 | 12/1972 | Files . | 4,241,155 | 12/1980 | Hara et al. . |
| 3,729,313 | 4/1973 | Smith . | 4,242,430 | 12/1980 | Hara et al. . |
| 3,737,628 | 6/1973 | Azure . | 4,242,431 | 12/1980 | Hara et al. . |
| 3,765,896 | 10/1973 | Fox . | 4,245,018 | 1/1981 | Hara et al. . |
| 3,775,130 | 11/1973 | Enomoto et al. . | 4,245,995 | 1/1981 | Hugl et al. . |
| 3,788,849 | 1/1974 | Taguchi et al. . | 4,246,330 | 1/1981 | Hara et al. . |
| 3,799,773 | 3/1974 | Watarai et al. . | 4,248,949 | 2/1981 | Hara et al. . |
| 3,800,439 | 4/1974 | Sokolski et al. . | 4,250,096 | 2/1981 | Kvita et al. . |
| 3,801,329 | 4/1974 | Sandner et al. . | 4,251,622 | 2/1981 | Kimoto et al. . |
| 3,817,752 | 6/1974 | Laridon et al. . | 4,251,662 | 2/1981 | Ozawa et al. . |
| 3,840,338 | 10/1974 | Zviak et al. . | 4,254,195 | 3/1981 | Hara et al. . |
| 3,844,790 | 10/1974 | Chang et al. . | 4,256,493 | 3/1981 | Yokoyama et al. . |
| 3,870,524 | 3/1975 | Watanabe et al. . | 4,256,817 | 3/1981 | Hara et al. . |
| 3,873,500 | 3/1975 | Kato et al. . | 4,258,123 | 3/1981 | Nagashima et al. . |
| 3,876,496 | 4/1975 | Lozano . | 4,258,367 | 3/1981 | Mansukhani . |
| 3,887,450 | 6/1975 | Gilano et al. . | 4,259,432 | 3/1981 | Kondoh et al. . |
| 3,895,949 | 7/1975 | Akamatsu . | 4,262,936 | 4/1981 | Miyamoto . |
| 3,901,779 | 8/1975 | Mani . | 4,268,605 | 5/1981 | Hara et al. . |
| 3,910,993 | 10/1975 | Avar et al. . | 4,268,667 | 5/1981 | Anderson . |
| 3,914,165 | 10/1975 | Gaske . | 4,269,926 | 5/1981 | Hara et al. . |
| 3,914,166 | 10/1975 | Rudolph et al. . | 4,270,130 | 5/1981 | Houle et al. . |
| 3,915,824 | 10/1975 | McGinniss . | 4,271,252 | 6/1981 | Hara et al. . |
| 3,919,323 | 11/1975 | Houlihan et al. . | 4,271,253 | 6/1981 | Hara et al. . |
| 3,926,641 | 12/1975 | Rosen . | 4,272,244 | 6/1981 | Schlick . |
| 3,928,264 | 12/1975 | Young, Jr. et al. . | 4,276,211 | 6/1981 | Singer et al. . |
| 3,933,682 | 1/1976 | Bean . | 4,277,497 | 7/1981 | Fromantin . |
| 3,952,129 | 4/1976 | Matsukawa et al. . | 4,279,653 | 7/1981 | Makishima et al. . |
| 3,960,685 | 6/1976 | Sano et al. . | 4,279,982 | 7/1981 | Iwasaki et al. . |
| 3,965,157 | 6/1976 | Harrison . | 4,279,985 | 7/1981 | Nonogaki et al. . |
| 3,978,132 | 8/1976 | Houlihan et al. . | 4,284,485 | 8/1981 | Berner . |
| 3,984,248 | 10/1976 | Sturmer . | 4,288,631 | 9/1981 | Ching . |
| 3,988,154 | 10/1976 | Sturmer . | 4,289,844 | 9/1981 | Specht et al. . |
| 4,004,998 | 1/1977 | Rosen . | 4,290,870 | 9/1981 | Kondoh et al. . |
| 4,012,256 | 3/1977 | Levinos . | 4,293,458 | 10/1981 | Gruenberger et al. . |
| 4,017,652 | 4/1977 | Gruber . | 4,298,679 | 11/1981 | Shinozaki et al. . |
| 4,022,674 | 5/1977 | Rosen . | 4,300,123 | 11/1981 | McMillin et al. . |
| 4,024,324 | 5/1977 | Sparks . | 4,301,223 | 11/1981 | Nakamura et al. . |
| 4,039,332 | 8/1977 | Kokelenberg et al. . | 4,302,606 | 11/1981 | Barabas et al. . |
| 4,043,819 | 8/1977 | Baumann . | 4,306,014 | 12/1981 | Kunikane et al. . |
| 4,048,034 | 9/1977 | Martan . | 4,307,182 | 12/1981 | Dalzell et al. . |
| 4,054,719 | 10/1977 | Cordes, III . | 4,308,400 | 12/1981 | Felder et al. . |
| 4,056,665 | 11/1977 | Tayler et al. . | 4,315,807 | 2/1982 | Felder et al. . |
| 4,058,400 | 11/1977 | Crivello . | 4,318,705 | 3/1982 | Nowak et al. . |
| 4,067,892 | 1/1978 | Thorne et al. . | 4,318,791 | 3/1982 | Felder et al. . |
| 4,071,424 | 1/1978 | Dart et al. . | 4,321,118 | 3/1982 | Felder et al. . |
| 4,073,968 | 2/1978 | Miyamoto et al. . | 4,335,054 | 6/1982 | Blaser et al. . |
| 4,077,769 | 3/1978 | Garcia . | 4,335,055 | 6/1982 | Blaser et al. . |
| 4,079,183 | 3/1978 | Green . | 4,336,323 | 6/1982 | Winslow . |
| 4,085,062 | 4/1978 | Virgilio et al. . | 4,343,891 | 8/1982 | Aasen et al. . |
| 4,090,877 | 5/1978 | Streeper . | 4,345,011 | 8/1982 | Drexhage . |
| 4,100,047 | 7/1978 | McCarty . | 4,347,111 | 8/1982 | Gehlhaus et al. . |
| 4,105,572 | 8/1978 | Gorondy . | 4,349,617 | 9/1982 | Kawashiri et al. . |

| | | |
|---|---|---|
| 4,350,753 | 9/1982 | Shelnut et al. . |
| 4,351,893 | 9/1982 | Anderson . |
| 4,356,255 | 10/1982 | Tachikawa et al. . |
| 4,357,468 | 11/1982 | Szejtli et al. . |
| 4,359,524 | 11/1982 | Masuda et al. . |
| 4,362,806 | 12/1982 | Whitmore . |
| 4,367,072 | 1/1983 | Vogtle et al. . |
| 4,367,280 | 1/1983 | Kondo et al. . |
| 4,369,283 | 1/1983 | Altschuler . |
| 4,370,401 | 1/1983 | Winslow et al. . |
| 4,372,582 | 2/1983 | Geisler . |
| 4,373,017 | 2/1983 | Masukawa et al. . |
| 4,373,020 | 2/1983 | Winslow . |
| 4,374,984 | 2/1983 | Eichler et al. . |
| 4,376,887 | 3/1983 | Greenaway et al. . |
| 4,383,835 | 5/1983 | Preuss et al. . |
| 4,390,616 | 6/1983 | Sato et al. . |
| 4,391,867 | 7/1983 | Derick et al. . |
| 4,399,209 | 8/1983 | Sanders et al. . |
| 4,400,173 | 8/1983 | Beavan . |
| 4,401,470 | 8/1983 | Bridger . |
| 4,416,961 | 11/1983 | Drexhage . |
| 4,421,559 | 12/1983 | Owatari . |
| 4,424,325 | 1/1984 | Tsunoda et al. . |
| 4,425,162 | 1/1984 | Sugiyama . |
| 4,425,424 | 1/1984 | Altland et al. . |
| 4,426,153 | 1/1984 | Libby et al. . |
| 4,434,035 | 2/1984 | Eichler et al. . |
| 4,440,827 | 4/1984 | Miyamoto et al. . |
| 4,447,521 | 5/1984 | Tiers et al. . |
| 4,450,227 | 5/1984 | Holmes et al. . |
| 4,460,676 | 7/1984 | Fabel . |
| 4,467,112 | 8/1984 | Matsuura et al. . |
| 4,475,999 | 10/1984 | Via . |
| 4,477,681 | 10/1984 | Gehlhaus et al. . |
| 4,489,334 | 12/1984 | Owatari . |
| 4,495,041 | 1/1985 | Goldstein . |
| 4,496,447 | 1/1985 | Eichler et al. . |
| 4,500,355 | 2/1985 | Shimada et al. . |
| 4,508,570 | 4/1985 | Fugii et al. . |
| 4,510,392 | 4/1985 | Litt et al. . |
| 4,523,924 | 6/1985 | Lacroix . |
| 4,524,122 | 6/1985 | Weber et al. . |
| 4,534,838 | 8/1985 | Lin et al. . |
| 4,548,896 | 10/1985 | Sabongi et al. . |
| 4,555,474 | 11/1985 | Kawamura . |
| 4,557,730 | 12/1985 | Bennett et al. . |
| 4,564,560 | 1/1986 | Tani et al. . |
| 4,565,769 | 1/1986 | Dueber et al. . |
| 4,567,171 | 1/1986 | Mangum . |
| 4,571,377 | 2/1986 | McGinniss et al. . |
| 4,595,745 | 6/1986 | Nakano et al. . |
| 4,604,344 | 8/1986 | Irving et al. . |
| 4,605,442 | 8/1986 | Kawashita et al. . |
| 4,613,334 | 9/1986 | Thomas et al. . |
| 4,614,723 | 9/1986 | Schmidt et al. . |
| 4,617,380 | 10/1986 | Hinson et al. . |
| 4,620,875 | 11/1986 | Shimada et al. . |
| 4,620,876 | 11/1986 | Fugii et al. . |
| 4,622,286 | 11/1986 | Sheets . |
| 4,631,085 | 12/1986 | Kawanishi et al. . |
| 4,632,891 | 12/1986 | Banks et al. . |
| 4,632,895 | 12/1986 | Patel et al. . |
| 4,634,644 | 1/1987 | Irving et al. . |
| 4,638,340 | 1/1987 | Iiyama et al. . |
| 4,647,310 | 3/1987 | Shimada et al. . |
| 4,655,783 | 4/1987 | Reinert et al. . |
| 4,663,275 | 5/1987 | West et al. . |
| 4,663,641 | 5/1987 | Iiyama et al. . |
| 4,668,533 | 5/1987 | Miller . |
| 4,672,041 | 6/1987 | Jain . |
| 4,698,291 | 10/1987 | Koibuchi et al. . |
| 4,701,402 | 10/1987 | Patel et al. . |
| 4,702,996 | 10/1987 | Griffing et al. . |
| 4,704,133 | 11/1987 | Reinert et al. . |
| 4,707,161 | 11/1987 | Thomas et al. . |
| 4,707,425 | 11/1987 | Sasagawa et al. . |
| 4,707,430 | 11/1987 | Ozawa et al. . |
| 4,711,668 | 12/1987 | Shimada et al. . |
| 4,713,113 | 12/1987 | Shimada et al. . |
| 4,720,450 | 1/1988 | Ellis . |
| 4,721,531 | 1/1988 | Wildeman et al. . |
| 4,721,734 | 1/1988 | Gehlhaus et al. . |
| 4,724,021 | 2/1988 | Martin et al. . |
| 4,724,201 | 2/1988 | Okazaki et al. . |
| 4,725,527 | 2/1988 | Robillard . |
| 4,727,824 | 3/1988 | Ducharme et al. . |
| 4,732,615 | 3/1988 | Kawashita et al. . |
| 4,737,190 | 4/1988 | Shimada et al. . |
| 4,737,438 | 4/1988 | Ito et al. . |
| 4,740,451 | 4/1988 | Kohara . |
| 4,745,042 | 5/1988 | Sasago et al. . |
| 4,746,735 | 5/1988 | Kruper, Jr. et al. . |
| 4,752,341 | 6/1988 | Rock . |
| 4,755,450 | 7/1988 | Sanders et al. . |
| 4,761,181 | 8/1988 | Suzuki . |
| 4,766,050 | 8/1988 | Jerry . |
| 4,766,055 | 8/1988 | Kawabata et al. . |
| 4,770,667 | 9/1988 | Evans et al. . |
| 4,771,802 | 12/1987 | Tannenbaum . |
| 4,772,291 | 9/1988 | Shibanai et al. . |
| 4,772,541 | 9/1988 | Gottschalk . |
| 4,775,386 | 10/1988 | Reinert et al. . |
| 4,786,586 | 11/1988 | Lee et al. . |
| 4,789,382 | 12/1988 | Neumann et al. . |
| 4,790,565 | 12/1988 | Steed . |
| 4,800,149 | 1/1989 | Gottschalk . |
| 4,803,008 | 2/1989 | Ciolino et al. . |
| 4,808,189 | 2/1989 | Oishi et al. . |
| 4,812,139 | 3/1989 | Brodmann . |
| 4,812,517 | 3/1989 | West . |
| 4,813,970 | 3/1989 | Kirjanov et al. . |
| 4,822,714 | 4/1989 | Sanders . |
| 4,829,187 | 5/1989 | Tomita et al. . |
| 4,831,068 | 5/1989 | Reinert et al. . |
| 4,834,771 | 5/1989 | Yamauchi et al. . |
| 4,837,106 | 6/1989 | Ishikawa et al. . |
| 4,837,331 | 6/1989 | Yamanishi et al. . |
| 4,838,938 | 6/1989 | Tomida et al. . |
| 4,839,269 | 6/1989 | Okazaki et al. . |
| 4,849,320 | 7/1989 | Irving et al. . |
| 4,853,037 | 8/1989 | Johnson et al. . |
| 4,853,398 | 8/1989 | Carr et al. . |
| 4,854,971 | 8/1989 | Gane et al. . |
| 4,857,438 | 8/1989 | Loerzer et al. . |
| 4,861,916 | 8/1989 | Kohler et al. . |
| 4,865,942 | 9/1989 | Gottschalk et al. . |
| 4,874,391 | 10/1989 | Reinert . |
| 4,874,899 | 10/1989 | Hoelderich et al. . |
| 4,885,395 | 12/1989 | Hoelderich . |
| 4,886,774 | 12/1989 | Doi . |
| 4,892,941 | 1/1990 | Dolphin et al. . |
| 4,895,880 | 1/1990 | Gottschalk . |
| 4,900,581 | 2/1990 | Stuke et al. . |
| 4,902,299 | 2/1990 | Anton . |
| 4,902,725 | 2/1990 | Moore . |
| 4,902,787 | 2/1990 | Freeman . |
| 4,911,732 | 3/1990 | Neumann et al. . |
| 4,911,899 | 3/1990 | Hagiwara et al. . |
| 4,917,956 | 4/1990 | Rohrbach . |
| 4,921,317 | 5/1990 | Suzuki et al. . |
| 4,925,770 | 5/1990 | Ichiura et al. . |
| 4,925,777 | 5/1990 | Inoue et al. . |
| 4,926,190 | 5/1990 | Lavar . |

| | | |
|---|---|---|
| 4,933,265 | 6/1990 | Inoue et al. . |
| 4,933,948 | 6/1990 | Herkstroeter . |
| 4,937,161 | 6/1990 | Kita et al. . |
| 4,942,113 | 7/1990 | Trundle . |
| 4,944,988 | 7/1990 | Yasuda et al. . |
| 4,950,304 | 8/1990 | Reinert et al. . |
| 4,952,478 | 8/1990 | Miyagawa et al. . |
| 4,952,680 | 8/1990 | Schmeidl . |
| 4,954,380 | 9/1990 | Kanome et al. . |
| 4,954,416 | 9/1990 | Wright et al. . |
| 4,956,254 | 9/1990 | Washizu et al. . |
| 4,964,871 | 10/1990 | Reinert et al. . |
| 4,965,294 | 10/1990 | Ohngemach et al. . |
| 4,966,607 | 10/1990 | Shinoki et al. . |
| 4,966,833 | 10/1990 | Inoue . |
| 4,968,596 | 11/1990 | Inoue et al. . |
| 4,968,813 | 11/1990 | Rule et al. . |
| 4,985,345 | 1/1991 | Hayakawa et al. . |
| 4,987,056 | 1/1991 | Imahashi et al. . |
| 4,988,561 | 1/1991 | Wason . |
| 4,997,745 | 3/1991 | Kawamura et al. . |
| 5,001,330 | 3/1991 | Koch . |
| 5,002,853 | 3/1991 | Aoai et al. . |
| 5,002,993 | 3/1991 | West et al. . |
| 5,003,142 | 3/1991 | Fuller . |
| 5,006,758 | 4/1991 | Gellert et al. . |
| 5,013,959 | 5/1991 | Kogelschatz . |
| 5,017,195 | 5/1991 | Satou et al. . |
| 5,023,129 | 6/1991 | Morganti et al. . |
| 5,025,036 | 6/1991 | Carson et al. . |
| 5,026,425 | 6/1991 | Hindagolla et al. . |
| 5,026,427 | 6/1991 | Mitchell et al. . |
| 5,028,262 | 7/1991 | Barlow, Jr. et al. . |
| 5,028,792 | 7/1991 | Mullis . |
| 5,030,243 | 7/1991 | Reinert . |
| 5,030,248 | 7/1991 | Meszaros . |
| 5,034,526 | 7/1991 | Bonham et al. . |
| 5,037,726 | 8/1991 | Kojima et al. . |
| 5,045,435 | 9/1991 | Adams et al. . |
| 5,045,573 | 9/1991 | Kohler et al. . |
| 5,047,556 | 9/1991 | Kohler et al. . |
| 5,049,777 | 9/1991 | Mechtersheimer . |
| 5,053,320 | 10/1991 | Robbillard . |
| 5,055,579 | 10/1991 | Pawlowski et al. . |
| 5,057,562 | 10/1991 | Reinert . |
| 5,068,364 | 11/1991 | Takagaki et al. . |
| 5,069,681 | 12/1991 | Bouwknegt et al. . |
| 5,070,001 | 12/1991 | Stahlhofen . |
| 5,073,448 | 12/1991 | Vieira et al. . |
| 5,074,885 | 12/1991 | Reinert . |
| 5,075,557 | 12/1991 | Haraswa et al. . |
| 5,076,808 | 12/1991 | Hahn et al. . |
| 5,085,698 | 2/1992 | Ma et al. . |
| 5,087,550 | 2/1992 | Blum et al. . |
| 5,089,050 | 2/1992 | Vieira et al. . |
| 5,089,374 | 2/1992 | Saeva . |
| 5,096,456 | 3/1992 | Reinert et al. . |
| 5,096,489 | 3/1992 | Laver . |
| 5,096,781 | 3/1992 | Vieira et al. . |
| 5,098,477 | 3/1992 | Vieira et al. . |
| 5,098,793 | 3/1992 | Rohrbach et al. . |
| 5,098,806 | 3/1992 | Robillard . |
| 5,106,723 | 4/1992 | West et al. . |
| 5,108,505 | 4/1992 | Moffat . |
| 5,108,874 | 4/1992 | Griffing et al. . |
| 5,110,706 | 5/1992 | Yumoto et al. . |
| 5,110,709 | 5/1992 | Aoai et al. . |
| 5,114,832 | 5/1992 | Zertani et al. . |
| 5,124,723 | 6/1992 | Laver . |
| 5,130,227 | 7/1992 | Wade et al. . |
| 5,133,803 | 7/1992 | Moffatt . |
| 5,135,940 | 8/1992 | Belander et al. . |
| 5,139,572 | 8/1992 | Kawashima . |
| 5,139,687 | 8/1992 | Borgher, Sr. et al. . |
| 5,141,556 | 8/1992 | Matrick . |
| 5,141,797 | 8/1992 | Wheeler . |
| 5,144,964 | 9/1992 | Demian . |
| 5,147,901 | 9/1992 | Rutsch et al. . |
| 5,153,104 | 10/1992 | Rossman et al. . |
| 5,153,105 | 10/1992 | Sher et al. . |
| 5,153,166 | 10/1992 | Jain et al. . |
| 5,160,346 | 11/1992 | Fuso et al. . |
| 5,160,372 | 11/1992 | Matrick . |
| 5,166,041 | 11/1992 | Murofushi et al. . |
| 5,169,436 | 12/1992 | Matrick . |
| 5,169,438 | 12/1992 | Matrick . |
| 5,173,112 | 12/1992 | Matrick et al. . |
| 5,176,984 | 1/1993 | Hipps, Sr. et al. . |
| 5,178,420 | 1/1993 | Shelby . |
| 5,180,425 | 1/1993 | Matrick et al. . |
| 5,180,624 | 1/1993 | Kojima et al. . |
| 5,180,652 | 1/1993 | Yamaguchi et al. . |
| 5,181,935 | 1/1993 | Reinert et al. . |
| 5,185,236 | 2/1993 | Shiba et al. . |
| 5,187,045 | 2/1993 | Bonham et al. . |
| 5,187,049 | 2/1993 | Sher et al. . |
| 5,190,565 | 3/1993 | Berenbaum et al. . |
| 5,190,710 | 3/1993 | Kletecka . |
| 5,190,845 | 3/1993 | Hashimoto et al. . |
| 5,193,854 | 3/1993 | Borowski, Jr. et al. . |
| 5,196,295 | 3/1993 | Davis . |
| 5,197,991 | 3/1993 | Rembold . |
| 5,198,330 | 3/1993 | Martic et al. . |
| 5,202,209 | 4/1993 | Winnik et al. . |
| 5,202,210 | 4/1993 | Matsuoka et al. . |
| 5,202,211 | 4/1993 | Vercoulen . |
| 5,202,212 | 4/1993 | Shin et al. . |
| 5,202,213 | 4/1993 | Nakahara et al. . |
| 5,202,215 | 4/1993 | Kanakura et al. . |
| 5,202,221 | 4/1993 | Imai et al. . |
| 5,205,861 | 4/1993 | Matrick . |
| 5,208,136 | 5/1993 | Zanoni et al. . |
| 5,209,814 | 5/1993 | Felten et al. . |
| 5,219,703 | 6/1993 | Bugner et al. . |
| 5,221,334 | 6/1993 | Ma et al. . |
| 5,224,197 | 6/1993 | Zanoni et al. . |
| 5,224,476 | 7/1993 | Schultz et al. . |
| 5,224,987 | 7/1993 | Matrick . |
| 5,226,957 | 7/1993 | Wickramanayake et al. . |
| 5,227,022 | 7/1993 | Leonhardt et al. . |
| 5,241,059 | 8/1993 | Yoshinaga . |
| 5,250,109 | 10/1993 | Chan et al. . |
| 5,254,429 | 10/1993 | Gracia et al. . |
| 5,256,193 | 10/1993 | Winnik et al. . |
| 5,258,274 | 11/1993 | Helland et al. . |
| 5,261,953 | 11/1993 | Vieira et al. . |
| 5,262,276 | 11/1993 | Kawamura . |
| 5,268,027 | 12/1993 | Chan et al. . |
| 5,270,078 | 12/1993 | Walker et al. . |
| 5,271,764 | 12/1993 | Winnik et al. . |
| 5,271,765 | 12/1993 | Ma . |
| 5,272,201 | 12/1993 | Ma et al. . |
| 5,275,646 | 1/1994 | Marshall et al. . |
| 5,279,652 | 1/1994 | Kaufmann et al. . |
| 5,282,894 | 2/1994 | Albert et al. . |
| 5,284,734 | 2/1994 | Blum et al. . |
| 5,286,286 | 2/1994 | Winnik et al. . |
| 5,286,288 | 2/1994 | Tobias et al. . |
| 5,294,528 | 3/1994 | Furutachi . |
| 5,296,275 | 3/1994 | Goman et al. . |
| 5,296,556 | 3/1994 | Frihart . |
| 5,298,030 | 3/1994 | Burdeska et al. . |
| 5,300,403 | 4/1994 | Angelopolus et al. . |
| 5,300,654 | 4/1994 | Nakajima et al. . |

| | | | | | | |
|---|---|---|---|---|---|---|
| 5,302,195 | 4/1994 | Helbrecht . | | 5,686,503 | 11/1997 | Nohr et al. . |
| 5,302,197 | 4/1994 | Wickramanayke et al. . | | 5,700,582 | 12/1997 | Sargeant et al. . |
| 5,310,778 | 5/1994 | Shor et al. . | | 5,700,850 | 12/1997 | Nohr et al. . |
| 5,312,713 | 5/1994 | Yokoyama et al. . | | 5,705,247 | 1/1998 | Arai et al. . |
| 5,312,721 | 5/1994 | Gesign . | | 5,709,955 | 1/1998 | Nohr et al. . |
| 5,324,349 | 6/1994 | Sano et al. . | | 5,709,976 | 1/1998 | Malhotra . |
| 5,328,504 | 7/1994 | Ohnishi . | | 5,721,287 | 2/1998 | Nohr et al. . |
| 5,330,860 | 7/1994 | Grot et al. . | | 5,733,693 | 3/1998 | Nohr et al. . |
| 5,334,455 | 8/1994 | Noren et al. . | | 5,739,175 | 4/1998 | Nohr et al. . |
| 5,338,319 | 8/1994 | Kaschig et al. . | | 5,747,550 | 5/1998 | Nohr et al. . |
| 5,340,631 | 8/1994 | Matsuzawa et al. . | | 5,773,182 | 6/1998 | Nohr et al. . |
| 5,340,854 | 8/1994 | Martic et al. . | | 5,782,963 | 7/1998 | Nohr et al. . |
| 5,344,483 | 9/1994 | Hinton . | | 5,786,132 | 7/1998 | Nohr et al. . |
| 5,356,464 | 10/1994 | Hickman et al. . | | 5,798,015 | 8/1998 | Nohr et al. . |
| 5,362,592 | 11/1994 | Murofushi et al. . | | 5,811,199 | 9/1998 | MacDonald et al. . |
| 5,368,689 | 11/1994 | Agnemo . | | 5,837,429 | 11/1998 | Nohr et al. . |
| 5,372,387 | 12/1994 | Wajda . | | 5,849,411 | 12/1998 | Nohr et al. . |
| 5,372,917 | 12/1994 | Tsuchida et al. . | | 5,855,655 | 1/1999 | Nohr et al. . |
| 5,374,335 | 12/1994 | Lindgren et al. . | | 5,865,471 | 2/1999 | Nohr et al. . |
| 5,376,503 | 12/1994 | Audett et al. . | | | | |

FOREIGN PATENT DOCUMENTS

| | | |
|---|---|---|
| 537687 | 3/1957 | Canada . |
| 552565 | 2/1958 | Canada . |
| 571792 | 3/1959 | Canada . |
| 779239 | 2/1968 | Canada . |
| 930103 | 7/1973 | Canada . |
| 2053094 | 4/1992 | Canada . |
| 94118 | 5/1958 | Czechoslovakia . |
| 0003884 | 9/1979 | European Pat. Off. . |
| 0029284 | 5/1981 | European Pat. Off. . |
| 0127574 | 12/1984 | European Pat. Off. . |
| 0223587 | 5/1987 | European Pat. Off. . |
| 0262533 | 4/1988 | European Pat. Off. . |
| 0280458 | 8/1988 | European Pat. Off. . |
| 0308274 | 3/1989 | European Pat. Off. . |
| 0351615 | 1/1990 | European Pat. Off. . |
| 0371304 | 6/1990 | European Pat. Off. . |
| 0373662 | 6/1990 | European Pat. Off. . |
| 0375160 | 6/1990 | European Pat. Off. . |
| 0390439 | 10/1990 | European Pat. Off. . |
| 0458140A1 | 10/1991 | European Pat. Off. . |
| 0458140 | 11/1991 | European Pat. Off. . |
| 0468465 | 1/1992 | European Pat. Off. . |
| 0542286 | 5/1993 | European Pat. Off. . |
| 000571190 | 11/1993 | European Pat. Off. . |
| 0608433 | 8/1994 | European Pat. Off. . |
| 0609159 | 8/1994 | European Pat. Off. . |
| 0639664 | 2/1995 | European Pat. Off. . |
| 0 716 929 | 6/1996 | European Pat. Off. . |
| 0755984 | 1/1997 | European Pat. Off. . |
| 2245010 | 4/1975 | France . |
| 2383157 | 10/1978 | France . |
| 1047787 | 12/1957 | Germany . |
| 1022801 | 1/1958 | Germany . |
| 1039835 | 9/1958 | Germany . |
| 1040562 | 10/1958 | Germany . |
| 1045414 | 12/1958 | Germany . |
| 1047013 | 12/1958 | Germany . |
| 1132450 | 7/1962 | Germany . |
| 1132540 | 7/1962 | Germany . |
| 1154069 | 9/1963 | Germany . |
| 1240811 | 5/1967 | Germany . |
| 2202497 | 8/1972 | Germany . |
| 2432563 | 2/1975 | Germany . |
| 2437380 | 2/1975 | Germany . |
| 2444520 | 3/1975 | Germany . |
| 2416259 | 10/1975 | Germany . |
| 2714978 | 10/1977 | Germany . |
| 2722264 | 11/1978 | Germany . |
| 158237 | 1/1983 | Germany . |
| 3126433 | 1/1983 | Germany . |
| 3415033 | 10/1984 | Germany . |

| | | | |
|---|---|---|---|
| 5,383,961 | 1/1995 | Bauer et al. . | |
| 5,384,186 | 1/1995 | Trinh . | |
| 5,393,580 | 2/1995 | Ma et al. . | |
| 5,401,303 | 3/1995 | Stoffel et al. . | |
| 5,401,562 | 3/1995 | Akao . | |
| 5,415,686 | 5/1995 | Kurabayashi et al. . | |
| 5,415,976 | 5/1995 | Ali . | |
| 5,424,407 | 6/1995 | Tanaka et al. . | |
| 5,425,978 | 6/1995 | Berneth et al. . | |
| 5,426,164 | 6/1995 | Babb et al. . | |
| 5,427,415 | 6/1995 | Chang . | |
| 5,429,628 | 7/1995 | Trinh et al. . | |
| 5,431,720 | 7/1995 | Nagai et al. . | |
| 5,432,274 | 7/1995 | Luong et al. . | |
| 5,445,651 | 8/1995 | Thoen et al. . | |
| 5,445,843 | 8/1995 | Tanaka et al. . | |
| 5,455,074 | 10/1995 | Nohr et al. . | |
| 5,455,143 | 10/1995 | Ali . | |
| 5,459,014 | 10/1995 | Nishijima et al. . | |
| 5,464,472 | 11/1995 | Horn et al. . | |
| 5,466,283 | 11/1995 | Kondo et al. . | |
| 5,474,691 | 12/1995 | Severns . | |
| 5,475,080 | 12/1995 | Gruber et al. . | |
| 5,476,540 | 12/1995 | Shields et al. . | |
| 5,479,949 | 1/1996 | Battard et al. . | |
| 5,489,503 | 2/1996 | Toan . | |
| 5,498,345 | 3/1996 | Jollenbeck et al. . | |
| 5,501,774 | 3/1996 | Burke . | |
| 5,503,664 | 4/1996 | Sano et al. . | |
| 5,509,957 | 4/1996 | Toan et al. . | |
| 5,531,821 | 7/1996 | Wu . | |
| 5,532,029 | 7/1996 | Fuerst et al. . | |
| 5,532,112 | 7/1996 | Kohler et al. . | |
| 5,541,633 | 7/1996 | Winnik et al. . | |
| 5,543,459 | 8/1996 | Hartmann et al. . | |
| 5,548,010 | 8/1996 | Franer . | |
| 5,569,529 | 10/1996 | Becker et al. . | |
| 5,571,313 | 11/1996 | Mafune et al. . | |
| 5,575,891 | 11/1996 | Trokhan et al. . | |
| 5,580,369 | 12/1996 | Belding et al. . | |
| 5,591,489 | 1/1997 | Dragner et al. . | |
| 5,607,803 | 3/1997 | Murofushi et al. . | |
| 5,616,443 | 4/1997 | Nohr et al. . | |
| 5,635,297 | 6/1997 | Ogawa et al. . | |
| 5,643,356 | 7/1997 | Nohr et al. . | |
| 5,643,631 | 7/1997 | Donigian et al. . | |
| 5,643,701 | 7/1997 | Nohr et al. . | |
| 5,645,964 | 7/1997 | Nohr et al. . | |
| 5,672,392 | 9/1997 | DeClercq et al. . | |
| 5,681,380 | 10/1997 | Nohr et al. . | |
| 5,683,843 | 11/1997 | Nohr et al. . | |
| 5,685,754 | 11/1997 | Nohr et al. . | |

| | | | | | | |
|---|---|---|---|---|---|---|
| 271512 | 9/1989 | Germany . | | 63-243101 | 10/1988 | Japan . |
| 3921600 | 1/1990 | Germany . | | 63-199781 | 12/1988 | Japan . |
| 3833437 | 4/1990 | Germany . | | 64-15049 | 1/1989 | Japan . |
| 3833438 | 4/1990 | Germany . | | 64-29337 | 1/1989 | Japan . |
| 004036328 | 7/1991 | Germany . | | 64-40948 | 2/1989 | Japan . |
| 4132288 | 4/1992 | Germany . | | 89014948 | 3/1989 | Japan . |
| 4126461 | 2/1993 | Germany . | | 1-128063 | 5/1989 | Japan . |
| 662500 | 4/1964 | Italy . | | 1146974 | 6/1989 | Japan . |
| 42-4756 | 2/1967 | Japan . | | 01210477 | 8/1989 | Japan . |
| 43-15663 | 7/1968 | Japan . | | 1288854 | 11/1989 | Japan . |
| 47-26653 | 7/1972 | Japan . | | 2-58573 | 2/1990 | Japan . |
| 47-45409 | 11/1972 | Japan . | | 292957 | 4/1990 | Japan . |
| 49-8909 | 2/1974 | Japan . | | 2179642 | 7/1990 | Japan . |
| 50-65592 | 6/1975 | Japan . | | 2282261 | 11/1990 | Japan . |
| 51-17802 | 2/1976 | Japan . | | 3-134072 | 6/1991 | Japan . |
| 53-104321 | 9/1978 | Japan . | | 03163566 | 7/1991 | Japan . |
| 55-62059 | 5/1980 | Japan . | | 3-170415 | 7/1991 | Japan . |
| 55-90506 | 7/1980 | Japan . | | 3-206439 | 9/1991 | Japan . |
| 56-8134 | 1/1981 | Japan . | | 3-258867 | 11/1991 | Japan . |
| 0014233 | 2/1981 | Japan . | | 5134447 | 11/1991 | Japan . |
| 56-14569 | 2/1981 | Japan . | | 3-203694 | 12/1991 | Japan . |
| 56-24472 | 3/1981 | Japan . | | 3284668 | 12/1991 | Japan . |
| 56-36556 | 4/1981 | Japan . | | 4023884 | 1/1992 | Japan . |
| 57-61055 | 4/1982 | Japan . | | 4023885 | 1/1992 | Japan . |
| 57-128283 | 8/1982 | Japan . | | 4-45174 | 2/1992 | Japan . |
| 57-171775 | 10/1982 | Japan . | | 4100801 | 4/1992 | Japan . |
| 58-124452 | 7/1983 | Japan . | | 4-136075 | 5/1992 | Japan . |
| 58-125770 | 7/1983 | Japan . | | 04356087 | 12/1992 | Japan . |
| 58-222164 | 12/1983 | Japan . | | 543806 | 2/1993 | Japan . |
| 59-89360 | 5/1984 | Japan . | | 561220 | 3/1993 | Japan . |
| 29219270 | 12/1984 | Japan . | | 5080506 | 4/1993 | Japan . |
| 59-219270 | 4/1985 | Japan . | | 05119506 | 5/1993 | Japan . |
| 60-192729 | 10/1985 | Japan . | | 5-140498 | 6/1993 | Japan . |
| 60-239739 | 11/1985 | Japan . | | 2-219869 | 9/1993 | Japan . |
| 60-239740 | 11/1985 | Japan . | | 5263067 | 10/1993 | Japan . |
| 60-239741 | 11/1985 | Japan . | | 680915 | 3/1994 | Japan . |
| 60-239743 | 11/1985 | Japan . | | 6116555 | 4/1994 | Japan . |
| 61-14994 | 1/1986 | Japan . | | 6116556 | 4/1994 | Japan . |
| 61-14995 | 1/1986 | Japan . | | 6116557 | 4/1994 | Japan . |
| 61-21184 | 1/1986 | Japan . | | 6-175584 | 6/1994 | Japan . |
| 61-288 | 1/1986 | Japan . | | 6214339 | 8/1994 | Japan . |
| 61-3781 | 1/1986 | Japan . | | 6256494 | 9/1994 | Japan . |
| 61-25885 | 2/1986 | Japan . | | 6256633 | 9/1994 | Japan . |
| 61-30592 | 2/1986 | Japan . | | 7113828 | 4/1972 | Netherlands . |
| 61-40366 | 2/1986 | Japan . | | 1310767 | 5/1987 | Russian Federation . |
| 61-77846 | 4/1986 | Japan . | | 603767 | 8/1978 | Switzerland . |
| 61-128973 | 6/1986 | Japan . | | 197808 | 5/1988 | Switzerland . |
| 61-97025 | 9/1986 | Japan . | | 1772118 | 10/1992 | U.S.S.R. . |
| 61-222789 | 10/1986 | Japan . | | 275245 | 10/1928 | United Kingdom . |
| 61-247703 | 11/1986 | Japan . | | 349339 | 5/1931 | United Kingdom . |
| 61-285403 | 12/1986 | Japan . | | 355686 | 8/1931 | United Kingdom . |
| 62-7703 | 1/1987 | Japan . | | 399753 | 10/1933 | United Kingdom . |
| 62-100557 | 5/1987 | Japan . | | 441085 | 1/1936 | United Kingdom . |
| 62-97881 | 5/1987 | Japan . | | 463515 | 4/1937 | United Kingdom . |
| 62-127281 | 6/1987 | Japan . | | 492711 | 9/1938 | United Kingdom . |
| 63-43959 | 2/1988 | Japan . | | 518612 | 3/1940 | United Kingdom . |
| 63-48370 | 3/1988 | Japan . | | 539912 | 9/1941 | United Kingdom . |
| 63-95439 | 4/1988 | Japan . | | 626727 | 7/1947 | United Kingdom . |
| 63-95440 | 4/1988 | Japan . | | 600451 | 4/1948 | United Kingdom . |
| 63-95445 | 4/1988 | Japan . | | 616362 | 1/1949 | United Kingdom . |
| 63-95446 | 4/1988 | Japan . | | 618616 | 2/1949 | United Kingdom . |
| 63-95447 | 4/1988 | Japan . | | 779389 | 7/1957 | United Kingdom . |
| 63-95448 | 4/1988 | Japan . | | 1372884 | 11/1974 | United Kingdom . |
| 63-95449 | 4/1988 | Japan . | | 2146357 | 4/1985 | United Kingdom . |
| 63-95450 | 4/1988 | Japan . | | 92/11295 | 7/1992 | WIPO . |
| 63-151946 | 6/1988 | Japan . | | 93/06597 | 4/1993 | WIPO . |
| 63-164953 | 7/1988 | Japan . | | 94/01503 | 1/1994 | WIPO . |
| 63-165498 | 7/1988 | Japan . | | 94/22500 | 10/1994 | WIPO . |
| 63-179977 | 7/1988 | Japan . | | 94/22501 | 10/1994 | WIPO . |
| 63-179985 | 7/1988 | Japan . | | 95/04955 | 2/1995 | WIPO . |
| 63-223077 | 9/1988 | Japan . | | 95/28285 | 10/1995 | WIPO . |
| 63-223078 | 9/1988 | Japan . | | 96/00740 | 1/1996 | WIPO . |

| | | |
|---|---|---|
| 96/19502 | 6/1996 | WIPO . |
| WO 96/19776 | 6/1996 | WIPO . |
| 96/22335 | 7/1996 | WIPO . |
| 96/24636 | 8/1996 | WIPO . |
| 97/20000 | 6/1997 | WIPO . |

OTHER PUBLICATIONS

Abstract for WO 95/00343—A1 *Textiles: Paper: Cellulose* p. 7 1995.

Maki, Y. et al. "A novel heterocyclic N–oxide, pyrimido[5,4–g]pteridinetetrone 5–oxide, with multifunctional photo-oxidative properties" *Chemical Abstracts* 122 925 [No. 122:31350 F] 1995.

Abstract of patent, JP 6–80915 (Canon Inc.), Mar. 22, 1994.

Abstract of patent, JP 06–43573 (Iku Meji) (Feb. 18, 1994).

Pitchumani, K. et al. "Modification of chemical reactivity upon cyclodextrin encapsulation" *Chemical Absracts* 121 982 [No. 121:13362 4v] 1994.

Derwent Publications Ltd., London, JP 05297627 (Fujitsu Ltd.), Nov. 12, 1993. (Abstract).

Patent Abstracts of Japan, JP 5241369 (Bando Chem Ind Ltd et al.), Sep. 21, 1993. (Abstract).

Derwent Publications Ltd., London, JP 05232738 (Yamazaki, T.), Sep. 10, 1993. (Abstract).

Derwent Publications Ltd., London, EP 000559310 (Zeneca Ltd.), Sep. 8, 1993. (Abstract).

Derwent Publications Ltd., London, J,A, 5–230410 (Seiko Epson Corp), Sep. 7, 1993. (Abstract).

Derwent Publications Ltd., London, JP 5–230407 (Mitsubishi Kasei Corp), Sep. 7, 1993. (Abstract).

Abstract Of Patent, JP 405230410 (Seiko Epson Corp.), Sep. 7, 1993. (Abstract).

Abstract Of Patent, JP 405230407 (Mitsubishi Kasei Corp.), Sep. 7, 1993. (Abstract).

Patent Abstracts of Japan, JP 5197198 (Bando Chem Ind Ltd et al.), Aug. 6, 1993. (Abstract).

Database WPI–Derwent Publications Ltd., London, J,A, 5197069 (Bando Chem), Aug. 6, 1993. (Abstract).

Abstract of patent, JP 5–195450 (Nitto Boseki Co. Ltd), Aug. 3, 1993.

Patent Abstracts of Japan, JP5181308 (Bando Chem Ind Ltd et al.), Jul. 23, 1993. (Abstract).

Patent Abstracts of Japan, JP 5181310 (Bando Chem Ind Ltd et al.), Jul. 23, 1993. (Abstract).

Derwent Publications Ltd., London, JP 5–132638 (Mitsubishi Kasei Corp), May 28, 1993. (Abstract).

Abstract Of Patent, JP 405132638 ( Mitsubishi Kasei Corp.), May 28, 1993. (Abstract).

Derwent Publications Ltd., London, JP 5–125318 (Mitsubishi Kasei Corp), May 21, 1993. (Abstract).

Abstract Of Patent, JP 405125318 ( Mitsubishi Kasei Corp.), May 21, 1993. (Abstract).

Abstract of patent, JP 05–117200 (Hidefumi Hirai et al.) (May 14, 1993).

Derwent World Patents Index, JP 5117105 (Mitsui Toatsu Chem Inc.) May 14, 1993.

Derwent Publications Ltd., London, JP 05061246 (Ricoh KK), Mar. 12, 1993. (Abstract).

Husain, N. et al. "Cyclodextrins as mobile–phase additives in reversed–phase HPLC" *American Laboratory* 82 80–87 1993.

Hamilton, D.P. "Tired of Shredding? New Ricoh Method Tries Different Tack" *Wall Street Journal* B2 1993.

"Cyclodextrins: A Breakthrough for Molecular Encapsulation" *American Maize Products Co. (AMAIZO)* 1993.

Duxbury "The Photochemistry and Photophysics of Triphenylmethane Dyes in Solid Liquid Media" *Chemical Review* 93 381–433 1993.

Abstract of patent, JP 04–351603 (Dec. 7, 1992).

Abstract of patent, JP 04–351602 1992.

Derwent Publications Ltd., London, JP 404314769 (Citizen Watch Co. Ltd.), Nov. 5, 1992. (Abstract).

Abstract of patent, JP 04315739 1992.

Derwent Publications Ltd., London, JP 04300395 (Funai Denki KK), Oct. 23, 1992. (Abstract).

Derwent Publications Ltd., London, JP 404213374 (Mitsubishi Kasei Corp), Aug. 4, 1992. (Abstract).

Abstract of patent, JP 04–210228 1992.

Abstract Of Patent, JP 404202571 (Canon Inc.), Jul. 23, 1992. (Abstract).

Abstract Of Patent, JP 404202271 (Mitsubishi Kasei Corp.), Jul. 23, 1992. (Abstract).

Derwent Publications Ltd., London, JP 4–189877 (Seiko Epson Corp), Jul. 8, 1992. (Abstract).

Derwent Publications Ltd., London, JP 404189876 (Seiko Epson Corp), Jul. 8, 1992. (Abstract).

Abstract Of Patent, JP 404189877 (Seiko Epson Corp.), Jul. 8, 1992. (Abstract).

Derwent Publications Ltd., London, J,A, 4–170479 (Seiko Epson Corp), Jun. 18, 1992. (Abstract).

Abstract of patent, JP 04–81402 1992.

Abstract of patent, JP 04–81401 1992.

Kogelschatz "Silent–discharge driven excimer UV sources and their applications" *Applied Surface Science* 410–423 1992.

Derwent Publications, Ltd., London, JP 403269167 (Japan Wool Textile KK), Nov. 29, 1991 (Abstract).

Derwent Publications Ltd., London, JO 3247676 (Canon KK), Nov. 5, 1991 (Abstract).

Abstract of patent, JP 03–220384 1991.

Patent Abstracts of Japan, JP 03184896 (Dainippon Printing Co Ltd.) Aug. 12, 1991.

Derwent Publications Ltd., London, JP 3167270 (Mitsubishi Kasei Corp), Jul. 19, 1991. (Abstract).

Derwent Publications Ltd., London, JO 3167270 (Mitsubishi Kasei Corp.), Jul. 19, 1991 (Abstract).

Derwent Publications Ltd., London, JO 3093870 (Dainippon Ink Chem KK.), Apr. 18, 1991 (Abstract).

Abstract of patent, JP 06369890 1991.

Kogelschatz, U. et al. "New Excimer UV Sources for Industrial Applications" *ABB Review* 391 1–10 1991.

Abstract of patent, JP 03–41165 1991.

"Coloring/Decoloring Agent for Tonor Use Developed" *Japan Chemical Week* 1991.

Braithwaite, M., et al. "Formulation" *Chemistry & Technology of UV & EB Formulation for Coatings, Inks & Paints* IV 11–12 1991.

*Scientific Polymer Products, Inc. Brochure* 24–31 1991.

Dietliker, K. "Photoiniators for Free Radical and Catioinc Polymerisation" *Chem & Tech of UV & EB Formulation for Coatings, Inks & Paints* III 61, 63, 229–232, 280, 405, 1991.

Esrom et al. "Large area Photochemical Dry Etching of Polymers iwth Incoherent Excimer UV Radiation" *MRS Materials Research Society* 1–7 1991.

Esrom et al. Excimer Laser–Induced Decompostion of Aluminum Nitride *Materials Research Society Fall Meeting* 1–6 1991.

Esrom et al. "Metal deposition with a windowless VUV excimer source" *Applied Surface Science* 1–5 1991.

Esrom "Excimer Laser–Induced Surface Activation of Aln for Electroless Metal Deposition" *Mat. Res. Sco.lSymp. Proc.* 204 457–465 1991.

Zhang et al. "UV–induced decompositin of adsorbed Cu–acetylacetonate films at room temperature for electroless metal plating" *Applied Surface Science* 1–6 1991.

"German company develops reuseable paper" *Pulp & Paper* 1991.

Abstract of patent, JP 02289652 1990.

Ohashi et al. "Molecular Mechanics Studies on Inclusion Compounds of Cyanine Dye Monomers and Dimers in Cyclodextrin Cavities," *J. Am. Chem. Soc.* 112 5824–5830 1990.

Kogelschatz et al. "New Incoherent Ultraviolet Excimer Sources for Photolytic Material Deposition," *Laser Und Opteolektronik* 1990.

Patent Abstracts of Japan, JP 02141287 (Dainippon Printing Co Ltd.) May 30, 1990.

Abstract of Patent, JP 0297957, (Fuji Xerox Co., Ltd.) 1990.

Derwent Publications Ltd., London, JP 2091166 (Canon KK), Mar. 30, 1990. (Abstract).

Esrom et al. "Metal Deposition with Incoherent Excimer Radiation" *Mat. Res. Soc. Symp. Proc.* 158 189–198 1990.

Esrom "UV Excimer Laer–Induced Deposition of Palladium from Palladiym Acetate Films" *Mat. Res. Soc. Symp. Proc.* 158 109–117 1990.

Kogelschatz, U. "Silent Discharges for the Generation of ultraviolet and vacuum ultraviolet excimer radiation" *Pure & Applied Chem.* 62 1667–74 1990.

Esrom et al. "Investigation of the mechanism of the UV–induced palladium depostions processf from thin solid palladium acetate films" *Applied Surface Science* 46 158–162 1990.

Zhang et al. "VUV synchrotron radiation processing of thin palladium acetate spin–on films for metallic surface patterning" *Applied Surface Science* 46 153–157 1990.

Brennan et al. "Tereoelectronic effects in ring closure reactions: the 2'–hydroxychalcone—flavanone equilibrium, and related systems," *Canadian J. Chem.* 68 (10) pp. 1780–1785 1990.

Abstract of patent, JP 01–299083 1989.

Derwent Publications Ltd., London, J,O, 1182379 (Canon KK), Jul. 20, 1989. (Abstract).

Derwent Publications Ltd., London, JO 1011171 (Mitsubishi Chem Ind. KK.), Jan. 13, 1989 (Abstract).

Gruber, R.J., et al. "Xerographic Materials" *Encyclopedia of Polymer Science and Engineering* 17 918–943 1989.

Pappas, S.P. "Photocrosslinking" *Comph. Pol. Sci.* 6 135–148 1989.

Pappas, S.P. "Photoinitiated Polymerization" *Comph. Pol. Sci.* 4 337–355 1989.

Kirilenko, G.V. et al. "An analog of the vesicular process with amplitude modulation of the incident light beam" *Chemical Abstracts* 111 569 [No. 111:12363 3b] 1989.

Esrom et al. "UV excimer laser–induced pre–nucleation of surfaces followed by electroless metallization" *Chemtronics* 4 216–223 1989.

Esrom et al. "VUV light–induced depostion of palladium using an incoherent Xe2* excimer source" *Chemotronics* 4 1989.

Esrom et al. "UV Light–Induced Depostion of Copper Films" C5–719—C5–725 1989.

Falbe et al. *Rompp Chemie Lexikon* 9 270 1989.

Allen, Norman S. *Photopolymerisation and Photoimaging Science and Technology* pp. 188–199; 210–239 1989.

Derwent Publications, Ltd., London, SU 1423656 (Kherson Ind Inst), Sep. 15, 1988 (Abstract).

Derwent Publications, Ltd., London, EP 0280653 (Ciba GeigyAG), Aug. 31, 1988 (Abstract).

Abstract of patent, JP 63–190815 1988.

Patent Abstracts of Japan, JP 63179985 (Tomoegawa Paper Co. Ltd.), Jul. 23, 1988.

Derwent World Patents Index, JP 63179977 (Tomoegawa Paper Mfg Co Ltd), Jul. 23, 1988.

Furcone, S.Y. et al. "Spin–on B14Sr3Ca3Cu4016+× superconducting thin films from citrate precursors," *Appl. Phys. Lett.* 52(2 5) 2180–2182 1988.

Abstract of patent, JP 63–144329 1988.

Abstract of patent, JP 63–130164 1988.

Derwent Publications, Ltd., London, J6 3112770 (Toray Ind Inc), May 17, 1988 (Abstract).

Derwent Publications, Ltd., London, J6 3108074 (Konishiroku Photo KK), May 12, 1988 (Abstract).

Derwent Publications, Ltd., London,J6 3108073 (Konishiroku Photo KK), May 12, 1988 (Abstract).

Abstract of patent, JP 61–77846 1988.

Abstract of patent, JP 63–73241 1988.

Abstract of patent, JP 6347762, 1988.

Abstract of patent, JP 63–47763, 1988.

Abstract of patent, JP 63–47764, 1988.

Abstract of patent, JP 63–47765, 1988.

Eliasson, B., et al. "UV Excimer Radiation from Dielectric–Barrier Discharges" *Applied Physics B* 46 299–303 1988.

Eliasson et al. "New Trends in High Intensity UV Generation" *EPA Newsletter* (32) 29–40 1988.

Cotton, F.A. "Oxygen: Group Via(16)" *Advanced Inorganic Chemistry* 5th ed. 473–474 1988.

Derwent Publications, Ltd., London, J6 2270665 (Konishiroku Photo KK), Nov. 25, 1987 (Abstract).

Abstract of patent, JP 62–215621 1987.

Database WPI, Derwent Publications Ltd., London, JP 62032082 (Mitsubishi Denki KK), Feb. 12, 1987. (Abstract).

Abstract of patent, JP 62–32082 1987.

Derwent Publications Ltd., London, J6 2007772 (Alps Electric KK.), Jan. 14, 1987 (Abstract).

Gross et al. "Laser direct–write metallization in thin palladium acetate films" *J. App. Phys.* 61 (4) 1628–1632 1987.

Al–Ismail et al. "Some experimental results on thin polypropylene films loaded with finely–dispersed copper" *Journal of Materials Science* 415–418 1987.

Baufay et al. "Optical self–regulation during laser–induced oxidation of copper" *J. Appl. Phys* 61 (9) 4640–4651 1987.

Derwent Publications Ltd., London, JA 0284478 (Sanyo Chem Ind Ltd.), Dec. 15, 1986 (Abstract).

Abstract of patent, JP 61251842 1986.

Database WPI, Derwent Publications Ltd., London, GB; SU, A, 1098210 (Kutulya L A) Jun. 23, 1986.

Abstract of patent, JP 61–97025 1986.

Abstract of patent, JP 61–87760 1986.

Derwent Publications Ltd., London, DL 0234731 (Karl Marx Univ. Leipzig), Apr. 9, 1986. (Abstract).

Derwent World Patents Index, SU 1219612 (AS USSR NON–AQ SOLN) Mar. 23, 1986.

Derwent Publications, Ltd., London, J6 1041381 (Osaka Prefecture), Feb. 27, 1986 (Abstract).

Dialog, JAPIO, JP 61–034057 (Ciba Geigy AG) Feb. 18, 1986.

Derwent World Patents Index, JP 61027288 (sumitomo Chem Ind KK) Feb. 6, 1986.
Sakai et al. "A Novel and Practical Synthetic Method of 3(2H)–Furanone Derivatives," *J. Heterocyclie Chem.* 23 pp. 1199–1201 1986.
Jellinek, H.H.G. et al. "Evolution of H2O and CO2 During the Copper–Catalyzed Oxidation of Isotactic Polypropylene," *J. Polymer Sci.* 24 389–403 1986.
Jellinek, H.H.G. et al. "Diffusion of Ca2+ Catalysts from Cu–Metal Polymer or Cu–Oxide/Polymer Interfaces into Isotactic Polypropylene," *J. Polymer Sci.* 24 503–510 1986.
John J. Eisch and Ramiro Sanchez "Selective, Oxophilic Imination of Ketones with Bis (dichloroaluminum) Phenylimide" *J. Org. Chem.* 51 (10) 1848–1852 1986.
Derwent Publications Ltd., London, J6 0226575 (Sumitomo Chem Ind Ltd.), Oct. 11, 1985 (Abstract).
Abstract of patent, JP 60–156761 1985.
Derwent Publications Ltd., London, J,A, 0011451 (Fugi Photo Film KK), Jan. 21, 1985. (Abstract).
Derwent Publications, Ltd., London J6 0011–449–A (Taoka Chemical KK) Jan. 21, 1985 (abstract).
Roos, G. et al. "Textile applications of photocrosslinkable polymers" *Chemical Abstracts* 103 57 [No. 103:23690j ] 1985.
Derwent World Patents Index, EP 127574 (Ciba Geigy AG), Dec. 5, 1984.
Derwent Publications Ltd., London, JP 0198187 (Canon KK), Nov. 9, 1984. (Abstract).
Derwent Publications Ltd., London, J,A, 0169883 (Ricoh KK), Sep. 25, 1984. (Abstract).
Derwent Publications Ltd., London, JA 0169883 (Ricoh KK), Sep. 25, 1984 (Abstract).
Derwent Publications Ltd., London, JA 0198187 (Canon KK), Sep. 11, 1984 (Abstract).
Derwent Publications Ltd., London, J,A, 0053563 (Dainippon Toryo KK), Mar. 28, 1984. (Abstract).
Derwent Publications Ltd., London, J,A, 0053562 (Dainippon Toryo KK), Mar. 28, 1984. (Abstract).
Derwent Publications Ltd., London, J,A, 0051961 (Dainippon Toryo KK), Mar. 26, 1984). (Abstract) 1984.
Saenger, W. "Structural Aspects of Cyclodextrins and Their Inclusion Complexes" *Inclusion Compounds—Structural Aspects of Inclusion Compounds formed by Organic Host* 2 231–259 1984.
Szejtli "Industrial Applications of Cyclodextrins" *Inclusion Compounds: Physical Prop. & Applns* 3 331–390 1984.
Kano et al. "Three–Component Complexes of Cyclodextrins. Exciplex Formation in Cyclodextrin Cavity," *J. Inclusion Phenomena* 2 pp. 737–746 1984.
Suzuki et al. "Spectroscopic Investigation of Cyclodextrin Monomers, Derivatives, Polymers and Azo Dyes," *J. Inclusion Phenomena* 2, pp. 715–724 1984.
Abstract of Patent, JA 0222164 (Ricoh KK), Dec. 23, 1983 (Abstract).
Abstract of patent, JP 58211426 (Sekisui Plastics KK), (Dec. 8, 1983).
Derwent Publications, Ltd., London, EP 0072775 (Ciba Geigy AG), Feb. 23, 1983 (Abstract).
van Beek, H.C.A. "Light–Induced Colour Changes in Dyes and Materials" *Color Res. and Appl.* 8 176–181 1983.
Connors, K.A. "Application of a stoichiometric model of cyclodextrin complex formation" *Chemical Abstracts* 98 598 [No. 98:53067g] 1983.
Abstract of Patent, EP 0065617 (IBM Corp.), Dec. 1, 1982 (Abstract).
Derwent Publications Ltd., London, J,A, 0187289 (Honshu Paper Mfg KK), Nov. 17, 1982. (Abstract).
Abstract of Patent, JA 0187289 (Honsho Paper Mfg KK), Nov. 17, 1982 (Abstract).
Abstract of Patent, JA 0185364 (Ricoh KK), Nov. 15, 1982 (Abstract).
Derwent Publications, Ltd., London J5 7139–146 (Showa Kako KK) Aug. 27, 1982(abstract).
Abstract of Patent, JA 0090069 (Canon KK), Jun. 4, 1982 (Abstract).
Derwent Publications, Ltd., London, JA 0061785 (Nippon Senka KK), Apr. 14, 1982 (Abstract).
Fischer, "Submicroscopic contact imaging with visible light by energy transfer" *Appl. Phys. Letter* 40(3) 1982.
Abstract of Patent, JA 0010659 (Canon KK), Jan. 2, 1982 (Abstract).
Abstract of Patent, JA 0010661 (Canon KK), Jan. 2, 1982 (Abstract).
Christen "Carbonylverbindungen: Aldehyde und Ketone," *Grundlagen der Organischen Chemie* 255 1982.
Derwent Publications Ltd., London, J,A, 0155263 (Canon KK), Dec. 1, 1981. (Abstract).
Abstract of Patent, JA 0155263 (Canon KK), Dec. 1, 1981 (Abstract).
Abstract of Patent, JA 0147861 (Canon KK), Nov. 17, 1981 (Abstract).
Derwent Publications Ltd., London, J,A, 0143273 (Canon KK), Nov. 7, 1981 (Abstract).
Abstract of Patent, JA 0143272 (Canon KK), Nov. 7, 1981 (Abstract).
Abstract of Patent, JA 0136861 (Canon KK), Oct. 26, 1981 (Abstract).
Abstract of Patent, JA 6133378 (Canon KK), Oct. 19, 1981 (Abstract).
Abstract of Patent, JA 6133377 (Canon KK), Oct. 19, 1981 (Abstract).
Abstract of Patent, JA 6093775 (Canon KK), Jul. 29, 1981 (Abstract).
Derwent Publications Ltd., London, J,A, 0008135 (Ricoh KK), Jan. 27, 1981. (Abstract).
Derwent Publications Ltd., London, J,A, 0004488 (Canon KK), Jan. 17, 1981. (Abstract).
Abstract of Patent, JA 0004488 (Canon KK), Jan. 17, 1981 (Abstract).
Kirk–Othmer "Metallic coatings," *Encylcopedia of Chemical Technology* 15 241–274 1981.
Komiyama et al. "One–Pot Preparation of 4–Hydroxychalcone β–Cyclodextrin as Catalyst," *Makromol. Chem.* 2 733–734 1981.
Derwent Publications, Ltd., London CA 1086–719 (Sherwood Medical) Sep. 30, 1980 (abstract).
Derwent Publications Ltd., Database WPI, JP 55 113036 (Ricoh KK), Sep. 1, 1980.
Rosanske et al. "Stoichiometric Model of Cyclodextrin Complex Formation" *Journal of Pharmaceutical Sciences* 69 (5) 564–567 1980.
Semple et al. "Synthesis of Functionalized Tetrahydrofurans," *Tetrahedron Letters* 81 pp. 4561–4564 1980.
Kirk–Othmer "Film Deposition Techniques," *Encyclopedia of Chemical Technology* 10 247–283 1980.
Derwent World Patents Index, Derwent Info. Ltd., JP 54158941 (Toyo Pulp KK), Dec. 15, 1979. (Abstract).
Derwent World Patents Index, JP 54117536 (Kawashima F) Sep. 12, 1979,.

Derwent Publications Ltd., London, J,A, 0005422 (Fuji Photo Film KK), Jan. 16, 1979. (Abstract).
Drexhage et al. "Photo–bleachable dyes and processes" *Research Disclosure* 85–87 1979.
"Color imaging devices and color filter arrays using photo–bleachable dyes" *Research Disclosure* 22–23 1979.
Wolff, N.E., et al. "Electrophotography" *Kirk–Othmer Encyclopedia of Chemical Technology* 8 794–826 1979.
Derwent Publications Ltd., London, J,A, 0012037 (Pentel KK), Jan. 29, 1977. (Abstract).
Abstract of Patent, JA 0012037 (Pentel KK), Jan. 29, 1977 (Abstract).
Jenkins, P.W. et al. "Photobleachable dye material" *Research Disclosure* 18 [No. 12932] 1975.
Lamberts, R.L. "Recording color grid patterns with lenticules" *Research Disclosure* 18–19 [No. 12923] 1975.
Karmanova, L.S. et al. "Light stabilizers of daytime fluorescent paints" *Chemical Abstracts* 82 147 [No. 59971p] 1975.
Prokopovich, B. et al. "Selection of effective photoinducers for rapid hardening of polyester varnish PE–250" *Chemical Abstracts* 83 131 [No. 81334a] 1975.
"Variable Contrast Printing System" *Research Disclosure* 19 [No. 12931] 1975.
Lakshman "Electronic Absorption Spectrum of Copper Formate Tetrahydrate" *Chemical Physics Letters* 31 (2) 331–334 1975.
Derwent Publcations, Ltd., London J4 9131–226 (TNational Cash Register C) Dec. 16, 1974 (abstract).
Chang, I.F., et al. "Color Modulated Dye Ink Jet Printer" *IBM Technical Disclosure Bulletin* 17(5) 1520–1521 1974.
"Darocur 1173: Liquid Photoiniator for Ultraviolet Curing of Coatings" 1974.
Hosokawa et al. "Ascofuranone, an antibiotic from Ascochyta," Japan Kokai 73 91,278 (Nov. 28, 1973) *Merck Index* 80 p. 283; abstract 94259t 1974.
Abstract of patent, NL 7112489 (Dec. 27, 1971).
Gafney et al. "Photochemical Reactions of Copper (II)—1, 3–Diketonate Complexes" *Journal of the Americqal Chemical Society* 1971.
Derwent Publications, Ltd., London SU 292698–S Jan. 15, 1971 (abstract).
Derwent World Patents Index,CS 120380 (Kocourek, Jan) Oct. 15, 1966.
Rigdon, J.E. "In Search of Paper that Spies Can't Copy" *Wall Street Journal*.
Chatterjee,S. et al. "Photochemistry of Carbocyanine Alkyltriphenylborate Salts: Intra–Ion–Pair Electron Transfer and the Chemistry of Boranyl Radicals" *J. Am. Chem. Soc.* 112 6329–6338.
"Assay—Physical and Chemical Analysis of Complexes" *AMAIZO*.
"Cyclodextrin" *AMAIZO*.
"Beta Cyclodextrin Polymer (BCDP)" *AMAIZO*.
"Chemically Modified Cyclodextrins" *AMAIZO*.
"Cyclodextrin Complexation" American Maize Products Co.
"Monomers" Scientific Polymer Products Inc.
Suppan, Paul "Quenching of Excited States" *Chemistry and Light* 65–69.
Yamaguchi, H. et al. "Supersensitization. Aromatic ketones as supersensitizers" *Chemical Abstract* 53 107 (d).
Stecher, H. "Ultraviolet–absorptive additives in adhesives, lacquers and plastics" *Chemical Abstracts* 53 14579 (c).
Maslennikov, A.S. "Coupling of diazonium salts with ketones" *Chemical Abstracts* 60 3128e.
Derwent Publications Ltd., London, 4 9128022.
Abstracts of Patent, JP 405195450.
Rose, Philip I. "Gelatin," *Encyclopedia of Chemical Technology* 7 488–513.
U.S. application No. 08/103,503, filed Aug. 5, 1993.
U.S. application No. 08/119,912, filed Sep. 10, 1993.
U.S. application No. 08/183,683, filed Jan. 19, 1994.
U.S. application No. 08/258,858, filed Jun. 13, 1994.
U.S. application No. 08/268,685, filed Jun. 30, 1994.
U.S. application No. 08/327,077, filed Oct. 21, 1994.
U.S. application No. 08/336,813, filed Nov. 9, 1994.
U.S. application No. 08/359,670, filed Dec. 20, 1994.
U.S. application No. 08/360,501, filed Dec. 21, 1994.
U.S. application No. 08/373,958, filed Jan. 17, 1995.
U.S. application No. 08/393,089, filed Feb. 22, 1995, now U.S. Pat. No. 5,683,843.
U.S. application No. 08/403,240, filed Mar. 10, 1995.
U.S. application No. 08/444,670, filed May 19, 1995, now U.S. Pat. No. 5,685,754.
U.S. application No. 08/444,780, filed May 19, 1995.
U.S. application No. 08/453,912, filed May 30, 1995.
U.S. application No. 08/456,784, filed Jun. 1, 1995, now U.S. Pat. No. 5,616,443.
U.S. application No. 08/457,025, filed Jun. 1, 1995, now U.S. Pat. No. 5,643,701.
U.S. application No. 08/461,365, filed Jun. 5, 1995.
U.S. application No. 08/461,372, filed Jun. 5, 1995.
U.S. application No. 08/461,373, filed Jun. 5, 1995.
U.S. application No. 08/461,382, filed Jun. 5, 1995.
U.S. application No. 08/461,445, filed Jun. 5, 1995, now U.S. Pat. No. 5,721,287.
U.S. application No. 08/461,656, filed Jun. 5, 1995.
U.S. application No. 08/461,991, filed Jun. 5, 1995.
U.S. application No. 08/462,101, filed Jun. 5, 1995.
U.S. application No. 08/462,103, filed Jun. 5, 1995, now U.S. Pat. No. 5,645,964.
U.S. application No. 08/462,105, filed Jun. 5, 1995.
U.S. application No. 08/462,107, filed Jun. 5, 1995.
U.S. application No. 08/462,214, filed Jun. 5, 1995, now U.S. Pat. No. 5,811,199.
U.S. application No. 08/462,217, filed Jun. 5, 1995.
U.S. application No. 08/463,103, filed Jun. 5, 1995.
U.S. application No. 08/463,185, filed Jun. 5, 1995.
U.S. applicatioin No. 08/463,187, filed Jun. 5, 1995.
U.S. application No. 08/463,188, filed Jun. 5, 1995.
U.S. application No. 08/463,189, filed Jun. 5, 1995, now U.S. Pat. No. 5,798,015.
U.S. application No. 08/463,496, filed Jun. 5, 1995, now U.S. Pat. No. 5,700,850.
U.S. application No. 08/464,216, filed Jun. 5, 1995.
U.S. application No. 08/465,376, filed Jun. 5, 1995.
U.S. application No. 08/465,377, filed Jun. 5, 1995, now U.S. Pat. No. 5,643,356.
U.S. application No. 08/465,393, filed Jun. 5, 1995, Now U.S. Pat. No. 5,773,182.
U.S. application No. 08/465,397, filed Jun. 5, 1995.
U.S. application No. 08/465,655, filed Jun. 5, 1995, now U.S. Pat. No. 5,747,550.
U.S. application No. 60/000,570, filed Jun. 28, 1995.
U.S. application No. 08/537,593, filed Oct. 2, 1995.
U.S. application No. 08/563,381, filed Nov. 28, 1995.
U.S. application No. 08/589,321, filed Jan. 22, 1996.

U.S. application No. 08/589,449, filed Jan. 22, 1996, now U.S. Pat. 5,686,503.
U.S. application No. 08/625,737, filed Mar. 29, 1996.
U.S. application No. 08/627,693, filed Mar. 29, 1996.
U.S. application No. 08/649,754, filed May 29, 1996, now U.S. Pat. No. 5,786,132.
U.S. application No. 08/649,755, filed May 29, 1996.
U.S. application No. 08/659,497, filed Jun. 5, 1996, now U.S. Pat. No. 5,837,429.
U.S. application No. 08/733,086, filed Oct. 16, 1996, now U.S. Pat. No. 5,709,955.
U.S. application No. 08/757,222, filed Nov. 27, 1996, now U.S. Pat. No. 5,782,963.
U.S. application No. 08/769,885, filed Dec. 19, 1996, now U.S. Pat. No. 5,681,380.
U.S. application No. 08/777,996, filed Jan. 2, 1997, now U.S. Pat. No. 5,733,693.
U.S. application No. 08/788,863, filed Jan. 23, 1997.
U.S. application No. 08/843,410, filed Apr. 15, 1997.
U.S. application No. 08/839,109, filed Apr. 23, 1997.
U.S. application No. 08/857,454, filed May 16, 1997.
U.S. application No. 08/903,911, filed Jul. 31, 1997.
U.S. Provisional application Ser. No. 60/055,785, filed Aug. 15, 1997.
U.S. application No. 08/936,449, filed Sep. 24, 1997.
U.S. application No. 08/946,952, filed Oct. 8, 1997.
U.S. Provisional application Ser. No. 60/062,643, filed Oct. 22, 1997.
U.S. application No. 08/979,769, filed Nov. 26, 1997.
U.S. application No. 08/983,159, filed Dec. 26, 1997.
U.S. application No. 08/998,464, filed Dec. 26, 1997.
U.S. application No. 09/002,300, filed Dec. 31, 1997.
U.S. Provisional application Ser. No. 60/071,944, filed Jan. 20, 1998.
U.S. Provisional application Ser. No. 60/071,937, filed Jan. 20, 1998.
U.S application No. 09/012,064, filed Jan. 22, 1998.
U.S. application No. 09/018,129, filed Feb. 3, 1998.
U.S. application No. 08/951,183, filed Oct. 31, 1997.
U.S. application No. 09/021,552, filed Feb. 10, 1998.
U.S. application No. 09/058,385, filed Apr. 9, 1998.
U.S. Provisional application Ser. No. 60/082,143, filed Apr. 17, 1998.
U.S. application No. 09/070,126, filed Apr. 29, 1998.
U.S. Provisional application Ser. No. 60/087,893, filed Jun. 3, 1998.
U.S. Provisional application Ser. No. 60/087,866, filed Jun. 3, 1998.
U.S. Provisional application Ser. No. 60/089,528, filed Jun. 15, 1998.
U.S. Provisional application Ser. No. 60/093,458, filed Jul. 20, 1998.
U.S. application No. 09/133,574, filed Aug. 13, 1998.
U.S. Provisional application Ser. No. 60/102,153, filed Sep. 28, 1998.
U.S. application No. 07/997,799, filed Dec. 29, 1992, now Pat. No. 5,455,074.
U.S. application No. 09/192,628, filed Nov. 16, 1998.
U.S. application No. 09/204,875, filed Dec. 3, 1998.
U.S. application No. 09/205,405, filed Dec. 3, 1998.
U.S. application No. 09/204,774, filed Dec. 3, 1998.
U.S. application No. 09/205,542, filed Dec. 3, 1998.
U.S. application No. 09/205,546, filed Dec. 3, 1998.
U.S. Provisional application Ser. No. 60/111,950, filed Dec. 11, 1998.
U.S. application No. 09/210,229, filed Dec. 11, 1998.
U.S. application No. 09/211,895, filed Dec. 15, 1998.
U.S. Provisional application Ser. No. 60/116,315, filed Jan. 19, 1999.
U.S. Provisional application Ser. No. 60/121,302, filed Feb. 23, 1999.
U.S. Provisional application Ser. No. 60/121,301, filed Feb. 23, 1999.

Fig_1

Fig_2

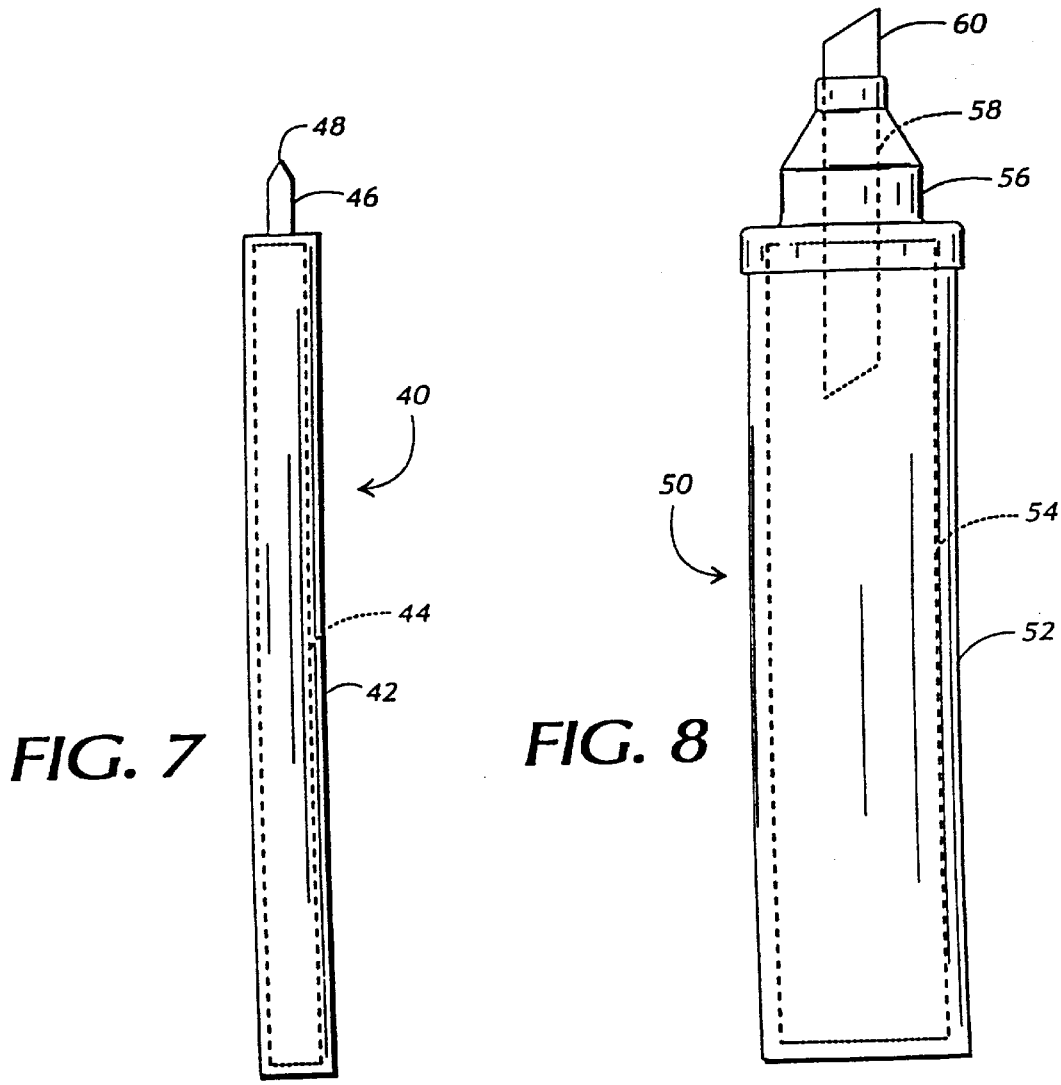
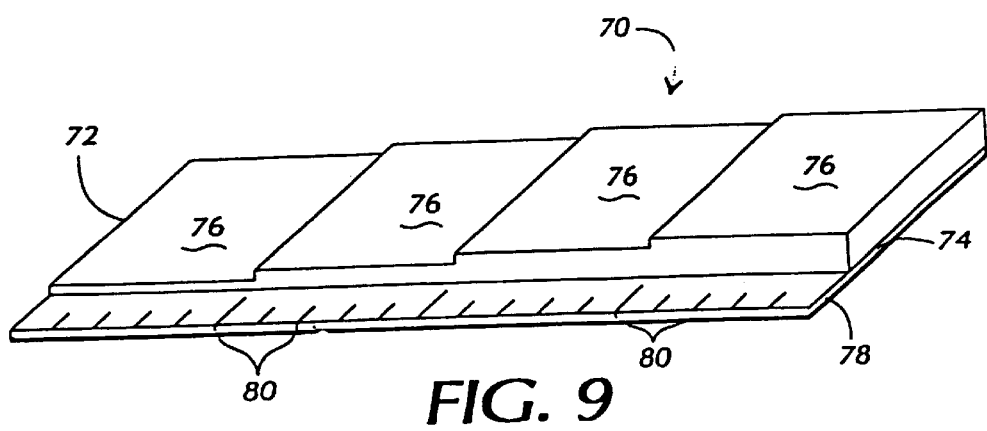

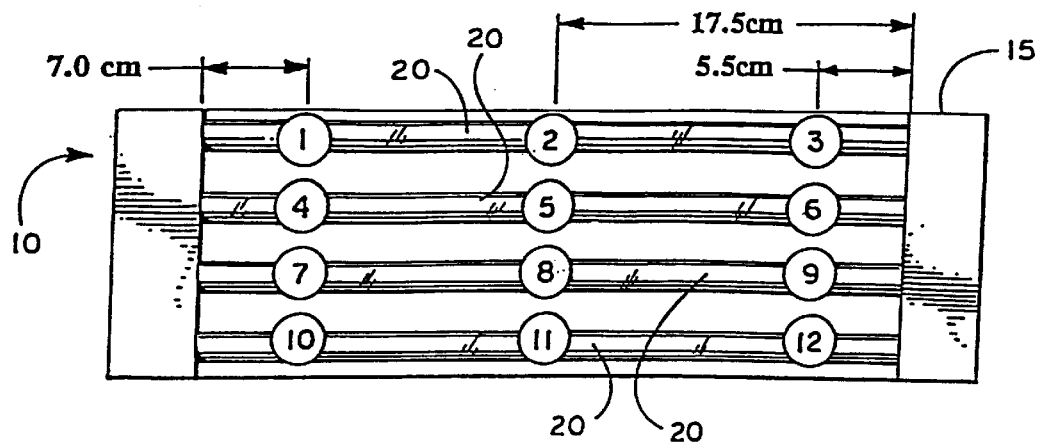
FIG. 14
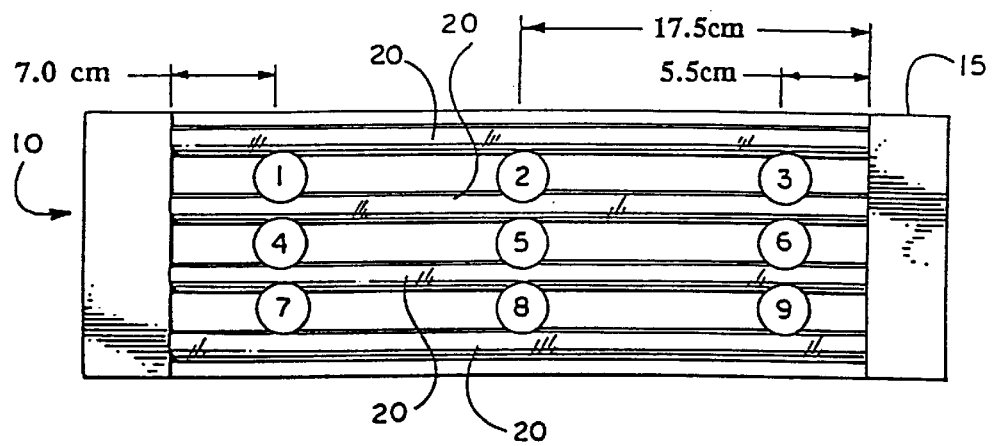
FIG. 15
FIG. 16
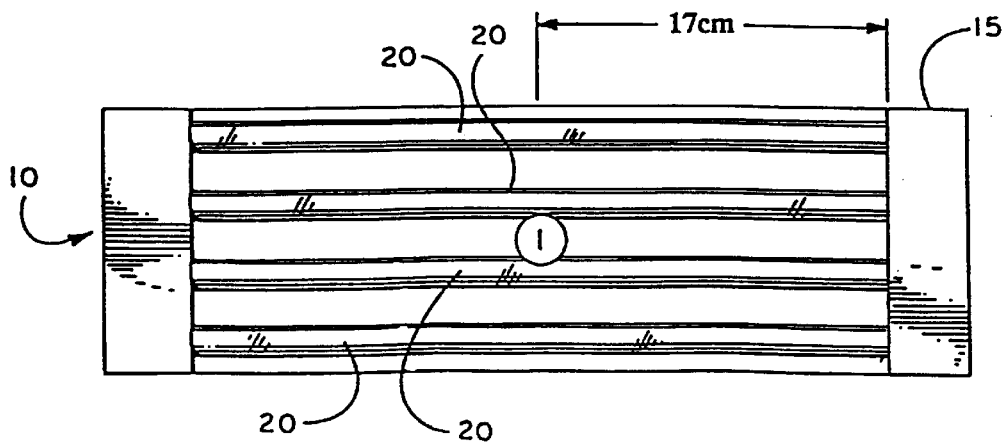

METHOD FOR CONCEALING INFORMATION AND DOCUMENT FOR SECURELY COMMUNICATING CONCEALED INFORMATION

CROSS-REFERENCE TO RELATED APPLICATIONS

This application is a divisional of U.S. patent application Ser. No. 08/946,953, filed on Oct. 8, 1997, which is incorporated herein by reference and is a continuation of U.S. patent application Ser. No. 08/462,105, filed on Jun. 5, 1995, now abandoned, which is incorporated herein by reference and is a continuation in part of U.S. patent application Ser. No. 08/336,813, filed Nov. 9, 1994, now abandoned, and is a continuation-in-part patent application of U.S. patent application Ser. No. 08/403,240 entitled Method and Compositions For Stabilizing Colorants, filed on Mar. 10, 1995, now abandoned, which is incorporated herein by reference, and is a continuation-in-part patent application of U.S. patent application Ser. No. 08/373,958, filed on Jan. 17, 1995, now abandoned, which is incorporated herein by reference and is a continuation-in-part of U.S. patent application Ser. No. 08/360,501, filed on Dec. 21, 1994, now U.S. Pat. No. 5,865,471, which is incorporated herein by reference, and U.S. patent application Ser. No. 08/359,670, filed on Dec. 20, 1994, now abandoned, which is incorporated herein by reference, both of which are continuation-in-part patent applications of U.S. patent application Ser. No. 08/258,858, filed on Jun. 13, 1994, now abandoned, which is incorporated herein by reference and is a continuation-in-part patent application of U.S. patent application Ser. No. 08/119,912, filed Sep. 10, 1993, now abandoned, which is incorporated herein by reference, and is a continuation-in-part patent application of U.S. patent application Ser. No. 08/103,503, filed on Aug. 5, 1993, now abandoned, which is incorporated herein by reference.

TECHNICAL FIELD

This application relates to uses of photoerasable colorants which are stable to natural light and artificial light. Such applications include temporary price marking of goods, communicating concealed information such as win/loss status on gaming tickets, temporary marking of terrain and structures such as roadways and buildings, temporary underlining or highlighting of text, ultraviolet radiation exposure indication, and direct printing on articles such as plastic containers, plastic films, and paper.

BACKGROUND OF THE INVENTION

Temporary marking is desirable in many instances, but removing the marking can be difficult and costly, or at least annoying. For example, temporary marking is desirable for price marking products for retail sale so that the price can be changed by the retailer or the purchaser can remove the price before giving the product to a recipient. To change the price on a product, a retailer often has to remove the existing price tag or label and replace it with a new one or place a new price label over the existing marking. When a price marking is removed by a customer, substantially the entire label or tag must be removed which can involve scrapping off the adhesive label or cutting off the tag. Accordingly, there is a need for a temporary price marking which can be easily removed and replaced or changed.

Another example for the need for temporary marking is in the communication of concealed information such as the win/loss status on gaming tickets. Gaming tickets typically comprise a cardboard or paper substrate printed with the win/loss status and a layer of metalized, opaque overprinting covering the printed win/loss status. The player, after purchasing the ticket, must remove the metalized coating by scraping the metalized coating with a coin or the like to reveal the status. This is an inconvenient and messy process. Thus, there is a need for opaque temporary marking for concealing information printed on documents such as gaming tickets.

Still another example of the need for temporary printing is in the marking of terrain and structures such as roadways, signs, sidewalks, trees, and buildings, to provide a variety of messages such as hazard warnings and directions. Such markings are typically made with paint or chalk directly on the surface of the terrain or structure or by painted signs mounted on or near the terrain or structure. Changing or removing the marking requires either removing the sign or removing the direct marking by washing, abrasion, or chemical attack. These conventional methods of temporary marking are costly and inconvenient and can damage the marked substrate. Thus, there is a need for a more convenient and less destructive means of temporarily marking terrain and structures.

Yet another example of the need for temporary printing is in the underlining or highlighting of text in books or other publications. This task is typically performed with conventional markers such as pens, pencils, highlighters, and felt tip markers. However, these types of markings are not easily removed, and in many cases cannot be removed without damaging the substrate. Thus, there is a need for easily removable marking for underlining or highlighting text.

There is also a desire for a means for indicating exposure to ultraviolet radiation which can be hazardous to humans. More particularly, ultraviolet radiation can cause permanent damage to the eyes and skin. For example, arc welders must wear protective gear to prevent exposure to the ultraviolet radiation emitted during arc welding. Accordingly, there is a need for an inexpensive and convenient means for indicating the degree of exposure to ultraviolet radiation.

In addition, there is a need for improved methods for printing articles, particularly printing multicolor images on plastic articles, plastic films, and paper. Conventional methods of printing color images include photography and xerography, both of which are effective, yet problems remain with each method. Photographic printing involves a developing process which is time consuming, costly, and often includes the use or generation of undesirable chemicals. Color xerography, on the other hand, involves the use of multiple toners to produce overlapping color images. It is often difficult to accurately place the individual color images relative to one another and the result is an image that lacks sharpness. Furthermore, contoured and glossy plastic surfaces are not amenable to conventional methods of marking such as labeling, contact or direct printing, and xerography.

SUMMARY OF THE INVENTION

The present invention address the needs described above by providing a colorant composition which is mutable on exposure to radiation, such as ultraviolet radiation, and stable to natural light such as sunlight and artificial light. The present invention also encompasses several applications of this mutable colorant composition.

More particularly, the mutable colorant composition of the this invention comprises a mutable colorant and a radiation transorber which, upon irradiation with radiation, interacts with the colorant to irreversibly mutate the colorant. In some instances, the colorant, upon irradiation, is rendered substantially colorless so as to become invisible. Desirably, the radiation transorber is an ultraviolet radiation transorber, and the radiation is ultraviolet radiation.

Still more particularly, the ultraviolet irradiation transorber comprises a wavelength-selective sensitizer associated with a photoreactor. The wavelength-selective sensitizer can be covalently coupled to the photoreactor or it can be admixed with the photoreactor. In addition, the mutable colorant composition can further comprise a molecular includant which is associated with the ultraviolet radiation transorber. Suitable molecular includants are clathrates, zeolites, and cyclodextrin. In a particular embodiment, the colorant is at least partially included within a cavity of the molecular includant and the ultraviolet radiation transorber is outside of the cavity. In some instances, the ultraviolet radiation transorber is covalently coupled to the molecular includant.

It is desirable that the ultraviolet radiation transorber absorb ultraviolet radiation at a wavelength of from about 4 to about 400 nanometers. More particularly, it is desirable that the ultraviolet transorber absorb ultraviolet radiation at a wavelength of 125 to 325 nanometers. A particularly suitable form of ultraviolet radiation is incoherent, pulsed ultraviolet radiation emitted from a dielectric barrier discharge excimer lamp.

The present invention further encompasses an erasable price marking for pricing goods comprising a substrate and indicia on the substrate surface visually indicating a price and defined by the mutable colorant composition of the present invention. Upon irradiation with ultraviolet radiation, the ultraviolet radiation transorber of the mutable colorant composition interacts with the colorant to irreversibly mutate the colorant and thereby render the colorant substantially colorless so that the indicia become invisible.

Accordingly, the price on the photoerasable price marking can be instantly erased and changed without removing the substrate. Suitable substrates include labels, tags, tickets, and stickers, and the like. The photoerasable marking allows for marking and unmarking of a product with the price so that retailers can instantly change prices of goods and purchasers can instantly erase a price on a product before giving a product to a recipient.

The present invention also encompasses documents such as gaming tickets for securely communicating concealed information. Such documents comprise a substrate, indicia on the surface of the substrate for communicating a message, and an initially opaque, but photoerasable layer of overprinting on the surface of the substrate covering the message. The overprinting layer comprises the mutable colorant composition of the present invention. Upon irradiation of the overprinting layer with ultraviolet radiation, the ultraviolet radiation transorber interacts with the colorant to irreversibly mutate the colorant and thereby render the colorant substantially colorless so that the overprinting layer becomes invisible and the message is revealed. This allows for convenient communication of concealed information and easy removal of the overprinting.

The present invention further encompasses a photoerasable paint for temporarily marking substrates such as terrain and structures including signs, roads, sidewalks, and buildings. The photoerasable paint comprises a colorant vehicle, which is substantially transparent to ultraviolet radiation, and the mutable colorant composition of the present invention. The mutable colorant composition is dispersed in the vehicle and upon irradiation of the paint with ultraviolet radiation, the ultraviolet radiation transorber interacts with the colorant to irreversibly mutate the color and thereby render the colorant substantially colorless. The photoerasable paint vehicle may desirably be a spray paint vehicle. The photoerasable paint may also be in a dry form, in a powder vehicle, for application by sprinkling. The photoerasable paint of the present invention allows for temporary marking of terrain and structures and subsequent unmarking without the use of washing, abrasion, chemical attack, or other destructive methods.

The present invention also encompasses a marking instrument comprising a reservoir, marking fluid disposed in the reservoir, and a marking fluid applicator for depositing the marking fluid from the reservoir onto a writing surface. The marking fluid comprises a vehicle and the mutable colorant composition of the present invention dispersed in the vehicle. Upon irradiation of the marking fluid with ultraviolet radiation, the ultraviolet radiation transorber interacts with the mutable colorant to irreversibly mutate the colorant and thereby render the colorant substantially colorless. Suitable marking instruments include pens, such as ballpoint pens, and wick or felt tip markers such as highlighters and magic markers. The markers can be used in the underlining and highlighting of text. The underlining and highlighting can be subsequently erased by irradiation with ultraviolet radiation. This allows, for example, text books to be resold without underlining or highlighting of the text.

This invention further encompasses an ultraviolet light exposure indicator comprising a substrate and a film on the substrate comprising the mutable colorant composition of the present invention. The film has a mutable colorant density across the area of the film extending from a region having a first amount of mutable colorant to a region having a second amount of mutable colorant greater than the first amount, so that when the indicator is irradiated with a dosage of ultraviolet radiation, the indicator provides an indication of the dosage of ultraviolet radiation to which the indicator is exposed. Desirably, the substrate is an adhesive strip so that the indicator can be conveniently attached to a surface of concern such as an arc welder's helmet. More particularly, the ultraviolet light exposure indicator can further comprise indicia on the substrate, or on the film, extending along the film and corresponding to the colorant density gradient so that when the indicator is irradiated with a dosage of ultraviolet radiation, the indicia can provide a quantitative indication of the dosage of ultraviolet radiation to which the indicator is exposed.

The present invention also encompasses colored articles for printing and methods for printing articles. The colored article of the present invention includes a substrate comprising a matrix and the mutable colorant composition of the present invention dispersed in or on the matrix. Desirably, the mutable colorant composition is in the matrix when the matrix is a polymer. Upon irradiating selected portions of the substrate with ultraviolet radiation at a dosage level sufficient to irreversibly mutable the colorant at the selected portions, an image can be printed on the substrate. Suitable articles include a variety of items such as plastic containers, plastic films, and paper. Contoured or glossy plastic containers are particularly suitable articles, as are transparent films for use in making transparencies or slides for visual projection. Suitable substrates include the article itself or a film adhered or otherwise attached to the article. Suitable matrix materials include the polymer of the plastic container or film or can be paper when the substrate is a sheet of paper. The matrix should transmit a sufficient amount of ultraviolet light for mutation of the colorant.

In one particular embodiment, the colored article can comprise a plastic substrate including a first polymer and a plastic first film laminated to the substrate and comprising a second polymer, which transmits ultraviolet radiation, and the mutable colorant composition of the present invention dispersed in the second polymer. Upon irradiating selected portions of the first film with ultraviolet radiation at a dosage level sufficient to irreversibly mutate the colorant at the selected portions, an image can be printed on the article.

The substrate can also comprise a non-mutable colorant dispersed therein for multicolored printing. Upon irradiation of selection portions of the substrate or film, the mutable color is rendered colorless and the non-mutable colorant remains at the selected portions.

The substrate may further comprise multiple mutable colorant compositions each including a mutable colorant and an ultraviolet radiation transorber. Each mutable colorant has a color and the colors are different from one another before mutation. Each colorant is mutable at different ultraviolet radiation wavelengths. Upon irradiation of selected portions of the substrate with ultraviolet radiation at the different wavelengths and at dosage levels sufficient to irreversibly mutate the colorants, multi-color images can be printed on the articles corresponding to the selected portions.

These and other objects, features and advantages of the present invention will become apparent after a review of the following detailed description of the disclosed embodiments and the appended claims and drawings.

BRIEF DESCRIPTION OF THE FIGURES

FIG. 7 is a plan view of a ballpoint pen cartridge made in accordance with an embodiment of the present invention. The photoerasable ink is illustrated with hidden lines.

FIG. 8 is a plan view of a felt tip maker of the present invention. The wick and fibrous material containing the photoerasable dye are illustrated with hidden lines.

FIG. 9 is a perspective view of an ultraviolet radiation exposure indicator made according to an embodiment of the present invention.

FIG. 14 is an illustration of several 222 nanometer excimer lamps arranged in four parallel columns wherein the twelve numbers represent the locations where twelve intensity measurements were obtained approximately 5.5 centimeters from the excimer lamps.

FIG. 15 is an illustration of several 222 nanometer excimer lamps arranged in four parallel columns wherein the nine numbers represent the locations where nine intensity measurements were obtained approximately 5.5 centimeters from the excimer lamps.

FIG. 16 is an illustration of several 222 nanometer excimer lamps arranged in four parallel columns wherein the location of the number "1" denotes the location where ten intensity measurements were obtained from increasing distances from the lamps at that location. (The measurements and their distances from the lamp are summarized in Table 12.)

DETAILED DESCRIPTION OF THE INVENTION

Figure 1:
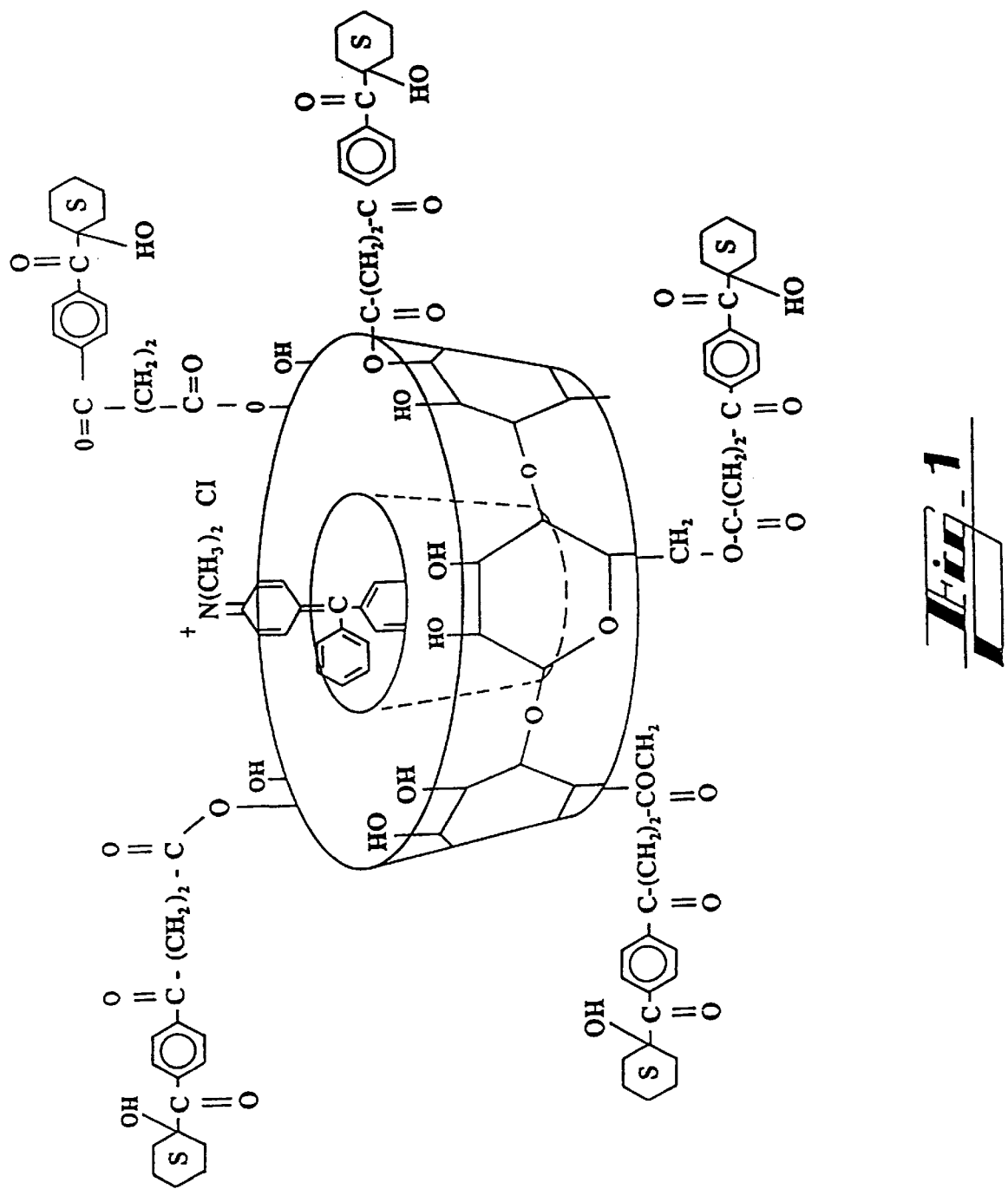
FIG. 1 illustrates an ultraviolet radiation transorber/mutable colorant/molecular includant complex wherein the mutable colorant is malachite green, the ultraviolet radiation transorber is IRGACURE 184 (1-hydroxycyclohexyl phenyl ketone), and the molecular includant is β-cyclodextrin.

The present invention relates in general to applications of an extremely light-stable colorant system that is optionally mutable by exposure to narrow band-width radiation. The colorant composition of the present invention comprises a colorant which, in the presence of a radiation transorber, is stable under ordinary light but is mutable when exposed to specific, narrow band-width radiation. The radiation transorber is capable of absorbing radiation and interacting with the colorant to effect a mutation of the colorant. Optionally, a molecular includant can be included in the composition which provides a more efficient mutable colorant and a colorant more stable to sunlight and artificial light.

More particularly, the composition of the present invention includes a colorant and a radiation transorber. The colorant, in the presence of the radiation transorber, is adapted, upon exposure of the transorber to radiation, desirably ultraviolet radiation, to be mutable. Desirably, the radiation transorber is an ultraviolet radiation transorber. The ultraviolet radiation transorber is adapted to absorb ultraviolet radiation and interact with the colorant to effect the irreversible mutation of the colorant. Unexpectedly, the colorant, in the presence of the ultraviolet radiation transorber, is stable in sunlight or artificial light.

The present invention also relates to colorant compositions having improved stability, wherein the colorant is associated with a modified photoreactor. It has been determined that conventional photoreactors which normally contain a carbonyl group with a functional group on the carbon alpha to the carbonyl group acquire the ability to stabilize colorants when the functional group on the alpha carbon is removed. Accordingly, the present invention also includes a novel method of dehydrating photoreactors that have a hydroxyl group in the alpha position to a carbonyl group.

This reaction is necessary to impart the colorant stabilizing capability to the photoreactor. The novel method of dehydrating photoreactors that have a hydroxyl group in the alpha position to a carbonyl group can be used with a wide variety of photoreactors to provide the colorant stabilizing capability to the photoreactor. The resulting modified photoreactor can optionally be linked to a wavelength-selective sensitizer to impart the capability of decolorizing a colorant when exposed to a predetermined narrow wavelength of electromagnetic radiation. Accordingly, the present invention provides a photoreactor capable of stabilizing a colorant with which it is admixed.

In certain embodiments of the present invention, the colorant and radiation transorber is mutable upon exposure to radiation. In this embodiment, the photoreactor may or may not be modified as described above to impart stability when admixed to a colorant. In one embodiment, an ultraviolet radiation transorber is adapted to absorb ultraviolet radiation and interact with the colorant to effect the irreversible mutation of the colorant. It is desirable that the ultraviolet radiation transorber absorb ultraviolet radiation at a wavelength of from about 4 to about 400 nanometers. If the photoreactor in the radiation transorber is modified as described above, the colorant has improved stability when exposed to sunlight or artificial light.

The present invention also relates to a method of mutating the colorant in the composition of the present invention. The method comprises irradiating a composition containing a mutable colorant and a radiation transorber with radiation at a dosage level sufficient to mutate the colorant.

The present invention further relates to a method of stabilizing a colorant comprising associating the modified photoreactor described above with the colorant. Optionally, the photoreactor may be associated with a wavelength-selective sensitizer, or the photoreactor may be associated with a molecular includant, or both.

After definitions of various terms used herein, the mutable colorant composition of the present invention and method for making that composition are described in detail, then stabilizing compositions are described in detail, followed by a detailed description of particular applications of the mutable colorant composition.

Definitions

The term "composition" and such variations as "colored composition" are used herein to mean a colorant, and a radiation transorber. The radiation transorber may contain any conventional photoreactor or a photoreactor modified as described below. Optionally, the composition may further include a molecular includant. In some embodiments of the present invention, the radiation transorber may contain an aylketoalkene stabilizer as the wavelength-selective sensitizer. When reference is being made to a colored composition which is adapted for a specific application, the term "composition-based" is used as a modifier to indicate that the material includes a colorant, an ultraviolet radiation transorber and, optionally, a molecular includant.

As used herein, the term "colorant" is meant to include, without limitation, any material which, in the presence of a radiation transorber, is adapted upon exposure to specific radiation to be mutable. The colorant typically will be an organic material, such as an organic colorant or pigment. Desirably, the colorant will be substantially transparent to, that is, will not significantly interact with, the ultraviolet radiation to which it is exposed. The term is meant to include a single material or a mixture of two or more materials.

As used herein, the term "irreversible" means that the colorant will not revert to its original color when it no longer is exposed to ultraviolet radiation.

The term "radiation transorber" is used herein to mean any material which is adapted to absorb radiation at a specific wavelength and interact with the colorant to affect the mutation of the colorant and, at the same time, protect the colorant from fading in sunlight or artificial light. The term "ultraviolet radiation transorber" is used herein to mean any material which is adapted to absorb ultraviolet radiation and interact with the colorant to effect the mutation of the colorant. In some embodiments, the ultraviolet radiation transorber may be an organic compound. Where the radiation transorber is comprised of a wavelength-selective sensitizer and a photoreactor, the photoreactor may optionally be modified as described below. Also, the wavelength-selective sensitizer may optionally be the arylketoalkene stabilizer as described below.

The term "compound" is intended to include a single material or a mixture of two or more materials. If two or more materials are employed, it is not necessary that all of them absorb radiation of the same wavelength. As discussed more fully below, a radiation transorber is comprised of a photoreactor and a wavelength selective sensitizer. The radiation transorber has the additional property of making the colorant with which the radiation transorber is associated light stable to sunlight or artificial light.

The term "light-stable" is used herein to mean that the colorant, when associated with the radiation transorber or modified photoreactor or arylketoalkene stabilizer molecule, is more stable to light, including, but not limited to, sunlight or artificial light, than when the colorant is not associated with these compounds.

The term "molecular includant," as used herein, is intended to mean any substance having a chemical structure which defines at least one cavity. That is, the molecular includant is a cavity-containing structure. As used herein, the term "cavity" is meant to include any opening or space of a size sufficient to accept at least a portion of one or both of the colorant and the ultraviolet radiation transorber.

The term "functionalized molecular includant" is used herein to mean a molecular includant to which one or more molecules of an ultraviolet radiation transorber or modified photoreactor or arylketoalkene stabilizer are covalently coupled to each molecule of the molecular includant. The term "degree of substitution" is used herein to refer to the number of these molecules or leaving groups (defined below) which are covalently coupled to each molecule of the molecular includant.

The term "derivatized molecular includant" is used herein to mean a molecular includant having more than two leaving groups covalently coupled to each molecule of molecular includant. The term "leaving group" is used herein to mean any leaving group capable of participating in a bimolecular nucleophilic substitution reaction.

The term "artificial light" is used herein to mean light having a relatively broad bandwidth that is produced from conventional light sources, including, but not limited to, conventional incandescent light bulbs and fluorescent light bulbs.

The term "ultraviolet radiation" is used herein to mean electromagnetic radiation having wavelengths in the range of from about 4 to about 400 nanometers. The especially desirable ultraviolet radiation range for the present invention is between approximately 100 to 375 nanometers. Thus, the term includes the regions commonly referred to as ultraviolet and vacuum ultraviolet. The wavelength ranges typically assigned to these two regions are from about 180 to about 400 nanometers and from about 100 to about 180 nanometers, respectively.

The term "thereon" is used herein to mean thereon or therein. For example, the present invention includes a substrate having a colored composition thereon. According to the definition of "thereon" the colored composition may be present on the substrate or it may be in the substrate.

The term "mutable," with reference to the colorant, is used to mean that the absorption maximum of the colorant in the visible region of the electromagnetic spectrum is capable of being mutated or changed by exposure to radiation, preferably ultraviolet radiation, when in the presence of the radiation transorber. In general, it is only necessary that such absorption maximum be mutated to an absorption maximum which is different from that of the colorant prior to exposure to the ultraviolet radiation, and that the mutation be irreversible. Thus, the new absorption maximum can be within or outside of the visible region of the electromagnetic spectrum. In other words, the colorant can mutate to a different color or be rendered colorless. The latter is also desirable when the colorant is used in data processing forms for use with photo-sensing apparatus that detect the presence of indicia at indicia-receiving locations of the form.

Functionalized Molecular Includant

In several embodiments, the radiation transorber molecule, the wavelength-selective sensitizer, the photoreactor, or the arylketoalkene stabilizer may be associated with a molecular includant. It is to be noted that in all the formulas, the number of such molecules can be between approximately 1 and approximately 21 molecules per molecular includant. Of course, in certain situations, there can be more than 21 molecules per molecular includant molecule. Desirably, there are more than three of such molecules per molecular includant.

The degree of substitution of the functionalized molecular includant may be in a range of from 1 to approximately 21. As another example, the degree of substitution may be in a range of from 3 to about 10. As a further example, the degree of substitution may be in a range of from about 4 to about 9.

The colorant is associated with the functionalized molecular includant. The term "associated" in its broadest sense means that the colorant is at least in close proximity to the functionalized molecular includant. For example, the colorant may be maintained in close proximity to the functionalized molecular includant by hydrogen bonding, van der Waals forces, or the like. Alternatively, the colorant may be covalently bonded to the functionalized molecular includant, although this normally is neither desired nor necessary. As a further example, the colorant may be at least partially included within the cavity of the functionalized molecular includant.

The examples below disclose methods of preparing and associating these colorants and ultraviolet radiation transorbers to beta-cyclodextrins. For illustrative purposes only, Examples 1, 2, 6, and 7 disclose one or more methods of preparing and associating colorants and ultraviolet radiation transorbers to cyclodextrins.

In those embodiments of the present invention in which the ultraviolet radiation transorber is covalently coupled to the molecular includant, the efficiency of energy transfer from the ultraviolet radiation transorber to the colorant is, at least in part, a function of the number of ultraviolet radiation transorber molecules which are attached to the molecular includant. It now is known that the synthetic methods described above result in covalently coupling an average of two transorber molecules to each molecule of the molecular includant. Because the time required to mutate the colorant should, at least in part, be a function of the number of ultraviolet radiation transorber molecules coupled to each molecule of molecular includant, there is a need for an improved colored composition in which an average of more than two ultraviolet radiation transorber molecules are covalently coupled to each molecule of the molecular includant.

Accordingly, the present invention also relates to a composition which includes a colorant and a functionalized molecular includant. For illustrative purposes only, Examples 12 through 19, and 21 through 22 disclose other methods of preparing and associating colorants and ultraviolet radiation transorbers to cyclodextrins, wherein more than two molecules of the ultraviolet radiation transorber are covalently coupled to each molecule of the molecular includant. Further, Examples 29 and 31 disclose methods of preparing and associating arylketoalkene stabilizers with cyclodextrin, wherein the cyclodextrin has an average of approximately 3 or 4 stabilizer molecules attached thereto.

The present invention also provides a method of making a functionalized molecular includant. The method of making a functionalized molecular includant involves the steps of providing a derivatized ultraviolet radiation transorber having a nucleophilic group, providing a derivatized molecular includant having more than two leaving groups per molecule, and reacting the derivatized ultraviolet radiation transorber with the derivatized molecular includant under conditions sufficient to result in the covalent coupling of an average of more than two ultraviolet radiation transorber molecules to each molecular includant molecule. By way of example, the derivatized ultraviolet radiation transorber may be 2-[p-(2-methyl-2-mercaptomethylpropionyl)phenoxy] ethyl 1,3-dioxo-2-isoindoline-acetate. As another example, the derivatized ultraviolet radiation transorber may be 2-mercaptomethyl-2-methyl-4'-[2-[p-(3-oxobutyl)phenoxy] ethoxy]propiophenone.

In general, the derivatized ultraviolet radiation transorber and the derivatized molecular includant are selected to cause the covalent coupling of the ultraviolet radiation transorber to the molecular includant by means of a bimolecular nucleophilic substitution reaction. Consequently, the choice of the nucleophilic group and the leaving groups and the preparation of the derivatized ultraviolet radiation transorber and derivatized molecular includant, respectively, may be readily accomplished by those having ordinary skill in the art without the need for undue experimentation.

The nucleophilic group of the derivatized ultraviolet radiation transorber may be any nucleophilic group capable of participating in a bimolecular nucleophilic substitution reaction, provided, of course, that the reaction results in the covalent coupling of more than two molecules of the ultraviolet radiation transorber to the molecular includant. The nucleophilic group generally will be a Lewis base, i.e., any group having an unshared pair of electrons. The group may be neutral or negatively charged. Examples of nucleophilic groups include, by way of illustration only, aliphatic hydroxy, aromatic hydroxy, alkoxides, carboxy, carboxylate, amino, and mercapto.

Similarly, the leaving group of the derivatized molecular includant may be any leaving group capable of participating in a bimolecular nucleophilic substitution reaction, again provided that the reaction results in the covalent coupling of more than two molecules of the ultraviolet radiation transorber to the molecular includant. Examples of leaving groups include, also by way of illustration only, p-toluenesulfonates (tosylates), p-bromobenzenesulfonates (brosylates), p-nitrobenzenesulfonates (nosylates), methanesulfonates (mesylates), oxonium ions, alkyl perchlorates, ammonioalkane sulfonate esters (betylates), alkyl fluorosulfonates, trifluoromethanesulfonates (triflates), nonafluorobutanesulfonates (nonaflates), and 2,2,2-trifluoroethanesulfonates (tresylates).

The reaction of the derivatized ultraviolet radiation transorber with the derivatized molecular includant is carried out in solution. The choice of solvent depends upon the solubilities of the two derivatized species. As a practical matter, a particularly useful solvent is N,N-dimethylformamide (DMF).

The reaction conditions, such as temperature, reaction time, and the like generally are matters of choice based upon the natures of the nucleophilic and leaving groups. Elevated temperatures usually are not required. For example, the reaction temperature may be in a range of from about 0°C. to around ambient temperature, i.e., to 20°–25° C.

The preparation of the functionalized molecular includant as described above generally is carried out in the absence of the colorant. However, the colorant may be associated with the derivatized molecular includant before reacting the derivatized ultraviolet radiation transorber with the derivatized molecular includant, particularly if a degree of substitution greater than about three is desired. When the degree of substitution is about three, it is believed that the association of the colorant with the functionalized molecular includant still may permit the colorant to be at least partially included in a cavity of the functionalized molecular includant. At higher degrees of substitution, such as about six, steric hindrance may partially or completely prevent the colorant from being at least partially included in a cavity of the functionalized molecular includant. Consequently, the colorant may be associated with the derivatized molecular includant which normally will exhibit little, if any, steric hindrance. In this instance, the colorant will be at least partially included in a cavity of the derivatized molecular includant. The above-described bimolecular nucleophilic substitution reaction then may be carried out to give a colored composition of the present invention in which the colorant is at least partially included in a cavity of the functionalized molecular includant.

Mutable Composition

As stated above, the present invention provides compositions comprising a colorant which, in the presence of a radiation transorber, is mutable when exposed to a specific wavelength of radiation, while at the same time, provides light stability to the colorant with respect to sunlight and artificial light. Desirably, the mutated colorant will be stable, i.e., not appreciably adversely affected by radiation normally encountered in the environment, such as natural or artificial light and heat. Thus, desirably, a colorant rendered colorless will remain colorless indefinitely.

The dye, for example, may be an organic dye. Organic dye classes include, by way of illustration only, triarylmethyl dyes, such as Malachite Green Carbinol base {4-(dimethylamino)-α-[4-(dimethylamino)phenyl]-α-phenylbenzene-methanol}, Malachite Green Carbinol hydrochloride {N-4-[[4-(dimethylamino)phenyl]phenylmethylene]-2,5-cyclohexylidene-1-ylidene]-N-methyl-methanaminium chloride or bis[p-(dimethylamino)phenyl]phenylmethylium chloride}, and Malachite Green oxalate {N-4-[[4-(dimethylamino)phenyl]phenylmethylene]-2,5-cyclohexyldien-1-ylidene]-N-methylmethanaminium chloride or bis[p-(dimethyl-amino)phenyl]phenylmethylium oxalate}; monoazo dyes, such as Cyanine Black, Chrysoidine [Basic Orange 2; 4-(phenylazo)-1,3-benzenediamine monohydrochloride], Victoria Pure Blue BO, Victoria Pure Blue B, basic fuschin and β-Naphthol Orange; thiazine dyes, such as Methylene Green, zinc chloride double salt [3,7-bis(dimethylamino)-6-nitrophenothiazin-5-ium chloride, zinc chloride double salt]; oxazine dyes, such as Lumichrome (7,8-dimethylalloxazine); naphthalimide dyes, such as Lucifer Yellow CH {6-amino-2-[(hydrazinocarbonyl)amino]-2,3-dihydro-1,3-dioxo-1H-benz[de]isoquinoline-5,8-disulfonic acid dilithium salt}; azine dyes, such as Janus Green B {3-(diethylamino)-7-[[4-(dimethylamino)phenyl]azo]-5-phenylphenazinium chloride}; cyanine dyes, such as Indocyanine Green {Cardio-Green or Fox Green; 2-[7-[1,3-dihydro-1,1-dimethyl-3-(4-sulfobutyl)-2H-benz[e]indol-2-ylidene]-1,3,5-heptatrienyl]-1,1-dimethyl-3-(4-sulfobutyl)-1H-benz[e]indolium hydroxide inner salt sodium salt}; indigo dyes, such as Indigo {Indigo Blue or Vat Blue 1; 2-(1,3-dihydro-3-oxo-2H-indol-2-ylidene)-1,2-dihydro-3H-indol-3-one}; coumarin dyes, such as 7-hydroxy-4-methylcoumarin (4-methylumbelliferone); benzimidazole dyes, such as Hoechst 33258 [bisbenzimide or 2-(4-hydroxyphenyl)-5-(4-methyl-1-pipera-zinyl)-2,5-bi-1H-benzimidazole trihydrochloride pentahydrate]; paraquinoidal dyes, such as Hematoxylin {Natural Black 1; 7,11b-dihydrobenz[b]indeno[1,2-d]pyran-3,4,6a,9,10(6H)-pentol}; fluorescein dyes, such as Fluoresceinamine (5-aminofluorescein); diazonium salt dyes, such as Diazo Red RC (Azoic Diazo No. 10 or Fast Red RC salt; 2-methoxy-5-chlorobenzenediazonium chloride, zinc chloride double salt); azoic diazo dyes, such as Fast Blue BB salt (Azoic Diazo No. 20; 4-benzoylamino-2,5-diethoxybenzene diazonium chloride, zinc chloride double salt); phenylenediamine dyes, such as Disperse Yellow 9 [N-(2,4-dinitrophenyl)-1,4-phenylenediamine or Solvent Orange 53]; diazo dyes, such as Disperse Orange 13 [Solvent Orange 52; 1-phenylazo-4-(4hydroxyphenylazo)naphthalene]; anthraquinone dyes, such as Disperse Blue 3 [Celliton Fast Blue FFR; 1-methylamino-4-(2-hydroxyethylamino)-9,10-anthraquinone], Disperse Blue 14 [Celliton Fast Blue B; 1,4-bis(methylamino)-9,10-anthraquinone], and Alizarin Blue Black B (Mordant Black 13); trisazo dyes, such as Direct Blue 71 {Benzo Light Blue FFL or Sirius Light Blue BRR; 3-[(4-[(4-[(6-amino-1-hydroxy-3-sulfo-2-naphthalenyl)azo]-6-sulfo-1-naphthalenyl)azo]-1-naphthalenyl)azo]-1,5-naphthalenedisulfonic acid tetrasodium salt}; xanthene dyes, such as 2,7-dichlorofluorescein; proflavine dyes, such as 3,6-diaminoacridine hemisulfate (Proflavine); sulfonaphthalein dyes, such as Cresol Red (o-cresolsulfonaphthalein); phthalocyanine dyes, such as Copper Phthalocyanine {Pigment Blue 15; (SP-4-1)-[29H,31H-phthalocyanato(2-)-$N^{29}$, $N^{30}$,$N^{31}$,$N^{32}$]copper}; carotenoid dyes, such as trans-β-carotene (Food Orange 5); carminic acid dyes, such as Carmine, the aluminum or calcium-aluminum lake of carminic acid (7-a-D-glucopyranosyl-9,10-dihydro-3,5,6,8-tetrahydroxy-1-methyl-9,10-dioxo-2-anthracenecarbonylic acid); azure dyes, such as Azure A [3-amino-7-(dimethylamino)phenothiazin-5-ium chloride or 7-(dimethylamino)-3-imino-3H-phenothiazine hydrochloride]; and acridine dyes, such as Acridine Orange [Basic Orange 14; 3,8-bis(dimethylamino)acridine hydrochloride, zinc chloride double salt] and Acriflavine (Acriflavine neutral; 3,6-diamino-10-methylacridinium chloride mixture with 3,6-acridinediamine).

The present invention includes unique compounds, namely, radiation transorbers, that are capable of absorbing narrow ultraviolet wavelength radiation, while at the same time, imparting light-stability to a colorant with which the compounds are associated. The compounds are synthesized by combining a wavelength-selective sensitizer and a photoreactor. The photoreactors oftentimes do not efficiently absorb high energy radiation. When combined with the wavelength-selective sensitizer, the resulting compound is a wavelength specific compound that efficiently absorbs a very narrow spectrum of radiation. The wavelength-selective sensitizer may be covalently coupled to the photoreactor.

By way of example, the wavelength-selective sensitizer may be selected from the group consisting of phthaloylglycine and 4-(4-oxyphenyl)-2-butanone. As another example, the photoreactor may be selected from the group consisting of 1-[4-(2-hydroxyethoxy)phenyl )-2-hydroxy-2-methylpropan-1-one and cyclohexyl-phenyl ketone ester. Other photoreactors are listed by way of example, in the detailed description below regarding the improved stabilized composition of the present invention. As a further example, the ultraviolet radiation transorber may be 2-[p-2-methyllactoyl)phenoxy]ethyl 1,3-dioxo-2-isoindolineacetate. As still another example, the ultraviolet radiation transorber may be 2-hydroxy-2-methyl-4'-2-[p-(3-oxobutyl)phenoxy]propiophenone.

Although the colorant and the ultraviolet radiation transorber have been described as separate compounds, they can be part of the same molecule. For example, they can be covalently coupled to each other, either directly, or indirectly through a relatively small molecule, or spacer. Alternatively, the colorant and ultraviolet radiation transorber can be covalently coupled to a large molecule, such as an oligomer or a polymer. Further, the colorant and ultraviolet radiation transorber may be associated with a large molecule by van der Waals forces, and hydrogen bonding, among other means. Other variations will be readily apparent to those having ordinary skill in the art.

For example, in an embodiment of the composition of the present invention, the composition further comprises a molecular includant. Thus, the cavity in the molecular includant can be a tunnel through the molecular includant or a cave-like space or a dented-in space in the molecular includant. The cavity can be isolated or independent, or connected to one or more other cavities.

The molecular includant can be inorganic or organic in nature. In certain embodiments, the chemical structure of the molecular includant is adapted to form a molecular inclusion complex. Examples of molecular includants are, by way of illustration only, clathrates or intercalates, zeolites, and cyclodextrins. Examples of cyclodextrins include, but are not limited to, alpha-cyclodextrin, beta-cyclodextrin, gamma-cyclodextrin, hydroxypropyl beta-cyclodextrin, hydroxyethyl beta-cyclodextrin, sulfated beta-cyclodextrin, hydroxyethyl alpha cyclodextrin, carboxymethyle alpha cyclodextrin, carboxymethyl beta cyclodextrin, carboxymethyl gamma cyclodextrin, octyl succinated alpha cyclodextrin, octyl succinated beta cyclodextrin, octyl succinated gamma cyclodextrin and sulfated beta and gamma-cyclodextrin (American Maize-Products Company, Hammond, Ind.).

Desirably, the composition of the present invention includes a molecular includant. The desired molecular includant is a cyclodextrin. More particularly, in some embodiments, the molecular includant is an alpha-cyclodextrin. In other embodiments, the molecular includant is a beta-cyclodextrin. Although not wanting to be bound by the following theory, it is believed that the closer the transorber molecule is to the mutable colorant on the molecular includant, the more efficient the interaction with the colorant to effect mutation of the colorant. Thus, the molecular includant with functional groups that can react with and bind the transorber molecule and that are close to the binding site of the mutable colorant are the more desirable molecular includants.

In some embodiments, the colorant and the ultraviolet radiation transorber are associated with the molecular includant. The term "associated", in its broadest sense, means that the colorant and the ultraviolet radiation transorber are at least in close proximity to the molecular includant. For example, the colorant and/or the ultraviolet radiation transorber can be maintained in close proximity to the molecular includant by hydrogen bonding, van der Waals forces, or the like. Alternatively, either or both of the colorant and the ultraviolet radiation transorber can be covalendy bonded to the molecular includant. In certain embodiments, the colorant will be associated with the molecular includant by means of hydrogen bonding and/or van der Waals forces or the like, while the ultraviolet radiation transorber is covalently bonded to the molecular includant. In other embodiments, the colorant is at least partially included within the cavity of the molecular includant, and the ultraviolet radiation transorber is located outside of the cavity of the molecular includant.

In one embodiment wherein the colorant and the ultraviolet radiation transorber are associated with the molecular includant, the colorant is crystal violet, the ultraviolet radiation transorber is a dehydrated phthaloylglycine-2959, and the molecular includant is beta-cyclodextrin. In yet another embodiment wherein the colorant and the ultraviolet radiation transorber are associated with the molecular includant, the colorant is crystal violet, the ultraviolet radiation transorber is 4(4-hydroxyphenyl) butan-2-one-2959 (chloro substituted), and the molecular includant is beta-cyclodextrin.

Figure 2:
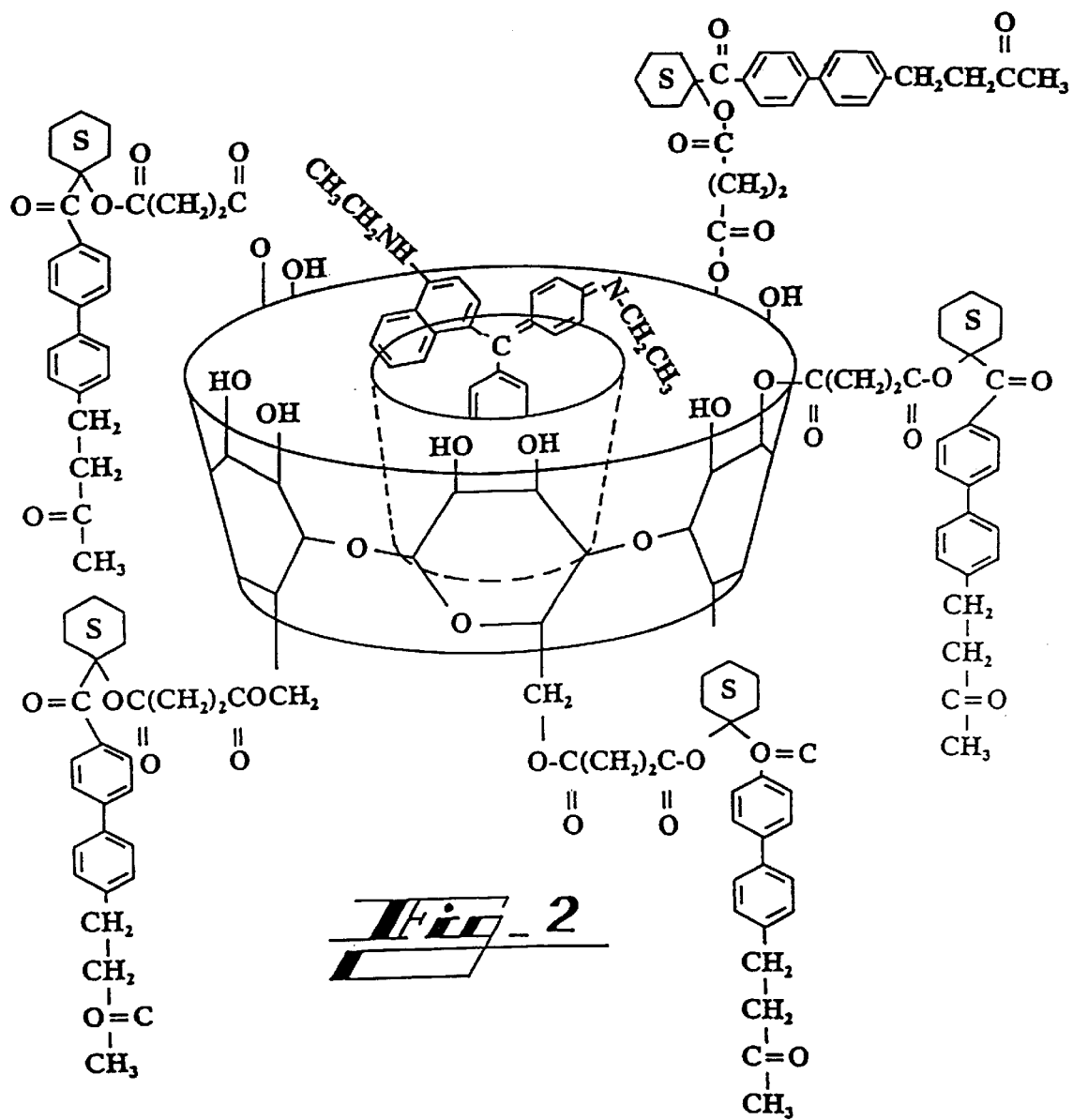
FIG. 2 illustrates an ultraviolet radiation transorber/mutable colorant/molecular includant complex wherein the mutable colorant is Victoria Pure Blue BO (Basic Blue 7), the ultraviolet radiation transorber is IRGACURE 184 (1-hydroxycyclohexyl phenyl ketone), and the molecular includant is β-cyclodextrin.

In another embodiment wherein the colorant and the ultraviolet radiation transorber are associated with the molecular includant, the colorant is malachite green, the ultraviolet radiation transorber is IRGACURE 184, and the molecular includant is beta-cyclodextrin as shown in FIG. 1. In still another embodiment wherein the colorant and the ultraviolet radiation transorber are associated with the molecular includant, the colorant is Victoria Pure Blue BO, the ultraviolet radiation transorber is IRGACURE 184, and the molecular includant is beta-cyclodextrin as shown in FIG. 2.

The present invention also relates to a method of mutating the colorant in the composition of the present invention. Briefly described, the method comprises irradiating a composition containing a mutable colorant and a radiation transorber with radiation at a dosage level sufficient to mutate the colorant. As stated above, in one embodiment the composition further includes f a molecular includant. In another embodiment, the composition is applied to a substrate before being irradiated with ultraviolet radiation.

The composition of the present invention may be irradiated with radiation having a wavelength of between about 4 to about 1,000 nanometers. The radiation to which the composition of the present invention is exposed generally will have a wavelength of from about 4 to about 1,000 nanometers. Thus, the radiation may be ultraviolet radiation, including near ultraviolet and far or vacuum ultraviolet radiation; visible radiation; and near infrared radiation. Desirably, the composition is irradiated with radiation having a wavelength of from about 4 to about 700 nanometers. More desirably, the composition of the present invention is irradiated with ultraviolet radiation having a wavelength of from about 4 to about 400 nanometers. It is more desirable that the radiation has a wavelength of between about 100 to 375 nanometers.

Especially desirable radiation is incoherent, pulsed ultraviolet radiation produced by a dielectric barrier discharge lamp. Even more preferably, the dielectric barrier discharge lamp produces radiation having a narrow bandwidth, i.e., the half width is of the order of approximately 5 to 100 nanometers. Desirably, the radiation will have a half width of the order of approximately 5 to 50 nanometers, and more desirably will have a half width of the order of 5 to 25 nanometers. Most desirably, the half width will be of the order of approximately 5 to 15 nanometers.

The amount or dosage level of ultraviolet radiation that the colorant of the present invention is exposed to will generally be that amount which is necessary to mutate the colorant. The amount of ultraviolet radiation necessary to mutate the colorant can be determined by one of ordinary skill in the art using routine experimentation. Power density is the measure of the amount of radiated electromagnetic power traversing a unit area and is usually expressed in watts per centimeter squared ($W/cm^2$). The power density level range is between approximately 5 $mW/cm^2$ and 15 $mW/cm^2$, more particularly 8 to 10 mW/ c level, in turn, typically is a function of the time of exposure and the intensity or flux of the radiation source which irradiates the colored composition. The latter is affected by the distance of the composition from the source and, depending upon the wavelength range of the ultraviolet radiation, can be affected by the atmosphere between the radiation source and the composition. Accordingly, in some instances it may be appropriate to expose the composition to the radiation in a controlled atmosphere or in a vacuum, although in general neither approach is desired.

With regard to the mutation properties of the present invention, photochemical processes involve the absorption of light quanta, or photons, by a molecule, e.g., the ultraviolet radiation transorber, to produce a highly reactive electronically excited state. However, the photon energy, which is proportional to the wavelength of the radiation, cannot be absorbed by the molecule unless it matches the energy difference between the unexcited, or original, state and an excited state. Consequently, while the wavelength range of the ultraviolet radiation to which the colored composition is exposed is not directly of concern, at least a portion of the radiation must have wavelengths which will provide the necessary energy to raise the ultraviolet radiation transorber to an energy level which is capable of interacting with the colorant.

It follows, then, that the absorption maximum of the ultraviolet radiation transorber ideally will be matched with the wavelength range of the ultraviolet radiation to increase the efficiency of the mutation of the colorant. Such efficiency also will be increased if the wavelength range of the ultraviolet radiation is relatively narrow, with the maximum of the ultraviolet radiation transorber coming within such range. For these reasons, especially suitable ultraviolet radiation has a wavelength of from about 100 to about 375 nanometers. Ultraviolet radiation within this range desirably may be incoherent, pulsed ultraviolet radiation from a dielectric barrier discharge excimer lamp.

The term "incoherent, pulsed ultraviolet radiation" has reference to the radiation produced by a dielectric barrier discharge excimer lamp (referred to hereinafter as "excimer lamp"). Such a lamp is described, for example, by U. Kogelschatz, "Silent discharges for the generation of ultraviolet and vacuum ultraviolet excimer radiation," Pure & Appl. Chem., 62, No. 9, pp. 1667–1674 (1990); and E. Eliasson and U. Kogelschatz, "UV Excimer Radiation from Dielectric-Barrier Discharges," Appl. Phys. B, 46, pp. 299–303 (1988). Excimer lamps were developed originally by ABB Infocom Ltd., Lenzburg, Switzerland. The excimer lamp technology since has been acquired by Haräus Noblelight AG, Hanau, Germany.

The excimer lamp emits radiation having a very narrow bandwidth, i.e., radiation in which the half width is of the order of 5–15 nanometers. This emitted radiation is incoherent and pulsed, the frequency of the pulses being dependent upon the frequency of the alternating current power supply which typically is in the range of from about 20 to about 300 kHz. An excimer lamp typically is identified or referred to by the wavelength at which the maximum intensity of the radiation occurs, which convention is followed throughout this specification. Thus, in comparison with most other commercially useful sources of ultraviolet radiation which typically emit over the entire ultraviolet spectrum and even into the visible region, excimer lamp radiation is substantially monochromatic.

Excimers are unstable molecular complexes which occur only under extreme conditions, such as those temporarily existing in special types of gas discharge. Typical examples are the molecular bonds between two rare gaseous atoms or between a rare gas atom and a halogen atom. Excimer complexes dissociate within less than a microsecond and, while they are dissociating, release their binding energy in the form of ultraviolet radiation. Known excimers, in general, emit in the range of from about 125 to about 360 nanometers, depending upon the excimer gas mixture.

For example, in one embodiment, the colorant of the present invention is mutated by exposure to 222 nanometer excimer lamps. More particularly, the colorant crystal violet is mutated by exposure to 222 nanometer lamps. Even more particularly, the colorant crystal violet is mutated by exposure to 222 nanometer excimer lamps located approximately 5 to 6 centimeters from the colorant, wherein the lamps are arranged in four parallel columns approximately 30 centimeters long. It is to be understood that the arrangement of the lamps is not critical to this aspect of the invention. Accordingly, one or more lamps may be arranged in any configuration and at any distance which results in the colorant mutating upon exposure to the lamp's ultraviolet radiation. One of ordinary skill in the art would be able to determine by routine experimentation which configurations and which distances are appropriate. Also, it is to be understood that different excimer lamps are to be used with different ultraviolet radiation transorbers. The excimer lamp used to mutate a colorant associated with an ultraviolet radiation transorber should produce ultraviolet radiation of a wavelength that is absorbed by the ultraviolet radiation transorber.

In some embodiments, the molar ratio of ultraviolet radiation transorber to colorant generally will be equal to or greater than about 0.5. As a general rule, the more efficient the ultraviolet radiation transorber is in absorbing the ultraviolet radiation and interacting with, i.e., transferring absorbed energy to, the colorant to effect irreversible mutation of the colorant, the lower such ratio can be. Current theories of molecular photo chemistry suggest that the lower limit to such ratio is 0.5, based on the generation of two free radicals per photon. As a practical matter, however, ratios higher than 1 are likely to be required, perhaps as high as about 10. However, the present invention is not bound by any specific molar ratio range. The important feature is that the transorber is present in an amount sufficient to effect mutation of the colorant.

While the mechanism of the interaction of the ultraviolet radiation transorber with the colorant is not totally understood, it is believed that it may interact with the colorant in a variety of ways. For example, the ultraviolet radiation transorber, upon absorbing ultraviolet radiation, may be converted to one or more free radicals which interact with the colorant. Such free radical-generating compounds typically are hindered ketones, some examples of which include, but are not limited to: benzildimethyl ketal (available commercially as IRGACURE 651, Ciba-Geigy Corporation, Hawthorne, N.Y.); 1-hydroxycyclohexyl phenyl ketone (IRGACURE 500); 2-methyl-1-[4-(methylthio)phenyl]-2-morpholino-propan-1-one](IRGACURE 907); 2-benzyl-2-dimethylamino-1-(4-morpholinophenyl)butan-1-one (IRGACURE 369); and 1-hydroxycyclohexyl phenyl ketone (IRGACURE 184).

Alternatively, the ultraviolet radiation may initiate an electron transfer or reduction-oxidation reaction between the ultraviolet radiation transorber and the colorant. In this case, the ultraviolet radiation transorber may be, but is not limited to, Michler's ketone (p-dimethylaminophenyl ketone) or benzyl trimethyl stannate. Or, a cationic mechanism may be involved, in which case the ultraviolet radiation transorber can be, for example, bis[4-(diphenylsulphonio)phenyl]] sulfide bis-(hexafluorophosphate) (Degacure KI85, Ciba-Geigy Corporation, Hawthorne, N.Y.); Cyracure UVI-6990 (Ciba-Geigy Corporation), which is a mixture of bis[4-(diphenylsulphonio)phenyl] sulfide bis (hexafluorophosphate) with related monosulphonium hexafluorophosphate salts; and n5-2,4-(cyclopentadienyl)[1,2,3,4,5,6-n-(methylethyl)benzene]-iron(II) hexafluorophosphate (IRGACURE 261).

Stabilizing Compositions

With regard to the light stabilizing activity of the present invention, it has been determined that in some embodiments it is necessary to modify a conventional photoreactor to produce the improved light stable composition of the present invention. The simplest form of the improved light stable composition of the present invention includes a colorant admixed with a photoreactor modified as described below. The modified photoreactor may or may not be combined with a wavelength-selective sensitizer. Many conventional photoreactor molecules have a functional group that is alpha to a carbonyl group. The functional group includes, but is not limited to, hydroxyl groups, ether groups, ketone groups, and phenyl groups.

For example, a preferred radiation transorber that can be used in the present invention is designated phthaloylglycine-2959 and is represented by the following formula:

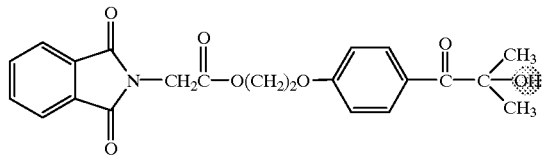

The photoreactor portion of the ultraviolet radiation transorber has a hydroxyl group (shaded portion) alpha to the carbonyl carbon. The above molecule does not light-stabilize a colorant. However, the hydroxyl group can be removed by dehydration (see Examples 4 and 5) yielding the compound represented by the following formula:

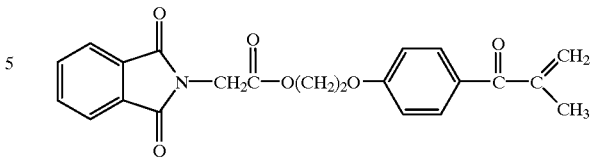

This dehydrated phthaloylglycine-2959 is capable of light-stabilizing a colorant. Thus, it is believed that removal of the functional group alpha to the carbonyl carbon on any photoreactor molecule will impart the light-stabilizing capability to the molecule. While the dehydrated ultraviolet radiation transorber can impart light-stability to a colorant simply by mixing the molecule with the colorant, it has been found that the molecule is much more efficient at stabilizing colorants when it is attached to an includant, such as cyclodextrin, as described herein.

It is to be understood that stabilization of a colorant can be accomplished according to the present invention by utilizing only the modified photoreactor. In other words, a modified photoreactor without a wavelength selective sensitizer may be used to stabilize a colorant. An example of a photoreactor that is modified according to the present invention is DARCUR 2959. The unmodified DARCUR 2959 and the dehydrated DARCUR 2959 are represented by the following formula:

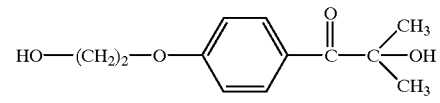

Unmodified DARCUR 2959®

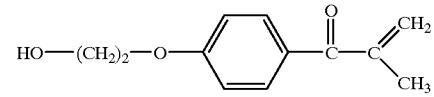

Dehydrated DARCUR 2959®

Other photoreactors can be modified according to the present invention to provide stabilizers for dyes. These photoreactors include, but are not limited to: 1-Hydroxy-cyclohexyl-phenyl ketone ("HCPK") (IRGACURE 184, Ciba-Geigy); α,α-dimethoxy-α-hydroxy acetophenone (DAROCUR 1173, Merck); 1 -(4-Isopropylphenyl)-2-hydroxy-2-methyl-propan-1-one (DAROCUR 1116, Merck); 1-[4-(2-Hydroxyethoxy)phenyl]-2-hydroxy-2-methyl-propan-1-one (DAROCUR 2959, Merck); Poly[2-hydroxy-2-methyl-1-[4-(1-methylvinyl)phenyl] propan-1-one] (ESACURE KIP, Fratelli Lamberti); Benzoin (2-Hydroxy-1,2-diphenylethanone) (ESACURE BO, Fratelli Lamberti); Benzoin ethyl ether (2-Ethoxy-1,2-diphenylethanone) (DAITOCURE EE, Siber Hegner); Benzoin isopropyl ether (2-Isopropoxy-1,2-diphenylethanone) (VICURE 30, Stauffer); Benzoin n-butyl ether (2-Butoxy-1,2-diphenylethanone) (ESACURE EB1, Fratelli Lamberti); mixture of benzoin butyl ethers (TRIGONAL 14, Akzo); Benzoin iso-butyl ether (2-Isobutoxy-1,2-diphenylethanone) (VICURE 10, Stauffer); blend of benzoin n-butyl ether and benzoin isobutyl ether (ESACURE EB3, ESACURE EB4, Fratelli Lamberti); Benzildimethyl ketal (2,2-Dimethoxy- 1,2-diphenylethanone) ("BDK") (IRGACURE 651, Ciba-Geigy); 2,2-Diethoxy-1,2-diphenylethanone (UVATONE 8302, Upjohn); α,α-

Diethoxyacetophenone (2,2-Diethoxy-1-phenyl-ethanone) ("DEAP", Upjohn), (DEAP, Rahn); and α,α-Di-(n-butoxy)-acetophenone (2,2-Dibutoxyl-1-phenyl-ethanone) (UVATONE 8301, Upjohn).

It is known to those of ordinary skill in the art that the dehydration by conventional means of the tertiary alcohols that are alpha to the carbonyl groups is difficult. One conventional reaction that can be used to dehydrate the phthaloylglycine-2959 is by reacting the phthaloylglycine-2959 in anhydrous benzene in the presence of p-toluenesulfonic acid. After refluxing the mixture, the final product is isolated. However, the yield of the desired dehydrated alcohol is only about 15 to 20% by this method.

To increase the yield of the desired dehydrated phthaloylglycine-2959, a new reaction was invented. The reaction is summarized as follows:

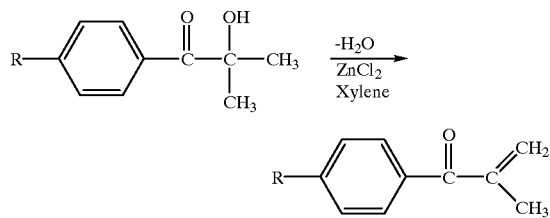

It is to be understood that the groups on the carbon alpha to the carbonyl group can be groups other than methyl groups such as aryl or heterocyclic groups. The only limitation on these groups are steric limitations. Desirably, the metal salt used in the Nohr-MacDonald elimination reaction is $ZnCl_2$. It is to be understood that other transition metal salts can be used in performing the Nohr-MacDonald elimination reaction but $ZnCl_2$ is the preferred metal salt. The amount of metal salt used in the Nohr-MacDonald elimination reaction is preferably approximately equimolar to the tertiary alcohol compound, such as the photoreactor. The concentration of tertiary alcohol in the reaction solution is between approximately 4% and 50% w/v.

Thus, the stabilizing composition produced by the process of dehydrating a tertiary alcohol that is alpha to a carbonyl group on a photoreactor is represented in the following general formula:

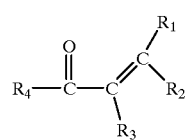

wherein:

$R_1$ is a hydrogen, alkyl, alkenyl, cycloalkyl, heterocycloalkyl, aryl or a heteroaryl group;

$R_2$ is a hydrogen, alkyl, alkenyl, cycloalkyl, heterocycloalkyl, aryl or a heteroaryl group;

$R_3$ is a hydrogen, alkyl, alkenyl, cycloalkyl, heterocycloalkyl, aryl or a heteroaryl group; and $R_4$ is an aryl, heteroaryl, or substituted aryl group.

Another requirement of the reaction is that it be run in a non-aqueous, non-polar solvent. The preferred solvents for running the Nohr-MacDonald elimination reaction are aromatic hydrocarbons including, but not limited to, xylene, benzene, toluene, cumene, mesitylene, I-cymene, butylbenzene, styrene, and divinylbenzene. It is to be understood that other substituted aromatic hydrocarbons can be used as solvents in the present invention. p-Xylene is the preferred aromatic hydrocarbon solvent, but other isomers of xylene can be used in performing the Nohr-MacDonald elimination reaction.

An important requirement in performing the Nohr-MacDonald elimination reaction is that the reaction be run at a relatively high temperature. The reaction is desirably performed at a temperature of between approximately 80° C. and 150° C. A suitable temperature for dehydrating phthaloylglycine-2959 is approximately 124° C. The time the reaction runs is not critical. The reaction should be run between approximately 30 minutes to 4 hours. However, depending upon the reactants and the solvent used, the timing may vary to achieve the desired yield of product.

It is to be understood that the dehydrated phthaloylglycine-2959 can be attached to the molecular includant in a variety of ways. In one embodiment, the dehydrated phthaloylglycine-2959 is covalently attached to the cyclodextrin and is represented by the following formula::

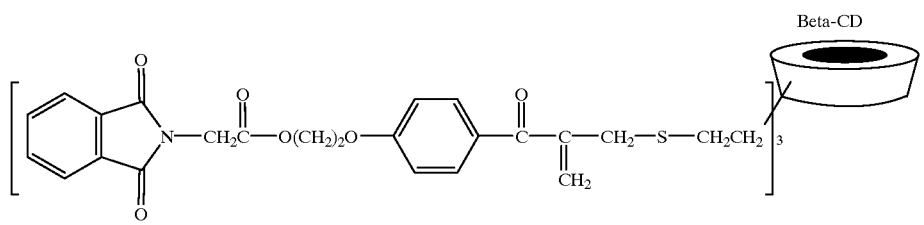

In another embodiment, as shown below, only the modified DARCUR 2959 without the phthaloyl glycine attached is reacted with the cyclodextrin to yield the following compound. This compound is capable of stabilizing a dye that is associated with the molecular includant and is represented by the following formula:

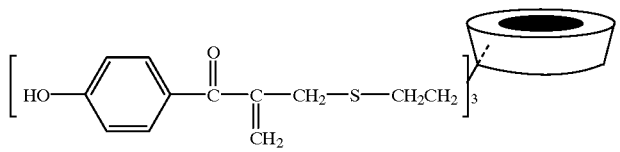

It is to be understood that photoreactors other than DARCUR 2959 can be used in the present invention.

In yet another embodiment, the dehydrated phthaloylglycine-2959 can be attached to the molecular includant via the opposite end of the molecule. One example of this embodiment is represented in the following formula:

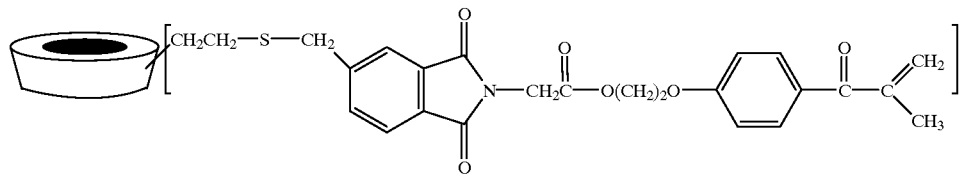

Another stabilizer that is considered part of the present invention is an arylketoalkene represented by the following general formula:

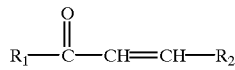

wherein when $R_1$ is an aryl group, $R_2$ is a hydrogen; alkyl; aryl; heterocyclic; or phenyl group, the phenyl group optionally being substituted with an alkyl, halo, amino, or thiol group; and wherein when $R_2$ is an aryl group, $R_1$ is a hydrogen; alkyl; aryl; heterocyclic; or phenyl group, the phenyl group optionally being substituted with an alky, halo, amino, or thiol group. Preferably, the alkene group is in the trans configuration.

Desirably, the arylketoalkene stabilizing compound is represented in the following formula.

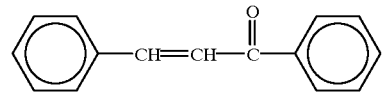

or

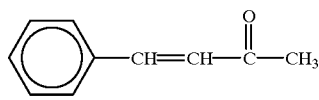

The arylketoalkene may also function as a wavelength-specific sensitizer in the present invention, and it may be associated with any of the previously discussed photoreactors. One method of associating a photoreactor with the arylketoalkene compound of the present invention is described in Example 32. The arylketoalkene compound may optionally be covalently bonded to the reactive species-generating photoinitiator. It is to be understood that the arylketoalkene compound of the present invention is not to be used with photoreactors in a composition where stability in natural sunlight is desired. More particularly, as the arylketoalkene compounds absorb radiation in the range of about 270 to 310 depending on the identity of $R_1$ and $R_2$, then these compounds are capable of absorbing the appropriate radiation from sunlight. Accordingly, these compounds when admixed with a photoreactor can effect a mutation of the colorant upon exposure to sunlight. Where such a change in color is not desired, then a photoreactor is not to be admixed with the arylketoalkene compound of the present invention, and the arylketoalkene compound is to be used with a colorant without a photoreactor.

In the embodiment where the arylketoalkene compound is covalently attached to another molecule, whichever $R_1$ or $R_2$ that is an aryl group will have a group including, but not limited to, a carboxylic acid group, an aldehyde group, an amino group, a haloalkyl group, a hydroxyl group, or a thioalkyl group attached thereto to allow the arylketoalkene to be covalently bonded to the other molecule. Accordingly, the arylketoalkene stabilizing compound is represented in the following formula:

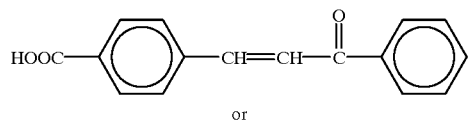

or

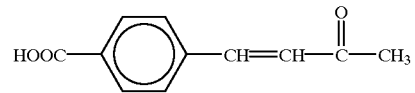

or

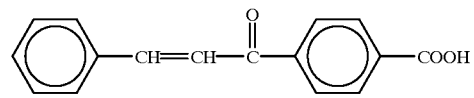

Although it is preferred that the group attached to the aryl group is in the para position to the remainder of the stabilizer molecule, the group may also be in the ortho or meta position to the remainder of the molecule.

Accordingly, this embodiment of the present invention provides a stabilizing arylketoalkene which, when associated with a colorant, stabilizes the colorant. Therefore, the above arylketoalkene can be used as an additive to any colorant composition. For example, as the arylketoalkene compound is poorly water soluble, it can be directly added to solvent or oil colorant compositions. Additionally, the arylketoalkene compound can be added to other colorant compositions that contain additives enabling the solubilization of the compound therein.

Further, the arylketoalkene stabilizing compounds can be solubilized in an aqueous solution by a variety of means. One means of solubilizing the arylketoalkene stabilizing compound of the present invention is to attach the compound to a large water soluble molecule, such as a cyclodextrin, as described in Examples 28 through 31. Desirably, between about 1 and 12 arylketoalkene molecules can be attached to a cyclodextrin molecule. More desirably, between about 4 to about 9 arylketoalkene molecules are attached to a cyclodextrin molecule. Accordingly, the arylketoalkene compound attached to cyclodextrin can be added to any aqueous colorant system to stabilize the colorant therein. It is to be understood that the stabilizing arylketoalkenes do not have to be attached to the molecular includants to exhibit their stabilizing activity.

Therefore, this embodiment provides a method for stabilizing colorant compositions by admixing the arylketoalkene compound with the colorant composition in an amount effective to stabilize the composition. The arylketoalkenes desirably should be present in the colorant medium or solution at a concentration of approximately 0.1 to 50% by weight, desirably between approximately 20% and 30% by weight. If no cyclodextrin is used, the desirable range is approximately 1 part dye to approximately 20 parts arylketoalkene.

Although the arylketoalkene compound need only be associated with the colorant, in some embodiments of the present invention, the arylketoalkene compound may be covalently bonded to the colorant.

Although not wanting to be limited by the following, it is theorized that the arylketoalkene compound of the present invention stabilizes colorants through functioning as a singlet oxygen scavenger. In the alternative, it is theorized that the arylketoalkene compound functions as a stabilizer of a colorant via the resonance of the unshared electron pairs in the p orbitals, e.g., it functions as an energy sink.

As a practical matter, the colorant, ultraviolet radiation transorber, modified photoreactor, arylketoalkene stabilizer, and molecular includant are likely to be solids depending upon the constituents used to prepare the molecules. However, any or all of such materials can be a liquid. The colored composition can be a liquid either because one or more of its components is a liquid, or, when the molecular includant is organic in nature, a solvent is employed. Suitable solvents include, but are not limited to, amides, such as N,N-dimethylformamide; sulfoxides, such as dimethylsulfoxide; ketones, such as acetone, methyl ethyl ketone, and methyl butyl ketone; aliphatic and aromatic hydrocarbons, such as hexane, octane, benzene, toluene, and the xylenes; esters, such as ethyl acetate; water; and the like. When the molecular includant is a cyclodextrin, particularly suitable solvents are the amides and sulfoxides.

In an embodiment where the composition of the present invention is a solid, the effectiveness of the above compounds on the colorant is improved when the colorant and the selected compounds are in intimate contact. To this end, the thorough blending of the components, along with other components which may be present, is desirable. Such blending generally is accomplished by any of the means known to those having ordinary skill in the art. When the colored composition includes a polymer, blending is facilitated if the colorant and the ultraviolet radiation transorber are at least partly soluble in softened or molten polymer. In such case, the composition is readily prepared in, for example, a two-roll mill. Alternatively, the composition of the present invention can be a liquid because one or more of its components is a liquid.

For some applications, the composition of the present invention typically will be utilized in particulate form. In other applications, the particles of the composition should be very small. Methods of forming such particles are well known to those having ordinary skill in the art.

The colored composition of the present invention can be utilized on or in any substrate. If one desires to mutate the colored composition that is present in a substrate, however, the substrate should be substantially transparent to the ultraviolet radiation which is employed to mutate the colorant. That is, the ultraviolet radiation will not significantly interact with or be absorbed by the substrate. As a practical matter, the composition typically will be placed on a substrate, with the most common substrate being paper. Other substrates, including, but not limited to, woven and nonwoven webs or fabrics, films, and the like, can be used, however.

The colored composition optionally may also contain a carrier, the nature of which is well known to those having ordinary skill in the art. For many applications, the carrier will be a polymer, typically a thermosetting or thermoplastic polymer, with the latter being the more common.

Further examples of thermoplastic polymers include, but are not limited to: end-capped polyacetals, such as poly (oxymethylene) or polyformaldehyde, poly (trichloroacetaldehyde), poly(n-valeraldehyde), poly (acetaldehyde), poly(propionaldehyde), and the like; acrylic polymers, such as polyacrylamide, poly(acrylic acid), poly (methacrylic acid), poly(ethyl acrylate), poly(methyl methacrylate), and the like; fluorocarbon polymers, such as poly(tetrafluoroethylene), perfluorinated ethylenepropylene copolymers, ethylenetetrafluoroethylene copolymers, poly-(chlorotrifluoroethylene), ethylene-chlorotrifluoroethylene copolymers, poly(vinylidene fluoride), poly(vinyl fluoride), and the like; epoxy resins, such as the condensation products of epichlorohydrin and bisphenol A; polyamides, such as poly(6-aminocaproic acid) or poly($\epsilon$-caprolactam), poly (hexamethylene adipamide), poly(hexamethylene sebacamide), poly(11-aminoundecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylene), and the like; polyaryl ethers, such as poly(oxy-2,6dimethyl-1,4-phenylene) or poly(p-phenylene oxide), and the like; polyaryl sulfones, such as poly(oxy-1,4-phenylenesulfonyl-1,4-phenyleneoxy-1,4-phenylene-isopropylidene-1,4-phenylene), poly (sulfonyl-1,4-phenyleneoxy-1,4-phenylenesulfonyl-4,4-biphenylene), and the like; polycarbonates, such as poly (bisphenol A) or poly(carbonyldioxy-1,4-phenyleneisopropylidene-1,4-phenylene), and the like; polyesters, such as poly(ethylene terephthalate), poly (tetramethylene terephthalate), poly(cyclohexylene-1,4-dimethylene terephthalate) or poly(oxymethylene-1,4-cyclohexylenemethyleneoxyterephthaloyl), and the like; polyaryl sulfides, such as poly(p-phenylene sulfide) or poly (thio-1,4-phenylene), and the like; polyimides, such as poly-(pyromellitimido-1,4-phenylene), and the like; polyolefins, such as polyethylene, polypropylene, poly(1-butene), poly (2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly (vinylidene chloride), polystyrene, and the like; and copolymers of the foregoing, such as acrylonitrile-butadienestyrene (ABS) copolymers, styrene-n-butylmethacrylate copolymers, ethylene-vinyl acetate copolymers, and the like.

Some of the more commonly used thermoplastic polymers include styrene-n-butyl methacrylate copolymers, polystyrene, styrene-n-butyl acrylate copolymers, styrene-butadiene copolymers, polycarbonates, poly(methyl methacrylate), poly(vinylidene fluoride), polyamides (nylon-12), polyethylene, polypropylene, ethylene-vinyl acetate copolymers, and epoxy resins.

Examples of thermosetting polymers include, but are not limited to, alkyd resins, such as phthalic anhydride-glycerol resins, maleic acid-glycerol resins, adipic acid-glycerol resins, and phthalic anhydride-pentaerythritol resins; allylic resins, in which such monomers as diallyl phthalate, diallyl isophthalate diallyl maleate, and diallyl chlorendate serve as nonvolatile cross-linking agents in polyester compounds; amino resins, such as aniline-formaldehyde resins, ethylene urea-formaldehyde resins, dicyandiamide-formaldehyde resins, melamine-formaldehyde resins, sulfonamide-formaldehyde resins, and urea-formaldehyde resins; epoxy resins, such as cross-linked epichlorohydrin-bisphenol A resins; phenolic resins, such as phenol-formaldehyde resins, including Novolacs and resols; and thermosetting polyesters, silicones, and urethanes.

In addition to the colorant, and ultraviolet radiation transorber or functionalized molecular includant, or modified photoreactor, or arylketoalkene stabilizer, and optional carrier, the colored composition of the present invention also can contain additional components, depending upon the application for which it is intended. Examples of such additional components include, but are not limited to, charge carriers, stabilizers against thermal oxidation, viscoelastic properties modifiers, cross-linking agents, plasticizers, charge control additives such as a quaternary ammonium salt; flow control additives such as hydrophobic silica, zinc stearate, calcium stearate, lithium stearate, polyvinylstearate, and polyethylene powders; and fillers such as calcium carbonate, clay and talc, among other additives used by those having ordinary skill in the art. Charge carriers are well known to those having ordinary skill in the art and typically are polymer-coated metal particles. The identities and amounts of such additional components in the colored composition are well known to one of ordinary skill in the art.

The present invention is further described by the examples which follow. Such examples, however, are not to be construed as limiting in any way either the spirit or scope of the present invention. In the examples, all parts are parts by weight unless stated otherwise.

EXAMPLE 1

This example describes the preparation of a β-cyclodextrin molecular includant having (1) an ultraviolet radiation transorber covalently bonded to the cyclodextrin outside of the cavity of the cyclodextrin, and (2) a colorant associated with the cyclodextrin by means of hydrogen bonds and/or van der Waals forces.

A. Friedel-crafts Acylation of Transorber

A 250-ml, three-necked, round-bottomed reaction flask was fitted with a condenser and a pressure-equalizing addition funnel equipped with a nitrogen inlet tube. A magnetic stirring bar was placed in the flask. While being flushed with nitrogen, the flask was charged with 10 g (0.05. mole) of 1-hydroxycyclohexyl phenyl ketone (IRGACURE 184, Ciba-Geigy Corporation, Hawthorne, N.Y.), 100 ml of anhydrous tetrahydofuran (Aldrich Chemical Company, Inc., Milwaukee, Wis.), and 5 g (0.05 mole) of succinic anhydride (Aldrich Chemical Co., Milwaukee, Wis.). To the continuously stirred contents of the flask then was added 6.7 g of anhydrous aluminum chloride (Aldrich Chemical Co., Milwaukee, Wis.). The resulting reaction mixture was maintained at about 0° C. in an ice bath for about one hour, after which the mixture was allowed to warm to ambient temperature for two hours. The reaction mixture then was poured into a mixture of 500 ml of ice water and 100 ml of diethyl ether. The ether layer was removed after the addition of a small amount of sodium chloride to the aqueous phase to aid phase separation. The ether layer was dried over anhydrous magnesium sulfate. The ether was removed under reduced pressure, leaving 12.7 g (87 percent) of a white crystalline powder. The material was shown to be 1-hydroxycyclohexyl 4-(2-carboxyethyl)carbonylphenyl ketone by nuclear magnetic resonance analysis.

B. Preparation of Acylated Transorber Acid Chloride

A 250-ml round-bottomed flask fitted with a condenser was charged with 12.0 g of 1-hydroxycyclohexyl 4-(2-carboxyethyl)carbonylphenyl ketone (0.04 mole), 5.95 g (0.05 mole) of thionyl chloride (Aldrich Chemical Co., Milwaukee, Wis.), and 50 ml of diethyl ether. The resulting reaction mixture was stirred at 30° C. for 30 minutes, after which time the solvent was removed under reduced pressure. The residue, a white solid, was maintained at 0.01 Torr for 30 minutes to remove residual solvent and excess thionyl chloride, leaving 12.1 g (94 percent) of 1-hydroxycyclohexyl 4-(2-chloroformylethyl) carbonylphenyl ketone.

C. Covalent Bonding of Acylated Transorber to Cyclodextrin

A 250-ml, three-necked, round-bottomed reaction flask containing a magnetic stirring bar and fitted with a thermometer, condenser, and pressure-equalizing addition funnel equipped with a nitrogen inlet tube was charged with 10 g (9.8 mmole) of β-cyclodextrin (American Maize-Products Company, Hammond, Ind.), 31.6 g (98 mmoles) of 1-hydroxycyclohexyl 4-(2-chloroformylethyl) carbonylphenyl ketone, and 100 ml of N,N-dimethylformamide while being continuously flushed with nitrogen. The reaction mixture was heated to 50° C. and 0.5 ml of triethylamine added. The reaction mixture was maintained at 50° C. for an hour and allowed to cool to ambient temperature. In this preparation, no attempt was made to isolate the product, a β-cyclodextrin to which an ultraviolet radiation transorber had been covalently coupled (referred to hereinafter for convenience as β-cyclodextrin-transorber).

The foregoing procedure was repeated to isolate the product of the reaction. At the conclusion of the procedure as described, the reaction mixture was concentrated in a rotary evaporator to roughly 10 percent of the original volume. The residue was poured into ice water to which sodium chloride then was added to force the product out of solution. The resulting precipitate was isolated by filtration and washed with diethyl ether. The solid was dried under reduced pressure to give 24.8 g of a white powder. In a third preparation, the residue remaining in the rotary evaporator was placed on top of an approximately 7.5-cm column containing about 15 g of silica gel. The residue was eluted with N,N-dimethylformamide, with the eluant being monitored by means of Whatman® Flexible-Backed TLC Plates (Catalog No. 05-713-161, Fisher Scientific, Pittsburgh, Pa.). The eluted product was isolated by evaporating the solvent. The structure of the product was verified by nuclear magnetic resonance analysis.

D. Association of Colorant with Cyclodextrin-transorber-preparation of Colored Composition To a solution of 10 g (estimated to be about 3.6 mmole) of beta-cyclodextrin-transorber in 150 ml of N,N-dimethylformamide in a 250-ml round-bottomed flask was added at ambient temperature 1.2 g (3.6 mmole) of Malachite Green oxalate (Aldrich Chemical Company, Inc., Milwaukee, Wis.), referred to hereinafter as Colorant A for convenience. The reaction mixture was stirred with a magnetic stirring bar for one hour at ambient temperature. Most of the solvent then was removed in a rotary evaporator and the residue was eluted from a silica gel column as already described. The beta-cyclodextrin-transorber Colorant A inclusion complex moved down the column first, cleanly separating from both free Colorant A and beta-cyclodextrin-transorber. The eluant containing the complex was collected and the solvent removed in a rotary evaporator. The residue was subjected to a reduced pressure of 0.01 Torr to remove residual solvent to yield a blue-green powder.

E. Mutation of Colored Composition

The beta-cyclodextrin-transorber Colorant A inclusion complex was exposed to ultraviolet radiation from two different lamps, Lamps A and B. Lamp A was a 222-nanometer excimer lamp assembly organized in banks of four cylindrical lamps having a length of about 30 cm. The lamps were cooled by circulating water through a centrally located or inner tube of the lamp and, as a consequence, they operated at a relatively low temperature, i.e., about 50° C. The power density at the lamp's outer surface typically is in the range of from about 4 to about 20 joules per square meter ($J/m^2$). However, such range in reality merely reflects the capabilities of current excimer lamp power supplies; in the future, higher power densities may be practical. The distance from the lamp to the sample being irradiated was 4.5 cm. Lamp B was a 500-watt Hanovia medium pressure mercury lamp (Hanovia Lamp Co., Newark, N.J.). The distance from Lamp B to the sample being irradiated was about 15 cm.

A few drops of an N,N-dimethylformamide solution of the beta-cyclodextrin-transorber Colorant A inclusion complex were placed on a TLC plate and in a small polyethylene weighing pan. Both samples were exposed to Lamp A and were decolorized (mutated to a colorless state) in 15–20 seconds. Similar results were obtained with Lamp B in 30 seconds.

A first control sample consisting of a solution of Colorant A and beta-cyclodextrin in N,N-dimethylformamide was not decolorized by Lamp A. A second control sample consisting of Colorant A and 1-hydroxycyclohexyl phenyl ketone in N,N-dimethylformamide was decolorized by Lamp A within 60 seconds. On standing, however, the color began to reappear within an hour.

To evaluate the effect of solvent on decolorization, 50 mg of the beta-cyclodextrin-transorber Colorant A inclusion complex was dissolved in 1 ml of solvent. The resulting solution or mixture was placed on a glass microscope slide and exposed to Lamp A for 1 minute. The rate of decolorization, i.e., the time to render the sample colorless, was directly proportional to the solubility of the complex in the solvent, as summarized below.

TABLE 1

| Solvent | Solubility | Decolorization Time |
| --- | --- | --- |
| N,N-Dimethylformamide | Poor | 1 minute |
| Dimethylsulfoxide | Soluble | <10 seconds |
| Acetone | Soluble | <10 seconds |
| Hexane | Insoluble | — |
| Ethyl Acetate | Poor | 1 minute |

Finally, 10 mg of the beta-cyclodextrin-transorber Colorant A inclusion complex were placed on a glass microscope slide and crushed with a pestle. The resulting powder was exposed to Lamp A for 10 seconds. The powder turned colorless. Similar results were obtained with Lamp B, but at a slower rate.

EXAMPLE 2

Because of the possibility in the preparation of the colored composition described in the following examples for the acylated transorber acid chloride to at least partially occupy the cavity of the cyclodextrin, to the partial or complete exclusion of colorant, a modified preparative procedure was carried out. Thus, this example describes the preparation of a beta-cyclodextrin molecular includant having (1) a colorant at least partially included within the cavity of the cyclodextrin and associated therewith by means of hydrogen bonds and/or van der Waals forces, and (2) an ultraviolet radiation transorber covalently bonded to the cyclodextrin substantially outside of the cavity of the cyclodextrin.

A. Association of Colorant with a Cyclodextrin

To a solution of 10.0 g (9.8 mmole) of beta-cyclodextrin in 150 ml of N,N-dimethylformamide was added 3.24 g (9.6 mmoles) of Colorant A. The resulting solution was stirred at ambient temperature for one hour. The reaction solution was concentrated under reduced pressure in a rotary evaporator to a volume about one-tenth of the original volume. The residue was passed over a silica gel column as described in Part C of Example 1. The solvent in the eluant was removed under reduced pressure in a rotary evaporator to give 12.4 g of a blue-green powder, beta-cyclodextrin Colorant A inclusion complex.

B. Covalent Bonding of Acylated Transorber to Cyclodextrin Colorant Inclusion Complex—Preparation of Colored Composition A 250-ml, three-necked, round-bottomed reaction flask containing a magnetic stirring bar and fitted with a thermometer, condenser, and pressure-equalizing addition funnel equipped with a nitrogen inlet tube was charged with 10 g (9.6 mmole) of beta-cyclodextrin Colorant A inclusion complex, 31.6 g (98 mmoles) of 1-hydroxycyclohexyl 4-(2-chloroformylethyl)carbonylphenyl ketone prepared as described in Part B of Example 1, and 150 ml of N,N-dimethylformamide while being continuously flushed with nitrogen. The reaction mixture was heated to 50° C. and 0.5 ml of triethylamine added. The reaction mixture was maintained at 50° C. for an hour and allowed to cool to ambient temperature. The reaction mixture then was worked up as described in Part A, above, to give 14.2 g of beta-cyclodextrin-transorber Colorant A inclusion complex, a blue-green powder.

C. Mutation of Colored Composition

The procedures described in Part E of Example 1 were repeated with the beta-cyclodextrin-transorber Colorant A inclusion complex prepared in Part B, above, with essentially the same results.

EXAMPLE 3

This example describes a method of preparing an ultraviolet radiation transorber, 2-[p-(2-methyllactoyl)phenoxy]ethyl 1,3-dioxo-2-isoindolineacetate, designated phthaloylglycine-2959.

The following was admixed in a 250 ml, three-necked, round bottomed flask fitted with a Dean & Stark adapter with condenser and two glass stoppers: 20.5 g (0.1 mole) of the wavelength selective sensitizer, phthaloylglycine (Aldrich Chemical Co., Milwaukee, Wis.); 24.6 g (0.1 mole) of the photoreactor, DARCUR 2959 (Ciba-Geigy, Hawthorne, N.Y.); 100 ml of benzene (Aldrich Chemical Co., Milwaukee, Wis.); and 0.4 g p-toluenesulfonic acid (Aldrich Chemical Co., Milwaukee, Wis.). The mixture was heated at reflux for 3 hours after which time 1.8 ml of water was collected. The solvent was removed under reduced pressure to give 43.1 g of white powder. The powder was recrystallized from 30% ethyl acetate in hexane (Fisher) to yield 40.2 g (93%) of a white crystalline powder having a melting point of 153–4° C. The reaction is summarized as follows:

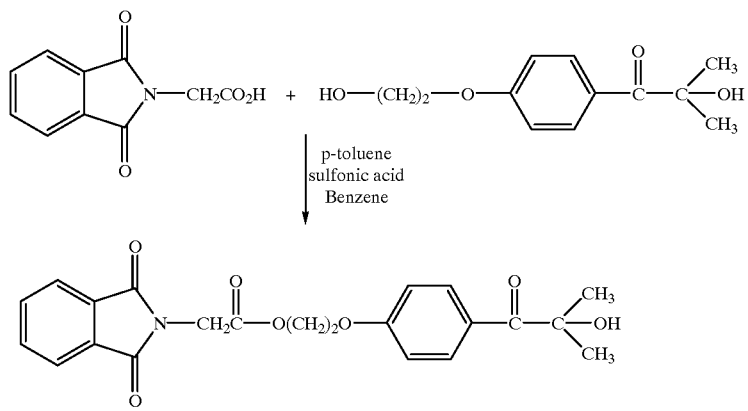

The resulting product, designated phthaloylglycine-2959, had the following physical parameters:

IR [NUJOL MULL] $v_{max}$ 3440, 1760, 1740, 1680, 1600 cm-1

1H NMR [CDC13] ∂ ppm 1.64[s], 4.25[m], 4.49[m], 6.92[m], 7.25[m], 7.86[m], 7.98[m], 8.06[m] ppm

EXAMPLE 4

This example describes a method of dehydrating the phthaloylglycine-2959 produced in Example 3.

The following was admixed in a 250 ml round bottomed flask fitted with a Dean & Stark adapter with condenser: 21.6 g (0.05 mole) phthaloylglycine-2959; 100 ml of anhydrous benzene (Aldrich Chemical Co., Milwaukee, Wis.); and 0.1 g p-toluenesulfonic acid (Aldrich Chemical Co., Milwaukee, Wis.). The mixture was refluxed for 3 hours. After 0.7 ml of water had been collected in the trap, the solution was then removed under vacuum to yield 20.1 g (97%) of a white solid. However, analysis of the white solid showed that this reaction yielded only 15 to 20% of the desired dehydration product. The reaction is summarized as follows:

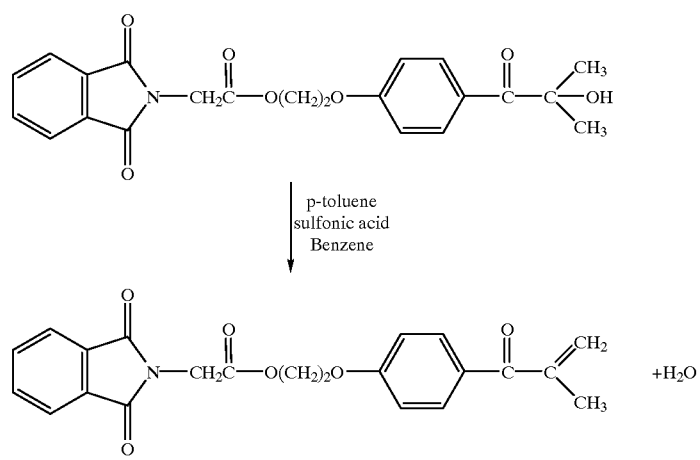

The resulting reaction product had the following physical parameters:

IR (NUJOL) $v_{max}$ 1617 cm$^{-1}$ (C=C—C=O)

EXAMPLE 5

This example describes the Nohr-MacDonald elimination reaction used to dehydrate the phthaloylglycine-2959 produced in Example 3.

Into a 500 ml round bottomed flask were placed a stirring magnet, 20.0 g (0.048 mole) of the phthaloylglycine-2959, and 6.6 g (0.048 mole) of anhydrous zinc chloride (Aldrich Chemical Co., Milwaukee, Wis.). 250 ml of anhydrous p-xylene (Aldrich Chemical Co., Milwaukee, Wis.) was added and the mixture refluxed under argon atmosphere for two hours. The reaction mixture was then cooled, resulting in a white precipitate which was collected. The white powder was then recrystallized from 20% ethyl acetate in hexane to yield 18.1 g (95%) of a white powder. The reaction is summarized as follows:

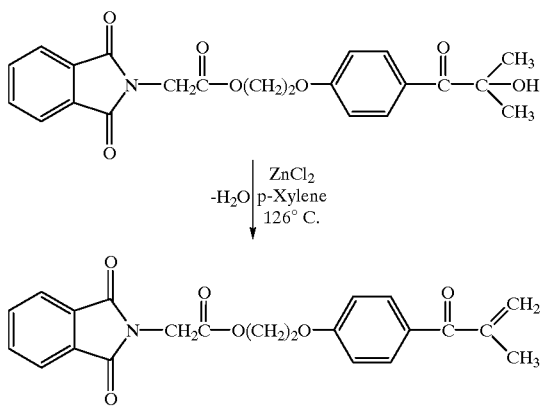

The resulting reaction product had the following physical parameters:

Melting Point: 138° C. to 140° C.

Mass spectrum: m/e: 393 M+, 352, 326, 232, 160.

IR (KB) $v_{max}$ 1758, 1708, 1677, 1600 cm-1

1H NMR [DMSO] ∂ ppm 1.8(s), 2.6(s), 2.8 (d), 3.8 (d), 4.6 (m), 4.8 (m), 7.3(m), 7.4 (m), 8.3 (m), and 8.6 (d)

13C NMR [DMSO] ∂ ppm 65.9 (CH2=)

EXAMPLE 6

This example describes a method of producing a beta-cyclodextrin having dehydrated phthaloylglycine-2959 groups from Example 4 or 5 covalently bonded thereto.

The following was admixed in a 100 ml round-bottomed flask: 5.0 g (4 mmole) beta-cyclodextrin (American Maize Product Company, Hammond, Ind.) (designated beta-CD in the following reaction); 8.3 g (20 mmole) dehydrated phthaloylglycine-2959; 50 ml of anhydrous DMF; 20 ml of benzene; and 0.01 g p-tolulenesulfonyl chloride (Aldrich Chemical Co., Milwaukee, Wis.). The mixture was chilled in a salt/ice bath and stirred for 24 hours. The reaction mixture was poured into 150 ml of weak sodium bicarbonate solution and extracted three times with 50 ml ethyl ether. The aqueous layer was then filtered to yield a white solid comprising the beta-cyclodextrin with phthaloylglycine-2959 group attached. A yield of 9.4 g was obtained. Reverse phase TLC plate using a 50:50 DMF:acetonitrile mixture showed a new product peak compared to the starting materials. The reaction is summarized as follows:

The beta-cyclodextrin molecule has several primary alcohols and secondary alcohols with which the phthaloylglycine-2959 can react. The above representative reaction only shows a single phthaloylglycine-2959 molecule for illustrative purposes.

EXAMPLE 7

This example describes a method of associating a colorant and an ultraviolet radiation transorber with a molecular includant. More particularly, this example describes a method of associating the colorant crystal violet with the molecular includant beta-cyclodextrin covalently bonded to the ultraviolet radiation transorber dehydrated phthaloylglycine-2959 of Example 6.

The following was placed in a 100 ml beaker: 4.0 g beta-cyclodextrin having a dehydrated phthaloylglycine-2959 group; and 50 ml of water. The water was heated to 70° C. at which point the solution became clear. Next, 0.9 g (2.4 mmole) crystal violet (Aldrich Chemical Company, Milwaukee, Wis.) was added to the solution, and the solution was stirred for 20 minutes. Next, the solution was then filtered. The filtrand was washed with the filtrate and then dried in a vacuum oven at 84° C. A violet-blue powder was obtained having 4.1 g (92%) yield. The resulting reaction product had the following physical parameters:

U.V. Spectrum DMF $\nu_{max}$ 610 nm (cf cv $\nu_{max}$ 604 nm)

EXAMPLE 8

This example describes a method of producing the ultraviolet radiation transorber 4(4-hydroxyphenyl) butan-2-one-2959 (chloro substituted).

The following was admixed in a 250 ml round-bottomed flask fitted with a condenser and magnetic stir bar: 17.6 g (0.1 mole) of the wavelength selective sensitizer, 4(4-hydroxyphenyl) butan-2-one (Aldrich Chemical Company, Milwaukee, Wis.); 26.4 g (0.1 mole) of the photoreactor, chloro substituted DARCUR 2959 (Ciba-Geigy Corporation, Hawthorne, N.Y.); 1.0 ml of pyridine (Aldrich Chemical Company, Milwaukee, Wis.); and 100 ml of anhydrous tetrahydrofuran (Aldrich Chemical Company, Milwaukee, Wis.). The mixture was refluxed for 3 hours and the solvent partially removed under reduced pressure (60% taken off). The reaction mixture was then poured into ice water and extracted with two 50 ml aliquots of diethyl ether. After drying over anhydrous magnesium sulfate and removal of solvent, 39.1 g of white solvent remained. Recrystallization of the powder from 30% ethyl acetate in hexane gave 36.7 g (91%) of a white crystalline powder, having a melting point of 142–3° C. The reaction is summarized as follows:

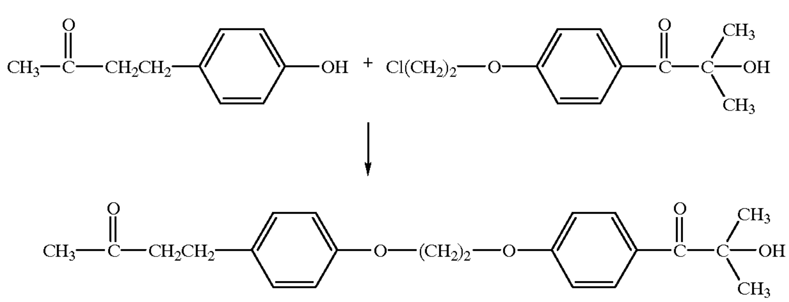

The resulting reaction product had the following physical parameters:

IR [NUJOL MULL] $\nu_{max}$ 3460, 1760, 1700, 1620, 1600 $cm^{-1}$ $^1H$ [$CDCl_3$] ∂ ppm 1.62[s], 4.2[m], 4.5[m], 6.9[m] ppm The ultraviolet radiation transorber produced in this example, 4(4-hydroxyphenyl) butan-2-one-2959 (chloro substituted), may be associated with beta-cyclodextrin and a colorant such as crystal violet, using the methods described above wherein 4(4-hydroxyphenyl) butan-2-one-2959 (chloro substituted) would be substituted for the dehydrated phthaloylglycine-2959.

EXAMPLE 9

Stabilizing Activity of the Radiation Transorber

This example demonstrates the ability of the present invention to stabilize colorants against light. Victoria Pure Blue BO is admixed in acetonitrile with phthaloylglycine-2959 as represented in the following formulas:

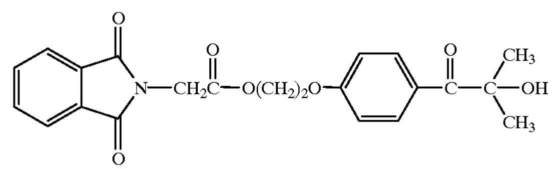

phthaloylglycine-2959 and dehydrated phthaloylglycine-2959:

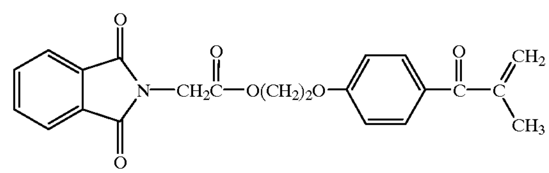

dehydrated phthaloylglycine-2959:

Solutions were prepared according to Table 2. The dye solutions were carefully, uniformly spread on steel plates to a thickness of approximately 0.1 mm. The plates were then immediately exposed to a medium pressure 1200 watt high intensity quartz arc mercury discharge lamp (Conrad-Hanovia, Inc., Newark, N.J.) at a distance of 30 cm from the light. The mercury discharge light is a source of high intensity, broad spectrum light that is used in accelerated fading analyses. Table 2 shows the results of the fade time with the various solutions. Fade time is defined as the time until the dye became colorless to the naked eye.

TABLE 2

|  | Victoria pure Blue BO | Fade Time |
|---|---|---|
| Phthaloylglycine-2959 | | |
| 3 parts by weight | 1 part by weight | 2 min |
| 10 parts by weight | 1 part by weight | 1½ min |
| 20 parts by weight | 1 part by weight | 30 sec |
| Dehydrated Phthaloylglycine-2959 | | |
| 3 parts by weight | 1 part by weight | 4 min |
| 10 parts by weight | 1 part by weight | 8 min |
| 20 parts by weight | 1 part by weight | >10 min |

As can be seen in Table 2, when phthaloylglycine-2959 was admixed with Victoria Pure Blue BO, the dye faded when exposed to the mercury dwascharge light. However, when dehydrated phthaloylglycine-2959 was admixed with the Victoria Pure Blue BO at a ratio of 10 parts dehydrated phthaloylglycine-2959 to one part Victoria Pure Blue BO, there was increased stabilization of the dye to light. When the ratio was 20 parts dehydrated phthaloylglycine-2959 to one part Victoria Pure Blue BO, the dye was substantially stabilized to the mercury dwascharge light in the time limits of the exposure.

EXAMPLE 10

To determine whether the hydroxy and the dehydroxy 2959 have the capability to stabilize colorants the following experiment was conducted. The following two compounds, as represented in the following formula, were tested as described below:

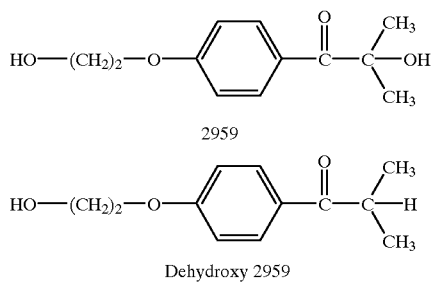

20 parts by weight of the hydroxy and the dehydroxy 2959 were admixed separately to one part by weight of Victoria Pure Blue BO in acetonitrile. The dye solutions were cwerefully, uniformly spread on steel plates to a thickness of approximately 0.1 mm. The plates were then immediately exposed to a mercury discharge light at a distance of 30 cm from the light. The mercury discharge light is a source of high intensity, broad spectrum light that is used in accelerated fading analyses. Table 3 shows the results of the fade time with the various solutions. Fade time is defined as the time until the dye became colorless to the naked eye.

TABLE 3

| Compound | Victoria Pure Blue | Fade Time |
|---|---|---|
| 20 parts 2959 (Hydroxy) | 1 part | <2 min |
| 20 parts 2959 (Dehydroxy) | 1 part | <2 min |
| None | 1 part | <2 min |

EXAMPLE 11
Stabilizing Activity of the Radiation Transorber and a Molecular Includant This example demonstrates the capability of dehydrated phthaloylglycine-2959 bound to beta-cyclodextrin to stabilize dyes against light. The Victoria Pure Blue BO associated with the radiation transorber was tested to determine its capability to stabilize the associated dye against light emitted from a mercury discharge light. In addition, the Victoria Pure Blue BO alone and Victoria Pure Blue BO admixed with beta cyclodextrin were tested as controls. The compositions tested were as follows:

1. Victoria Pure Blue BO only at a concentration of 10 mg/ml in acetonitrile.
2. Victoria Pure Blue BO included in beta cyclodextrin at a concentration of 20 mg/ml in acetonitrile.
3. The Victoria Pure Blue BO included in beta cyclodextrin to which the radiation transorber (dehydrated phthaloylglycine-2959) is covalently attached at a concentration of 20 mg/ml in acetonitrile.

The protocol for testing the stabilizing qualities of the three compositions is as follows: the dye solutions were carefully, uniformly spread on steel plates to a thickness of approximately 0.1 nm. The plates were then immediately exposed to a medium pressure 1200 watt high intensity quartz arc mercury discharge lamp (Conrad-Hanovia, Inc., Newark, N.J.) at a distance of 30 cm from the lamp.

TABLE 4

| Composition | Fade Time |
|---|---|
| 1 | 5 sec |
| 2 | 5 sec |
| 3 | >10 minutes[a] |

[a]There is a phase change after 10 minutes due to extreme heat

As shown in Table 4, only composition number 3, the Victoria Pure Blue BO included in cyclodextrin with the radiation transorber covalendy attached to the β-cyclodextrin was capable of stabilizing the dye under the mercury discharge light.

EXAMPLE 12
Preparation of Epoxide Intermediate of Dehydrated Phthaloylglycine-2959

The epoxide intermediate of dehydrated phthaloylglycine 2959 was prepared according to the following reaction:

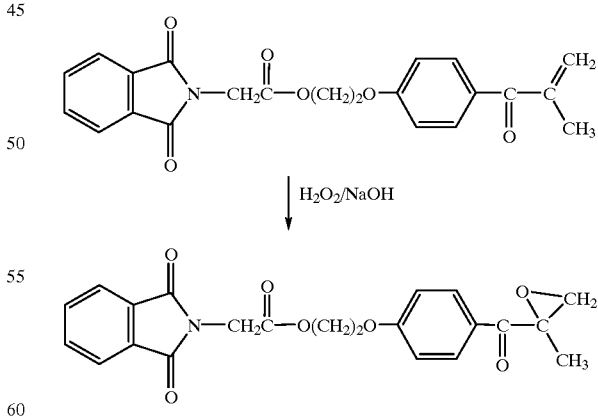

In a 250 ml, three-necked, round bottomed flask fitted with an addition funnel, thermometer and magnetic stirrer was placed 30.0 g (0.076 mol) of the dehydrated phthaloylglycine-2959, 70 ml methanol and 20.1 ml hydrogen peroxide (30% solution). The reaction mixture was stirred and cooled in a water/ice bath to maintain a temperature in the range 15°–20° C. 5.8 ml of a 6 N NaOH solution was placed in the addition funnel and the solution was slowly added to maintain the reaction mixture temperature of 15°–20° C. This step took about 4 minutes. The mixture was then stirred for 3 hours at about 20°–25° C. The reaction mixture was then poured into 90 ml of water and extracted with two 70 ml portions of ethyl ether. The organic layers were combined and washed with 100 ml of water, dried with anhydrous $MgSO_4$ filtered, and the ether removed on a rotary evaporator to yield a white solid (yield 20.3 g, 65%). The IR showed the stretching of the C—O—C group and the material was used without further purification.

EXAMPLE 13
Attachment of Epoxide Intermediate to Thiol Cyclodextrin

The attachment of the epoxide intermediate of dehydrated phthaloylglycine 2959 was done according to the following reaction:

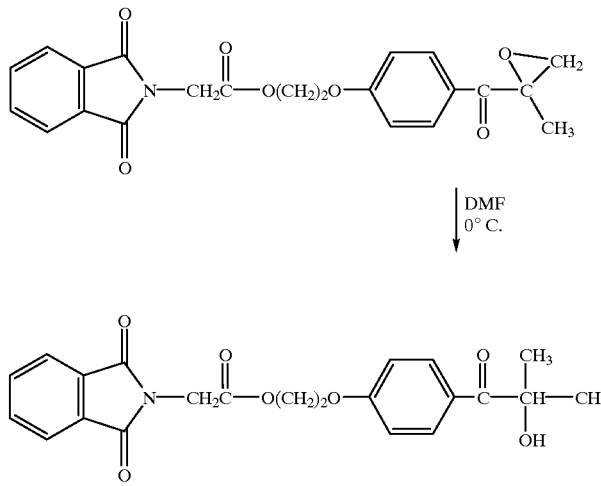

In a 250 ml 3-necked round bottomed flask fitted with a stopper and two glass stoppers, all being wired with copper wire and attached to the flask with rubber bands, was placed 30.0 g (0.016 mol) thiol cyclodextrin and 100 ml of anhydrous dimethylformamide (DMF) (Aldrich Chemical Co., Milwaukee, Wis.). The reaction mixture was cooled in a ice bath and 0.5 ml diisopropyl ethyl amine was added. Hydrogen sulfide was bubbled into the flask and a positive pressure maintained for 3 hours. During the last hour, the reaction mixture was allowed to warm to room temperature.

The reaction mixture was flushed with argon for 15 minutes and then poured into 70 ml of water to which was then added 100 ml acetone. A white precipitate occurred and was filtered to yield 20.2 g (84.1%) of a white powder which was used without further purification.

In a 250 ml round bottomed flask fitted with a magnetic stirrer and placed in an ice bath was placed 12.7 (0.031 mol), 80 ml of anhydrous DMF (Aldrich Chemical Co., Milwaukee, Wis.) and 15.0 g (0.010 mol) thiol CD. After the reaction mixture was cooled, 0.5 ml of diisopropyl ethyl amine was added and the reaction mixture stirred for 1 hour at 0°C. to 5° C. followed by 2 hours at room temperature. The reaction mixture was then poured into 200 ml of ice water and a white precipitate formed immediately. This was filtered and washed with acetone. The damp white powder was dried in a convection oven at 80° C. for 3 hours to yield a white powder. The yield was 24.5 g (88%).

EXAMPLE 14
Insertion of Victoria Pure Blue in the Cyclodextrin Cavity

In a 250 ml Erlenmeyer flask was placed a magnetic stirrer, 40.0 g (0.014 mol) of the compound and 100 ml water. The flask was heated on a hot plate to 80°C. When the white cloudy mixture became clear, 7.43 g (0.016 mol) of Victoria Pure Blue BO powder was then added to the hot solution and stirred for 10 minutes then allowed to cool to 50° C. The contents were then filtered and washed with 20 ml of cold water.

The precipitate was then dried in a convention oven at 80° C. for 2 hours to yield a blue powder 27.9 g (58.1%).

EXAMPLE 15

The preparation of a tosylated cyclodextrin with the dehydroxy phthaloylglycine 2959 attached thereto is performed by the following reactions:

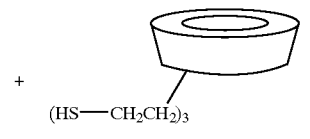

To a 500 ml 3-necked round bottomed flask fitted with a bubble tube, condenser and addition funnel, was placed 10 g (0.025 mole) of the dehydrated phthaloylglycine 2959 in 150 ml of anhydrous N,N-diethylformamide (Aldrich Chemical Co., Milwaukee, Wis.) cooled to 0°C. in an ice bath and stirred with a magnetic stirrer. The synthesis was repeated except that the flask was allowed to warm up to 60° C. using a warm water bath and the $H_2S$ pumped into the reaction flask till the stoppers started to move (trying to release the pressure). The flask was then stirred under these conditions for 4 hours. The saturated solution was kept at a positive pressure of $H_2S$. The stoppers were held down by wiring and rubber bands. The reaction mixture was then allowed to warm-up overnight. The solution was then flushed with argon for 30 minutes and the reaction mixture poured onto 50 g of crushed ice and extracted three times (3×80 ml) with diethyl ether (Aldrich Chemical Co., Milwaukee, Wis.).

The organic layers were condensed and washed with water and dried with $MgSO_4$. Removal of the solvent on a rotary evaporator gave 5.2 g of a crude product. The product was purified on a silica column using 20% ethyl acetate in hexane as eluant. 4.5 g of a white solid was obtained.

A tosylated cyclodextrin was prepared according to the following reaction:

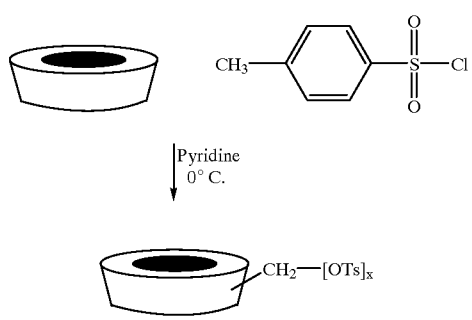

NMR peaks for each of the six carbon atoms are given in Table 5.

TABLE 5

| Carbon Atom | NMR Peak (ppm) |
|---|---|
| 1 | 101.8 |
| 2 | 72.9 |
| 3 | 72.3 |
| 4 | 81.4 |
| 5 | 71.9 |
| 6 | 59.8 |

The presence of the tosyl group shifts the NMR peaks of the 5-position and 6-position carbon atoms to 68.8 and 69.5 ppm, respectively.

The degree of substitution was calculated by integrating the NMR peak for the 6-position tosylated carbon, integrating the NMR peak for the 6-position hydroxy-substituted carbon, and dividing the former by the latter. The integrations yielded 23.6 and 4.1, respectively, and a degree of substitution of 5.9. Thus, the average degree of substitution in this example is about 6.

The tosylated cyclodextrin with the dehydroxy phthaloylglycine 2959 attached was prepared according to the following reaction:

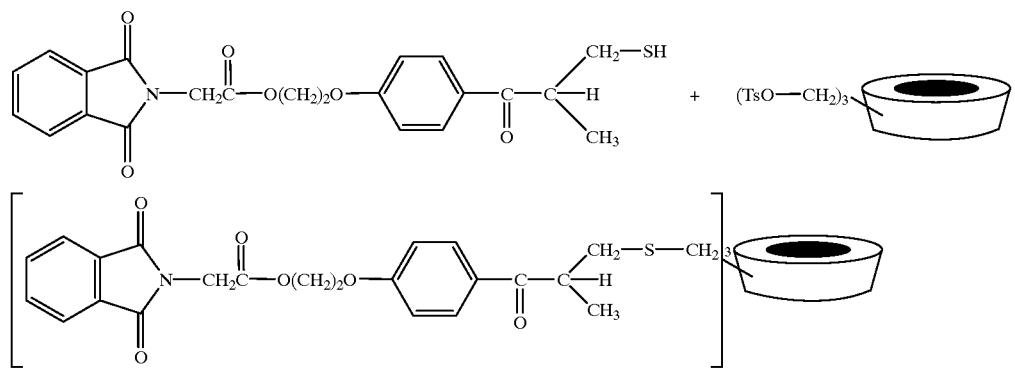

To a 100 ml round bottomed flask was placed 6.0 g β-cyclodextrin (American Maize Product Company), 10.0 g (0.05 mole) p-toluenesulfonyl chloride (Aldrich Chemical Co., Milwaukee, Wis.), 50 ml of pH 10 buffer solution (Fisher). The resultant mixture was stirred at room temperature for 8 hours after which it was poured on ice (approximately 100 g) and extracted with diethyl ether. The aqueous layer was then poured into 50 ml of acetone (Fisher) and the resultant, cloudy mixture filtered. The resultant white powder was then run through a Sephadex column (Aldrich Chemical Co., Milwaukee, Wis.) using n-butanol, ethanol, and water (5:4:3 by volume) as eluant to yield a white powder. The yield was 10.9%.

The degree of substitution of the white powder (tosyl-cyclodextrin) was determined by $^{13}C$ NMR spectroscopy (DMF-d6) by comparing the ratio of hydroxy substituted carbons versus tosylated carbons, both at the 6 position. When the 6-position carbon bears a hydroxy group, the To a 250 ml round bottomed flask was added 10.0 g (4–8 mole) of tosylated substituted cyclodextrin, 20.7 g (48 mmol) of thiol (mercapto dehydrated phthaloylglycine 2959) in 100 ml of DMF. The reaction mixture was cooled to 0° C. in an ice bath and stirred using a magnetic stirrer. To the solution was slowly dropped in 10 ml of ethyl diisopropylamine (Aldrich Chemical Co., Milwaukee, Wis.) in 20 ml of DMF. The reaction was kept at 0° C. for 8 hours with stirring. The reaction mixture was extracted with diethyl ether. The aqueous layer was then treated with 500 ml of acetone and the precipitate filtered and washed with acetone. The product was then run on a Sephadex column using n-butanol, ethanol, and water (5:4:3 by volume) to yield a white powder. The yield was 16.7 g.

The degree of substitution of the functionalized molecular includant was determined as described above. In this case, the presence of the derivatized ultraviolet radiation transorber shifts the NMR peak of the 6-position carbon atom to 63.1. The degree of substitution was calculated by integrating the NMR peak for the 6-position substituted carbon, integrating the NMR peak for the 6-position hydroxy-substituted carbon, and dividing the former by the latter. The integrations yielded 67.4 and 11.7, respectively, and a degree of substitution of 5.7. Thus, the average degree of substitution in this example is about 6. The reaction above shows the degree of substitution to be "n". Although n represents the value of substitution on a single cyclodextrin, and therefore, can be from 0 to approximately 24, it is to be understood that the average degree of substitution is about 6.

EXAMPLE 16

The procedure of Example 15 was repeated, except that the amounts of β-cyclodextrin and p-toluenesulfonic acid (Aldrich) were 6.0 g and 5.0 g, respectively. In this case, the degree of substitution of the cyclodextrin was found to be about 3.

EXAMPLE 17

The procedure of Example 15 was repeated, except that the derivatized molecular includant of Example 16 was employed in place of that from Example 15. The average degree of substitution of the functionalized molecular includant was found to be about 3.

EXAMPLE 18

This example describes the preparation of a colored composition which includes a mutable colorant and the functionalized molecular includant from Example 15.

In a 250-ml Erlenmeyer flask containing a magnetic stirring bar was placed 20.0 g (5.4 mmoles) of the functionalized molecular includant obtained in Example 15 and 100 g of water. The water was heated to 80° C., at which temperature a clear solution was obtained. To the solution was added slowly, with stirring, 3.1 g (6.0 mmoles) of Victoria Pure Blue BO (Aldrich). A precipitate formed which was removed from the hot solution by filtration. The precipitate was washed with 50 ml of water and dried to give 19.1 g (84 percent) of a blue powder, a colored composition consisting of a mutable colorant, Victoria Pure Blue BO, and a molecular includant having covalently coupled to it an average of about six ultraviolet radiation transorber molecules per molecular includant molecule.

EXAMPLE 19

The procedure of Example 18 was repeated, except that the functionalized molecular includant from Example 17 was employed in place of that from Example 15.

EXAMPLE 20

This example describes mutation or decolorization rates for the compositions of Examples 7 (wherein the beta-cyclodextrin has dehydrated phthaloyl glycine-2959 from Example 4 covalently bonded thereto), 18 and 19.

In each case, approximately 10 mg of the composition was placed on a steel plate (Q-Panel Company, Cleveland, Ohio). Three drops (about 0.3 ml) of acetonitrile (Burdick & Jackson, Muskegon, Mich.) was placed on top of the composition and the two materials were quickly mixed with a spatula and spread out on the plate as a thin film. Within 5–10 seconds of the addition of the acetonitrile, each plate was exposed to the radiation from a 222-nanometer excimer lamp assembly. The assembly consisted of a bank of four cylindrical lamps having a length of about 30 cm. The lamps were cooled by circulating water through a centrally located or inner tube of the lamp and, as a consequence, they operated at a relatively low temperature, i.e., about 50° C. The power density at the lamp's outer surface typically was in the range of from about 4 to about 20 joules per square meter ($J/m^2$). However, such range in reality merely reflects the capabilities of current excimer lamp power supplies in the future, higher power densities may be practical. The distance from the lamp to the sample being irradiated was 4.5 cm. The time for each film to become colorless to the eye was measured. The results are summarized in Table 6.

TABLE 6

| Decolorization Times for Various Compositions | |
|---|---|
| Composition | Decolorization Times (Seconds) |
| Example 18 | 1 |
| Example 19 | 3–4 |
| Example 7 | 7–8 |

Figure 13:
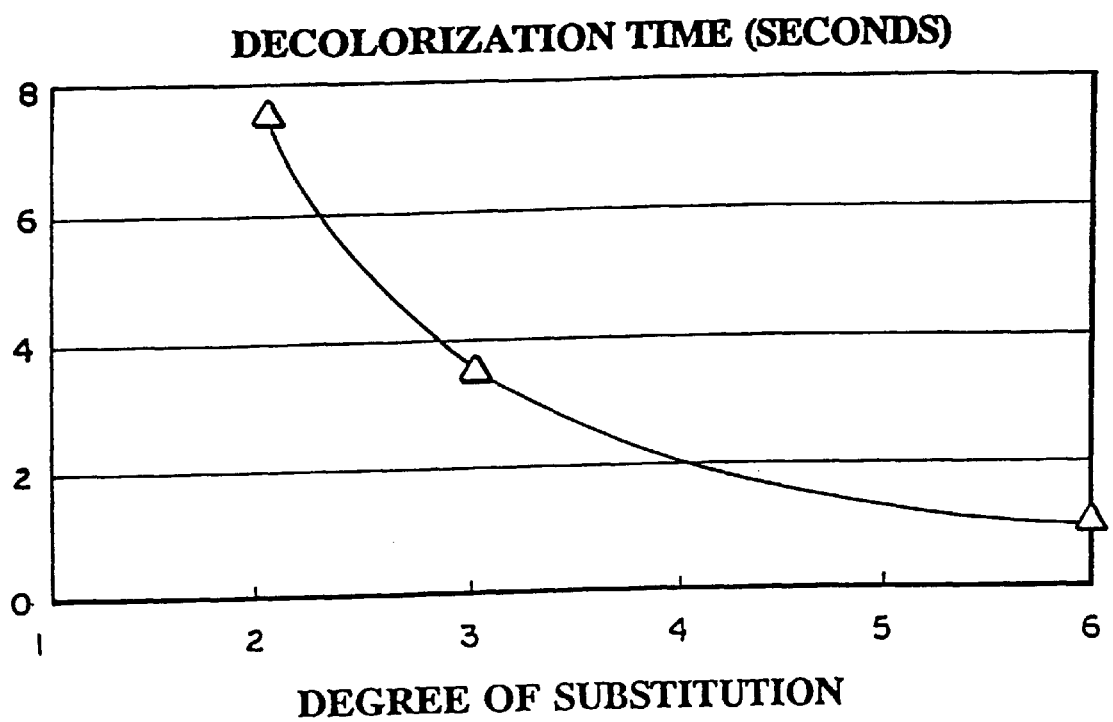
FIG. 13 is a plot of the average number of ultraviolet radiation transorber molecules which are covalently coupled to each molecule of a molecular includant in several colored compositions, which number also is referred to by the term, "degree of substitution," versus the decolorization time upon exposure to 222-nanometer excimer lamp ultraviolet radiation.

While the data in Table 6 demonstrate the clear superiority of the colored compositions of the present invention, such data were plotted as degree of substitution versus decolorization time. The plot is shown in FIG. 13. FIG. 13 not only demonstrates the significant improvement of the colored compositions of the present invention when compared with compositions having a degree of substitution less than three, but also indicates that a degree of substitution of about 6 is about optimum. That is, the figure indicates that little if any improvement in decolonization time would be achieved with degrees of substitution greater than about 6.

EXAMPLE 21

This example describes the preparation of a complex consisting of a mutable colorant and the derivatized molecular includant of Example 15.

The procedure of Example 18 was repeated, except that the functionalized molecular includant of Example 15 was replaced with 10 g (4.8 mmoles) of the derivatized molecular includant of Example 15 and the amount of Victoria Pure Blue BO was reduced to 2.5 g (4.8 mmoles). The yield of washed solid was 10.8 g (86 percent) of a mutable colorant associated with the β-cyclodextrin having an average of six tosyl groups per molecule of molecular includant.

EXAMPLE 22

This example describes the preparation of a colored composition which includes a mutable colorant and a functionalized molecular includant.

The procedure of preparing a functionalized molecular includant of Example 15 was repeated, except that the tosylated β-cyclodextrin was replaced with 10 g (3.8 mmoles) of the complex obtained in Example 21 and the amount of the derivatized ultraviolet radiation transorber prepared in Example 15 was 11.6 g (27 mmoles). The amount of colored composition obtained was 11.2 g (56 percent). The average degree of substitution was determined as described above, and was found to be 5.9, or about 6.

EXAMPLE 23

The following two compounds, as represented in the following formulas, were tested for their ability to stabilize Victoria Pure Blue BO:

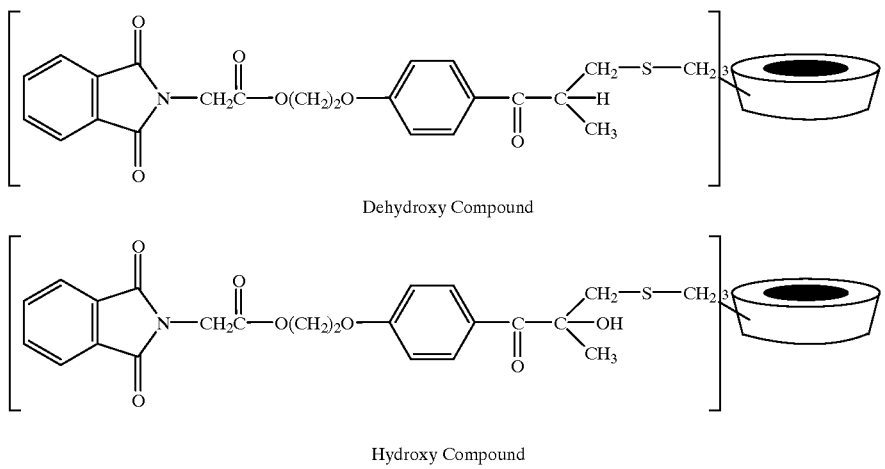

Dehydroxy Compound

Hydroxy Compound

This example further demonstrates the ability of the present invention to stabilize colorants against light. The two compounds containing Victoria Pure Blue BO as an includant in the cyclodextrin cavity were tested for light fastness under a medium pressure mercury discharge lamp. 100 mg of each compound was dissolved in 20 ml of acetonitrile and was uniformly spread on steel plates to a thickness of approximately 0.1 mm. The plates were then immediately exposed to a medium pressure 1200 watt high intensity quartz arc mercury discharge lamp (Conrad-Hanovia, Inc., Newark, N.J.) at a distance of 30 cm from the lamp. The light fastness results of these compounds are summarized in Table 7.

TABLE 7

| Cyclodextrin Compound | Fade Time |
|---|---|
| Dehydroxy Compound | >10 min[a] |
| Hydroxy Compound | <20 sec |

[a]There is a phase change after 10 minutes due to extreme heat

EXAMPLE 24

This example describes the preparation of films consisting of colorant, ultraviolet radiation transorber, and thermoplastic polymer. The colorant and ultraviolet radiation transorber were ground separately in a mortar. The desired amounts of the ground components were weighed and placed in an aluminum pan, along with a weighed amount of a thermoplastic polymer. The pan was placed on a hot plate set at 150° C. and the mixture in the pan was stirred until molten. A few drops of the molten mixture were poured onto a steel plate and spread into a thin film by means of a glass microscope slide. Each steel plate was 3×5 inches (7.6 cm×12.7 cm) and was obtained from Q-Panel Company, Cleveland, Ohio. The film on the steel plate was estimated to have a thickness of the order of 10–20 micrometers.

In every instance, the colorant was Malachite Green oxalate (Aldrich Chemical Company, Inc., Milwaukee, Wis.), referred to hereinafter as Colorant A for convenience. The ultraviolet radiation transorber ("UVRT") consisted of one or more of Irgacure® 500 ("UVRT A"), Irgacure® 651 ("UVRT B"), and Irgacure® 907 ("UVRT C"), each of which was described earlier and is available from Ciba-Geigy Corporation, Hawthorne, N.Y. The polymer was one of the following: an epichlorohydrin-bisphenol A epoxy resin ("Polymer A"), Epon® 1004F (Shell Oil Company, Houston, Tex.); a poly(ethylene glycol) having a weight-average molecular weight of about 8,000 ("Polymer B"), Carbowax 8000 (Aldrich Chemical Company); and a poly (ethylene glycol) having a weight-average molecular weight of about 4,600 ("Polymer C"), Carbowax 4600 (Aldrich Chemical Company). A control film was prepared which consisted only of colorant and polymer. The compositions of the films are summarized in Table 8.

TABLE 8

Compositions of Films Containing
Colorant and Ultraviolet Radiation Transorber ("UVRT")

| Film | Colorant Type | Parts | UVRT Type | Parts | Polymer Type | Parts |
|---|---|---|---|---|---|---|
| A | A | 1 | A | 6 | A | 90 |
|   |   |   | C | 4 |   |   |
| B | A | 1 | A | 12 | A | 90 |
|   |   |   | C | 8 |   |   |
| C | A | 1 | A | 18 | A | 90 |
|   |   |   | C | 12 |   |   |
| D | A | 1 | A | 6 | A | 90 |
|   |   |   | B | 4 |   |   |
| E | A | 1 | B | 30 | A | 70 |
| F | A | 1 | — | — | A | 100 |
| G | A | 1 | A | 6 | B | 90 |
|   |   |   | C | 4 |   |   |
| H | A | 1 | B | 10 | C | 90 |

While still on the steel plate, each film was exposed to ultraviolet radiation. In each case, the steel plate having the film sample on its surface was placed on a moving conveyor belt having a variable speed control. Three different ultraviolet radiation sources, or lamps, were used. Lamp A was a 222-nanometer excimer lamp and Lamp B was a 308-nanometer excimer lamp, as already described. Lamp C was a fusion lamp system having a "D" bulb (Fusion Systems Corporation, Rockville, Md.). The excimer lamps were organized in banks of four cylindrical lamps having a length of about 30 cm, with the lamps being oriented normal to the direction of motion of the belt. The lamps were cooled by circulating water through a centrally located or inner tube of the lamp and, as a consequence, they operated at a relatively low temperature, i.e., about 50° C. The power density at the lamp's outer surface typically is in the range of from about 4 to about 20 joules per square meter ($J/m^2$).

However, such range in reality merely reflects the capabilities of current excimer lamp power supplies; in the future, higher power densities may be practical. With Lamps A and B, the distance from the lamp to the film sample was 4.5 cm and the belt was set to move at 20 ft/min (0.1 m/sec). With Lamp C, the belt speed was 14 ft/min (0.07 m/sec) and the lamp-to-sample distance was 10 cm. The results of exposing the film samples to ultraviolet radiation are summarized in Table 9. Except for Film F, the table records the number of passes under a lamp which were required in order to render the film colorless. For Film F, the table records the number of passes tried, with the film in each case remaining colored (no change).

TABLE 9

Results of Exposing Films Containing
Colorant and Ultraviolet Radiation Transorber (UVRT)
to Ultraviolet Radiation
Excimer Lamp

| Film | Lamp A | Lamp B | Fusion Lamp |
|------|--------|--------|-------------|
| A    | 3      | 3      | 15          |
| B    | 2      | 3      | 10          |
| C    | 1      | 3      | 10          |
| D    | 1      | 1      | 10          |
| E    | 1      | 1      | 1           |
| F    | 5      | 5      | 10          |
| G    | 3      | —      | 10          |
| H    | 3      | —      | 10          |

EXAMPLE 25

This Example demonstrates that the 222 nanometer excimer lamps illustrated in FIG. 14 produce uniform intensity readings on a surface of a substrate 5.5 centimeters from die lamps, at the numbered locations, in an amount sufficient to mutate the colorant in the compositions of the present invention which are present on the surface of the substrate. The lamp 10 comprises a lamp housing 15 with four excimer lamp bulbs 20 positioned in parallel, the excimer lamp bulbs 20 are approximately 30 cm in length. The lamps are cooled by circulating water through a centrally located or inner tube (not shown) and, as a consequence, the lamps are operated at a relatively low temperature, i.e., about 50° C. The power density at the lamp's outer surface typically is in the range of from about 4 to about 20 joules per square meter (j/m$^2$).

Table 10 summarizes the intensity readings which were obtained by a meter located on the surface of the substrate. The readings numbered 1, 4, 7, and 10 were located approximately 7.0 centimeters from the left end of the column as shown in FIG. 14. The readings numbered 3, 6, 9, and 12 were located approximately 5.5 centimeters from the right end of the column as shown in FIG. 14. The readings numbered 2, 5, 8, and L1 were centrally located approximately 17.5 centimeters from each end of the column as shown in FIG. 14.

TABLE 10

| Background ($\mu$W) | Reading (mW/cm$^2$) |
|---------------------|---------------------|
| 24.57               | 9.63                |
| 19.56               | 9.35                |
| 22.67               | 9.39                |
| 19.62               | 9.33                |
| 17.90               | 9.30                |
| 19.60               | 9.30                |
| 21.41               | 9.32                |

TABLE 10-continued

| Background ($\mu$W) | Reading (mW/cm$^2$) |
|---------------------|---------------------|
| 17.91               | 9.30                |
| 23.49               | 9.30                |
| 19.15               | 9.36                |
| 17.12               | 9.35                |
| 21.44               | 9.37                |

EXAMPLE 26

This Example demonstrates that the 222 nanometer excimer lamps illustrated in FIG. 15 produce uniform intensity readings on a surface of a substrate 5.5 centimeters from the lamps, at the numbered locations, in an amount sufficient to mutate the colorant in the compositions of the present invention which are present on the surface of the substrate. The excimer lamp 10 comprises a lamp housing 15 with four excimer lamp bulbs 20 positioned in parallel, the excimer lamp bulbs 20 are approximately 30 cm in length. The lamps are cooled by circulating water through a centrally located or inner tube (not shown) and, as a consequence, the lamps are operated at a relatively low temperature, i.e., about 50° C. The power density at the lamp's outer surface typically is in the range of from about 4 to about 20 joules per square meter (J/m$^2$).

Table 11 summarizes the intensity readings which were obtained by a meter located on the surface of the substrate. The readings numbered 1, 4, and 7 were located approximately 7.0 centimeters from the left end of the columns as shown in FIG. 15. The readings numbered 3, 6, and 9 were located approximately 5.5 centimeters from the right end of the columns as shown in FIG. 15. The readings numbered 2, 5, 8 were centrally located approximately 17.5 centimeters from each end of the columns as shown in FIG. 15.

TABLE 11

| Background ($\mu$W) | Reading (mW/cm$^2$) |
|---------------------|---------------------|
| 23.46               | 9.32                |
| 16.12               | 9.31                |
| 17.39               | 9.32                |
| 20.19               | 9.31                |
| 16.45               | 9.29                |
| 20.42               | 9.31                |
| 18.33               | 9.32                |
| 15.50               | 9.30                |
| 20.90               | 9.34                |

EXAMPLE 27

This Example demonstrates the intensity produced by the 222 nanometer excimer lamps illustrated in FIG. 16, on a surface of a substrate, as a function of the distance of the surface from the lamps, the intensity being sufficient to mutate the colorant in the compositions of the present invention which are present on the surface of the substrate. The excimer lamp 10 comprises a lamp housing 15 with four excimer lamp bulbs 20 positioned in parallel, the excimer lamp bulbs 20 are approximately 30 cm in length. The lamps are cooled by circulating water through a centrally located or inner tube (not shown) and, as a consequence, the lamps are operated at a relatively low temperature, i.e., about 50° C. The power density at the lamp's outer surface typically is in the range of from about 4 to about 20 joules per square meter (J/m$^2$).

Table 12 summarizes the intensity readings which were obtained by a meter located on the surface of the substrate at position 1 as shown in FIG. 16. Position 1 was centrally located approximately 17 centimeters from each end of the column as shown in FIG. 16.

TABLE 12

| Distance (cm) | Background ($\mu$W) | Reading (mW/cm$^2$) |
|---|---|---|
| 5.5 | 18.85 | 9.30 |
| 6.0 | 15.78 | 9.32 |
| 10 | 18.60 | 9.32 |
| 15 | 20.90 | 9.38 |
| 20 | 21.67 | 9.48 |
| 25 | 19.86 | 9.69 |
| 30 | 22.50 | 11.14 |
| 35 | 26.28 | 9.10 |
| 40 | 24.71 | 7.58 |
| 50 | 26.95 | 5.20 |

EXAMPLE 28

This example describes a method of making the following wavelength-selective sensitizer as represented by the following formula:

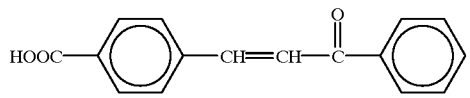

The wavelength-selective sensitizer is synthesized as summarized below:

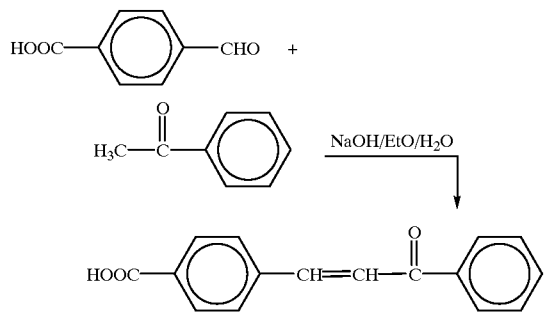

In a 250 ml round bottom flask fitted with a magnetic stir bar, and a condenser, was added 10.8 g (0.27 mole) sodium hydroxide (Aldrich), 98 g water and 50 g ethanol. The solution was stirred while being cooled to room temperature in an ice bath. To the stirred solution was added 25.8 g (0.21 mole) acetophenone (Aldrich) and then 32.2 g (0.21 mole) 4-carboxybenzaldehyde (Aldrich). The reaction mixture was stirred at room temperature for approximately 8 hours. The reaction mixture temperature was checked in order to prevent it from exceeding 30° C. Next, dilute HCL was added to bring the mixture to neutral pH. The white/yellow precipitate was filtered using a Buchner funnel to yield 40.0 g (75%) after drying on a rotary pump for four hours. The product was used below without further purification.

The resulting reaction product had the following physical parameters:

Mass. Spec. m/e (m$^+$) 252, 207, 179, 157, 105, 77, 51.

EXAMPLE 29

This example describes a method of covalendy bonding the compound produced in Example 28 to cyclodextrin as summarized by the following reaction:

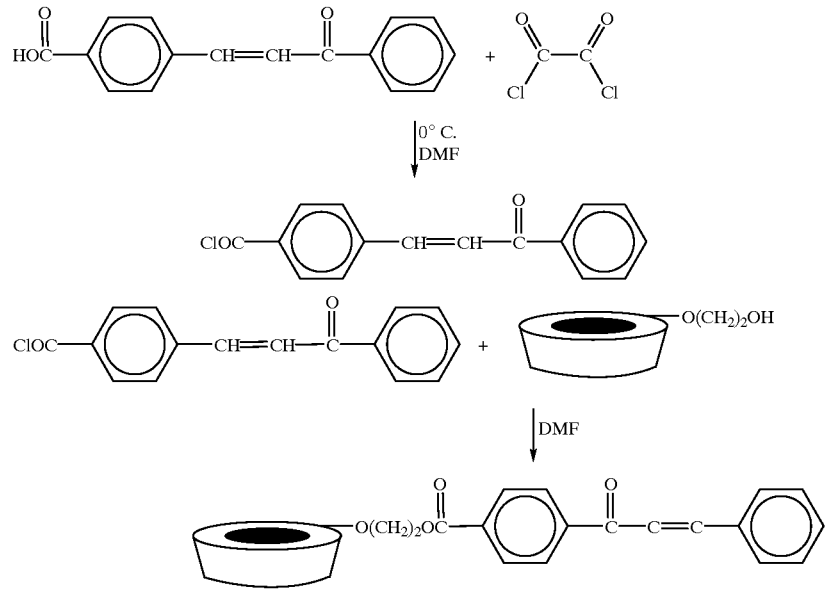

To a 250 ml round bottom flask fitted with a magnetic stir bar, condenser, and while being flushed with argon, was placed 5.0 g (0.019 mole) of the composition prepared in Example 29, and 50 ml of anhydrous DMF (Aldrich). To this solution was slowly dropped in 2.5 g (0.019 mole) oxalyl chloride (Aldrich) over thirty minutes with vigorous stirring while the reaction flask was cooled in an ice-bath. After one hour, the reaction was allowed to warm to room temperature, and then was stirred for one hour. The reaction mixture was used "as is" in the following step. To the above reaction mixture 5.3 g (0.004 mole) of hydroxyethyl substituted alpha-cyclodextrin (American Maize Company), dehydrated by Dean and Stark over benzene for two hours to remove any water, was added and the reaction mixture stirred at room temperature with 3 drops of triethylamine added. After four hours the reaction mixture was poured into 500 ml of acetone and the white precipitate filtered using a Buchner Funnel. The white powder was dried on a rotary pump (0.1 mm Hg) for four hours to yield 8.2 g product.

The resulting reaction product had the following physical parameters:

NMR (DMSO-d6) 2.80[M, CD], 3.6–4.0 [M, CD], 7.9 [C, aromatus],8.2 [M, aromatus of C], 8.3 [M, aromatus of C] ppm.

EXAMPLE 30

This example describes a method of making the wavelength-selective sensitizer, namely 4-[4'-carboxy phenyl]-3-buten-2-one as represented by the following formula:

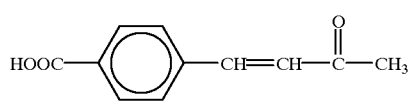

The wavelength-selective sensitizer is synthesized as summarized below:

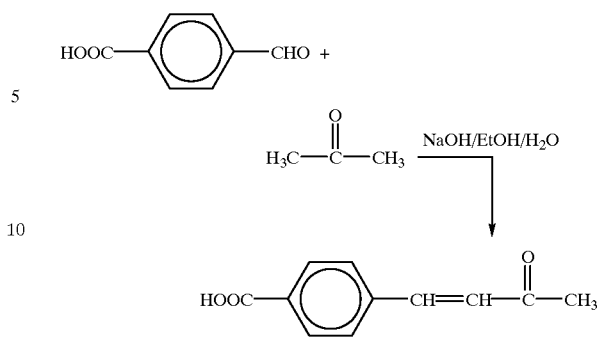

The method of Example 28 was followed except that acetone (Fisher, Optima Grade) was added first, and then the carboxybenzaldehyde was added. More particularly, 32.2 (0.21 mole) of carboxybenzaldehyde was reacted with 12.2 g (0.21 mole) of acetone in the sodium hydroxide/ethanol/water mixture described in Example 28. Dilute HCl was added to bring the reaction mixture to neutral pH, yielding 37.1 g (91%) of a pale yellow powder which was used without further purification in the following examples.

The resulting reaction product, namely 4[4'-carboxy phenyl]-3-buten-2-one, had the following physical parameters:

Mass. Spec. 190 (m$^+$), 175, 120.

EXAMPLE 31

This example describes a method of covalently bonding the 4-[4'-carboxy phenyl]-3-buten-2-one produced in Example 30 to cyclodextrin as is summarized below:

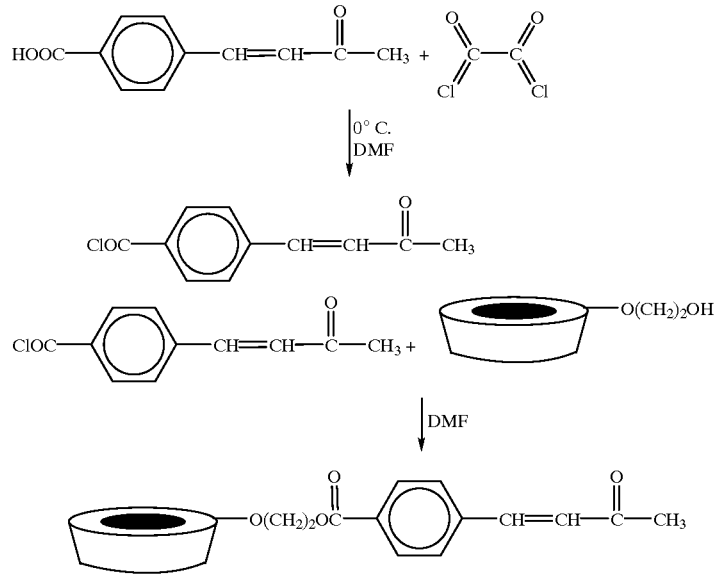

The method of Example 29 was followed except that 5.0 g of the 4-[4'-carboxy phenyl]-3-buten-2-one was used. More particularly, 5.0 g (0.026 mole) of the 4-[4'-carboxy phenyl]-3-buten-2-one produced in Example 30 was reacted with 3.3 g (0.026 mole) of oxalyl chloride in anyhydrous DMF at about 0° C. Next, approximately 7.1 g (0.005 mole) hydroxyethyl substituted cyclodextrin was added to the mixture (5:1 ratio) under the conditions described in Example 30 and was further processed as described therein, to produce 10.8 g of white powder. The NMR of the product showed both the aromatic protons of the 4-[4'-carboxy phenyl]-3-buten-2-one produced in Example 30 and the glucose protons of the cyclodextrin.

EXAMPLE 32

This example describes a method of covalently bonding the compound produced in Example 28 to a photoreactor, namely DARCUR 2959, as is summarized below:

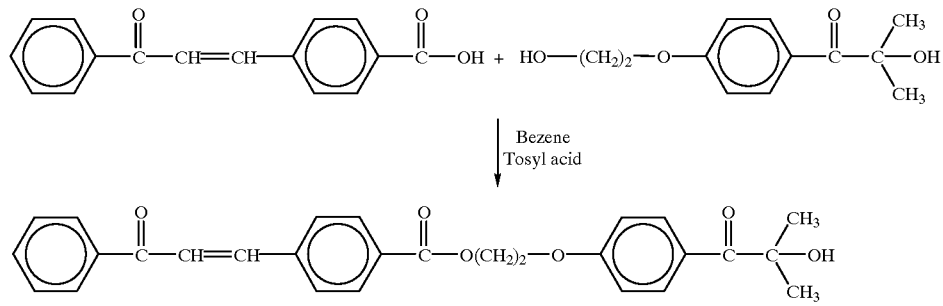

To a 500 ml round bottom flask fitted with a magnetic stir bar, and condenser, was placed 20 g (0.08 mole) of the composition prepared in Example 28, 17.8 g (0.08 mole) DARCUR 2959 (Ciba-Geigy, N.Y.), 0.5 g p-toluenesulphonic acid (Aldrich), and 300 ml anhydrous benzene (Aldrich). The Dean and Stark adapter was put on the flask and the reaction mixture heated at reflux for 8 hours after which point 1.5 ml of water had been collected (theo. 1.43 ml). The reaction mixture was then cooled and the solvent removed on a rotary evaporator to yield 35.4 g. The crude product was recrystallized from 30% ethyl acetate in hexane to yield 34.2 g (94%) of a white powder. The resulting reaction product had the following physical parameters:

Mass. Spectrum: 458 ($m^+$), 440, 399, 322, 284.

EXAMPLE 33

To determine whether the 4-[4'-carboxy phenyl]-3-buten-2-one produced in Example 30 has the capability to stabilize colorants, the following experiment was conducted. Test films were made up containing 90% carbowax 4600 and 10% of a 1 part Victoria Pure Blue BO (Aldrich) to 19 parts 4-[4'-carboxy phenyl]-3-buten-2-one. The mixture was melted on a hot plate, stirred, then drawn down on metal plates (at approximately 60° C.), using a #3 drawdown bar. A similar sample was made with only 1% Victoria Pure Blue BO in 99% carbowax.

The plates were exposed to a 1200 Watt Mercury medium pressure lamp for one hour, the lamp being about 2 feet from the plates. After one hour, the Victoria Pure Blue BO plate was essentially colorless, while the plate having the mixture of Victoria Pure Blue BO and 4-[4'-carboxy phenyl]-3-buten-2-one thereon had not changed.

EXAMPLE 34

A further experiment to determine the colorant stabilizing capability of the 4-[4'-carboxy phenyl]-3-buten-2-one produced in Example 30 is as follows. The experiment used in Example 33 was repeated except that no carbowax was used. Instead, the materials were dissolved in acetonitrile and a film formed, allowed to dry, and then exposed to the 1200 Watt lamp. Again, after one hour, the dye (Victoria Pure Blue BO) was essentially colorless while the mixture containing the 4-[4'-carboxy phenyl]-3-buten-2-one was unchanged in color.

EXAMPLE 35

A further experiment to determine the colorant stabilizing capability of the compounds produced in Examples 28, 29, 30 (4-[4'-carboxy phenyl]-3-buten-2-one), and 31 (4-[4'-carboxy phenyl]-3-buten-2-one/cyclodextrin) was as follows. The experiment used in Example 34 was repeated for all four compounds, separately. More particularly, five metal plates were prepared using the acetonitrile slurry method of Example 34, with the compositions as follows:

(1) Victoria Pure Blue BO only;
(2) Victoria Pure Blue BO + the compound produced in Example 28;
(3) Victoria Pure Blue BO + the compound produced in Example 30;
(4) Victoria Pure Blue BO + the compound produced in Example 29;
(5) Victoria Pure Blue BO + the compound produced in Example 31.

In compositions (2) through (5), the compositions contained one part Victoria Pure Blue BO per 20 parts of the compounds produced in the above examples. More particularly, 0.1 g of Victoria Pure Blue BO was mixed with approximately 2.0 g of one of the compounds produced in the above examples, in 10 ml of acetonitrile. The mixtures were drawn down using a #8 bar and allowed to air dry in a ventilation hood. All of the plates were simultaneously exposed to the 1200 Watt mercury lamp for one hour. Each plate was half covered with aluminum foil during exposure to the lamp to maintain a reference point with respect to fading of the colorant. After one hour under the lamp, mixture (1) had gone colorless, while mixtures (2) through (5) all remained unchanged.

EXAMPLE 36

Another experiment to determine the colorant stabilizing capability of the compound produced in Example 29 was as follows. Briefly described, the compound of Example 29 was used with color inks removed from the color cartridges of a CANON BJC-600e bubble jet color printer. The ink was reinstalled into the cartridges, which were installed into the ink jet printer, and color test pages were generated. The fortieth color test page was used in the present study.

More particularly, the four cartridges were BJI-201, and the four inks (cyan, magenta, black, and yellow) were prepared as follows:

(1) Cyan

About 3.8 ml of the colored ink in the cartridge was removed, having a viscosity of 12 seconds for 3 ml measured in a 10 ml pipette. About 0.4 g of the compound produced in Example 29 was added to the 3.8 ml and mixed for 15 minutes. The ink solution prepared was hazy, and had a viscosity of 19 seconds for 3 ml.

(2) Magenta

About 4.8 ml of the colored ink in the cartridge was removed, having a viscosity of 12 seconds for 3 ml. About 0.43 g of the compound of Example 29 was added to the 4.8 ml and mixed for fifteen minutes, producing a ink solution having a viscosity of 18 seconds for 3 ml.

(3) Black

About 7.2 ml of the ink in the cartridge was removed, having a viscosity of 8 seconds for 3 ml. About 0.72 g of the compound of Example 29 was added to the 7.2 ml and mixed for fifteen minutes, producing a hazy ink solution having a viscosity of 15 seconds for 3 ml.

(4) Yellow

About 4.0 ml of the colored ink in the cartridge was removed, having a viscosity of 4 seconds for 3 ml. About 0.41 g of the compound of Example 29 was added to the 4.0 ml and mixed for fifteen minutes, producing a hazy ink solution having a viscosity of 7 seconds for 3 ml.

The cartridges were then refilled with the corresponding ink solutions (1) through (4) above. Forty pages were run off, and the fortieth page was exposed to a 1200 Watt medium pressure mercury lamp with a control sheet for nine hours. The control sheet is the fortieth color test page run off using the ink compositions that were in the original ink cartridges.

The results of this experiment are as follows. After three hours under the 1200 Watt lamp, the control was 40 to 50% bleached, while the inks containing the compound produced in Example 29 were unchanged. After nine hours, the control was 50 to 60% bleached while the inks containing the compound of Example 29 were only about 10 to 20% bleached. Accordingly, the compound produced in Example 29 is capable of stabilizing the dyes found in standard ink jet inks.

EXAMPLE 37

Another experiment to determine the colorant stabilizing capability of the compound produced in Example 29 is as follows. The stability of the ink solutions produced in Example 28 were studied as described below.

The forty-eighth sheet (test sheet) was generated using the ink solutions (1) through (4) of Example 36 each containing about 10% of the compound of Example 29, and was then exposed to a 1200 Watt lamp along with a control sheet (generated from the commercially available ink from the cartridges before the compound of Example 29 was added). The sheets were monitored each hour of exposure and "fade" was determined by the eye against an unexposed sheet. The results of exposing the sheets to the 1200 Watt lamp are summarized in Table 13, where NC=no change.

TABLE 13

| Time (Hour) | Irradiation | |
| --- | --- | --- |
| | Control Sheet | Test Sheet |
| 0 | NC | NC |
| 1 | 5–10% | NC |

TABLE 13-continued

| Time (Hour) | Irradiation | |
| --- | --- | --- |
| | Control Sheet | Test Sheet |
| 2 | 10–15% | NC |
| 3 | 20% | NC |
| 4 | 30% | NC |
| 5 | 50% | NC |

Accordingly, the compound prepared in Example 29 works well as a dye stabilizer to visible and ultraviolet radiation.

Applications of the Mutable Colorant Composition

As discussed above, the mutable colorant composition of the present invention has a variety of useful applications such as temporary marking, ultraviolet radiation indication, and printing on plastic articles. Particular embodiments of these uses are described below and are illustrated in FIGS. 3–12.

Photoerasable Markings

The mutable colorant composition of the present invention can be used for temporary printing of markings such as labels, tags, tickets, stickers, and the like. This is advantageous for temporary printing of price markings, particularly for gift items where the buyer would like to conceal the price from the recipient. A typical marking comprises a substrate such as paper, cardboard, or plastic and is first printed with indicia indicating a price using the mutable colorant composition of the present invention. The indicia can be any image, but for price markings is normally in the form of alpha-numeric characters. When the marked product is purchased, the price on the marking is erased with ultraviolet radiation of the necessary wavelength and dosage. For example, convenient places for an ultraviolet lamp to erase price labels would be at a customer check-out counter or at a gift wrap counter.

Price markings printed with the mutable colorant composition of the present invention could also be useful when retailers change prices. In such a case, the store clerk would photoerase the original price on the marking, and print the new price with the mutable colorant composition of the present invention. This allows for instant price change and saves the cost of applying a new marking for each price change.

The price can be printed on labels with the colorant composition of the present invention using conventional methods of printing such as stamping. The markings may also contain nonphotoerasable printing with non-mutable colorants to indicate a brand name or logo or the name of the seller. Such indicia would remain after photoerasing the price.

Figure 3:
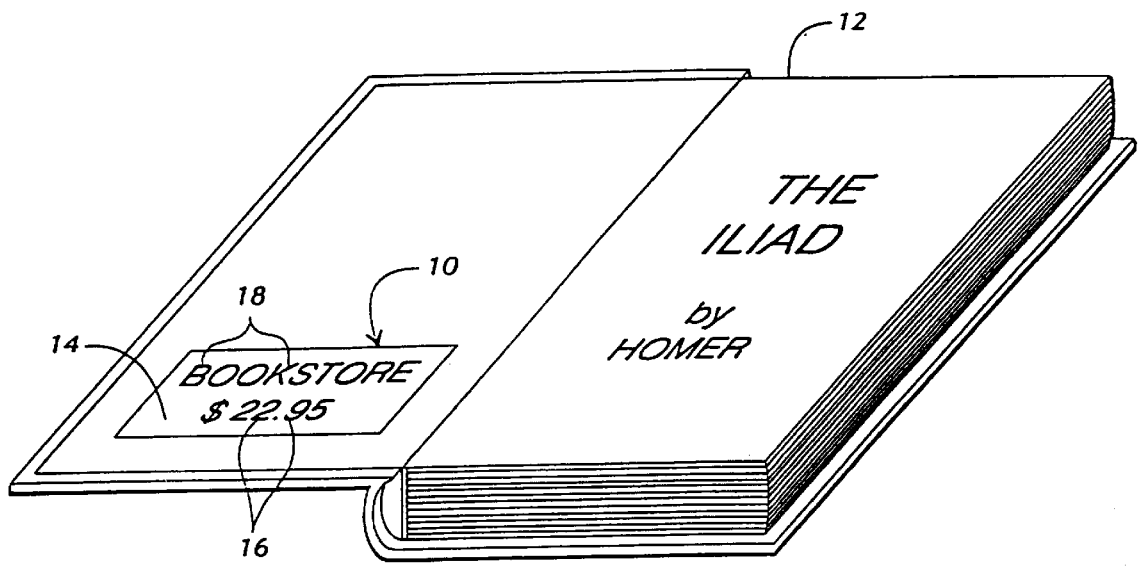
FIG. 3 is a perspective view of a book marked with a photoerasable price marking made according to an embodiment of the present invention.

FIG. 3 illustrates a label 10 adhered to a book 12. The label comprises a substrate 14, which in this embodiment is adhesive paper, and indicia 16 on the substrate surface visually indicating a price. The indicia 16 showing the price is defined by the mutable colorant composition of the present invention. The label also includes indicia 18 indicating the name of the store which sells the book 12. This indicia 18 is printed with non-erasable ink.

Figure 4:
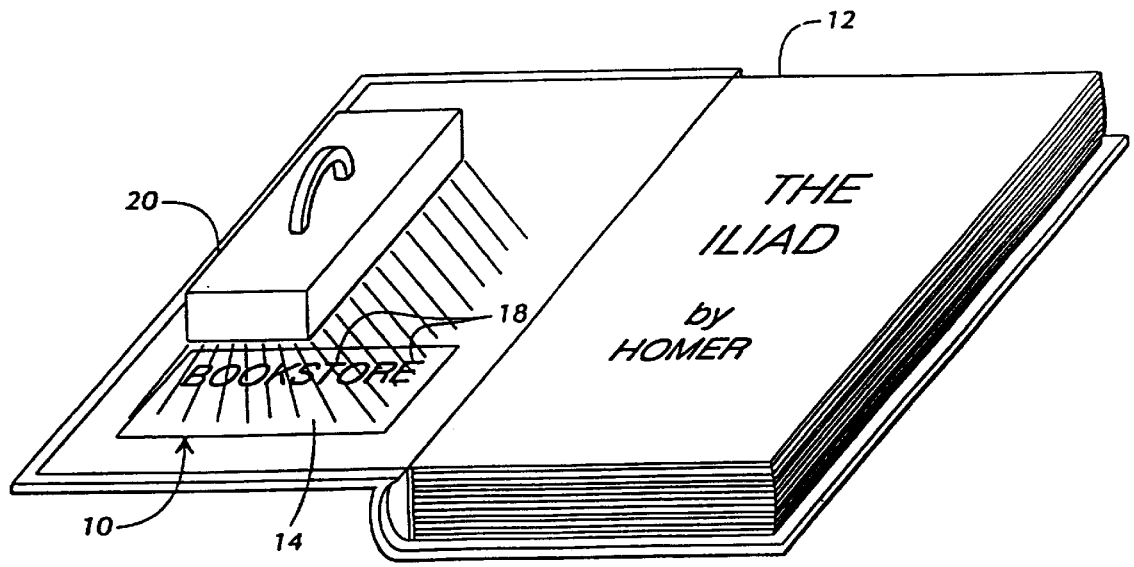
FIG. 4 is a perspective view of the book shown in FIG. 3 and illustrates the irradiation of the marking and photoerasure of the price thereon with an excimer lamp.

FIG. 4 illustrates photoerasure of the indicia 16 indicating the price on the label 10 using incoherent, pulsed ultraviolet radiation emitted from a dielectric barrier discharge excimer lamp 20.

Documents with Concealed Information

Another application of the mutable color composition of the present invention is in the communication of concealed information. For example, a written message which is to be confidentially communicated can be overprinted with a layer of the mutable color composition of the present invention. After delivery of the document, the overprinting layer can be photoerased to reveal the message. A particularly advantageous application of this concept is to gaming tickets wherein the status of the player is concealed by a layer of opaque overprinting. Conventional gaming tickets of this type typically comprise a paper or cardboard substrate printed with the status of the player and a opaque layer of metalized coating over the printing to conceal the player's status until the player purchases the gaming ticket and manually removes the metalized coating. The metalized coating is typically removed by scratching the coating off with a tool such as a coin.

Figure 5:
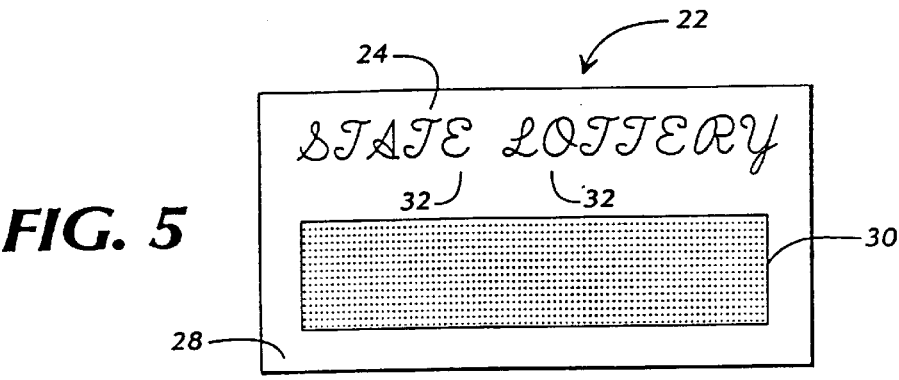
FIG. 5 is a gaming ticket made in accordance with an embodiment of the present invention.
Figure 6:
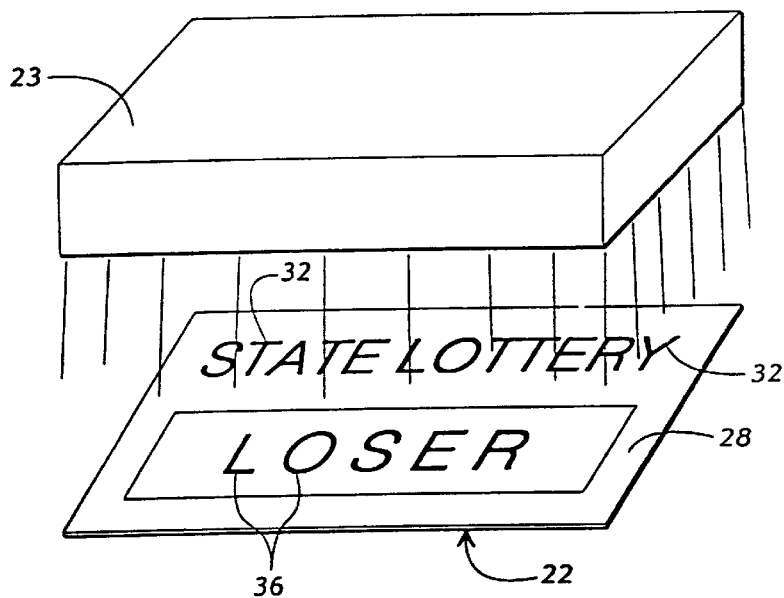
FIG. 6 is a perspective view of the gaming ticket shown in FIG. 5 and illustrates photoerasure of the opaque overprinting layer covering the non-erasable indicia indicating the status of the player.

A gaming ticket 22 made according to an embodiment of the present invention is shown in FIGS. 5 and 6 and comprises a cardboard substrate 24, non-erasable indicia 26 printed on a surface 28 of the ticket for communicating the status of the player, and an opaque layer 30 of overprinting on the surface of the substrate covering the non-erasable indicia 26. The gaming ticket 22 also comprises additional non-erasable indicia 32 which, in this case, indicates the particular game being played. The overprinting layer 30 comprises the mutable colorant composition of the present invention and as such is initially opaque to conceal the status of the player, but upon irradiation with ultraviolet radiation from a source such as a dielectric barrier discharge excimer lamp 23, irreversibly mutates and becomes substantially colorless. The overprinting layer 30 then becomes invisible and the status of the player is revealed. The lamp 23 can be placed conveniently at or near the place of purchase of the gaming ticket 22 so that the player can immediately find out his or her status without the inconvenience of scratching off a coating.

Suitable substrates 24 for a gaming ticket or any other type of document communicating concealed information include paper, cardboard, plastic, and the like. The gaming ticket 22 or other document can include non-erasable indicia of any type, but typically will be alphanumeric characters. The non-erasable indicia 26 to be concealed desirably should be of the same color as the overprinting layer 30. For example, an overprinting layer 30 comprising a blue mutable colored composition in combination with non-erasable indicia 26 printed with blue non-erasable ink would be particularly secure.

Photoerasable Paint

Still another application of the mutable colorant composition of the present invention is photoerasable paints for temporary marking of a variety of substrates such as signs, particularly road signs, trees, roads, sidewalks, buildings, and terrain, for example to indicate circumstances such as "work being done", "detours", "dangerous conditions", and the like. Uses of the photoerasable paint of the present invention include use by surveyors, road and construction crews, use in crime investigations and at crime scenes, agricultural uses such as marking the divisions of fields and the crops to be planted within such boundaries, and the labeling of trees to be cut in selective lumber production programs. The photoerasable paint of the present invention can be used to temporarily cover messages printed with non-erasable paint as well as to provide a new message. The photoerasable paint can have a variety of colors and is stable to sunlight The photoerasable paint can be erased by irradiating the paint with ultraviolet radiation at a dosage level sufficient to irreversibly mutate the color. However, because the mutable colorant is stable to sunlight, the markings will not fade outdoors until intentionally erased using radiation at the appropriate wavelength and dosage level. The photoerasable paint of the present invention allows for temporary marking and removal of that marking without the need for washing, abrasion, or chemical attack.

The photoerasable paint of the present invention comprises a colorant vehicle which is transparent to ultraviolet radiation and the mutable colorant composition of the present invention dispersed in the vehicle. There are a variety of suitable paint vehicles including latex, alkyd resins, polyurethane resins, acrylic resins, silicone resins, phenolic resins, nitrocellulose, epoxy resins, cellulose acetates and butyrates, natural oils, and the like. As understood by those skilled in the art, the photoerasable paint of the present invention may also include other additives such as surfactants and solvents.

When photoerasable paint is used to cover prior non-erasable markings, it may be desirable to increase the opacity of the photoerasable paint by adding a non-erasable pigment. For example, a titanium dioxide opacifier may be suitable for incorporation into photoerasable paint on some surfaces where a white residual would be acceptable. It may also may be desirable under some circumstances to make a color changing paint which is possible by dispersing both a photoerasable colorant and a nonphotoerasable colorant having different colors. Upon exposure to ultraviolet light having the appropriate wavelength and dosage, the photoerasable colorant would be colorless, leaving the non-erasable colorant and effecting a color change.

Marking Instruments containing Photoerasable Compositions

Another application of the mutable color composition of the present invention is in writing or marking instruments such as pens and wick or felt tip markers, such as magic markers and highlighters. Markers using the mutable colorant composition of the present invention allow temporary marking which can be erased by irradiation with ultraviolet light having the appropriate wavelength and dosage. For example, highlighters using ink, including the mutable colorant composition of the present invention, can be used to highlight text in books. When resale of a book is desired, the highlighting can be erased by exposing the highlighted areas to ultraviolet radiation. The highlighted areas, however, would be stable to sunlight and artificial lighting. Another use of the mutable color composition of the present invention includes pens containing such a composition, wherein the notations made by the pens could be erased by irradiation thereby avoiding the need to shred high security documents, or thereby avoiding the need for chemically or mechanically removing such a composition during a recycling process.

The marking instrument of the present invention comprises a marking fluid including a vehicle or carrier and the mutable colorant composition of the present invention. The particular mutable colorant and vehicle will depend on the particular application as is understood by those skilled in the art. Examples of suitable vehicles for marking fluid such as ink, include water, glycerol, alkylene glycols, other alcohols, and the like. The marking fluid may also comprise other additives known to those skilled in the art. Generally, the marking fluid for use in writing instruments of the present invention are of conventional formulation except that conventional pigments are replaced by the mutable colorant composition of the present invention.

The structure of the marking instrument of the present invention is also conventional and is not described in detail, but particular embodiments are generally illustrated in FIGS. 7 and 8. FIG. 7 shows a ballpoint pen cartridge 40 comprising a reservoir 42 containing ink and an applicator 46 having a ballpoint 48 extending from one end of the reservoir. The ink 44 containing the mutable colorant composition of the present invention is drawn by capillary action from the reservoir 42 through the ballpoint outlet 48 of the applicator 46 when the ballpoint is drawn across a writing surface.

A felt tip marker 50 is illustrated in FIG. 8 and comprises a reservoir 52, an absorbent fibrous material 54 disposed in the reservoir and containing the ink supply, a head 56 enclosing an open end of the reservoir, and a wick 58 extending from the absorbent fibrous material within the reservoir, through the head, and to a felt tip 60 which is the ink applicator.

It should be understood that the marking instrument of the present invention can take a variety of structural forms which are known to those skilled in the art. The foregoing embodiments shown in FIGS. 7 and 8 are for general illustration.

Ultraviolet Light Exposure Indicator

As mentioned above, the mutable colorant composition of the present invention is useful to indicate exposure to ultraviolet light. This is possible because the mutable colorant composition of the present invention comprises a mutable colorant that decolors upon exposure to ultraviolet light in a narrow wavelength range.

FIG. 9 illustrates an embodiment of an ultraviolet radiation exposure indicator 70 of the present invention. The indicator 70 comprises a film including the mutable colorant composition of the present invention disposed on a substrate 74. The indicator 70 is in the form of a strip and the substrate desirably comprises a strip of adhesive of paper or plastic. The film 72 comprises the mutable colorant composition of the present invention dispersed in a carrier or vehicle such a polymer. The carrier should be transparent to ultraviolet light. The film 72 has layers 76 of increasing thickness which varies from low to high across the strip. As the thickness of the film 72 increases, the mutable colorant density increases, thus forming a mutable colorant density gradient across the area of the film. The mutable colorant density is the amount of mutable colorant per area of the strip. Each level of increasing thickness forms regions having differing amounts of mutable colorant. The indicator 70 has thus regions of increasing colorant density. A given dose of ultraviolet radiation will decolorate at least a portion of the film 72 and the amount of the film decolored can be taken as an indication of the extent of exposure to ultraviolet radiation. The substrate 74 of the indicator 70 further includes a border 78 having indicia thereon for indicating the dosage of ultraviolet radiation to which the indicator is exposed. As will be understood to those skilled in the art, the strip will need to be calibrated to a particular source of ultraviolet radiation.

The indicator 70 can be attached with the adhesive substrate 74 to a surface that is exposed to ultraviolet radiations such as an arc welders helmet.

Printed Articles

Yet another application of the mutable colorant composition of the present invention is in the direct printing of articles such as plastic containers, plastic films, and paper. Generally, the printable colored article of the present invention comprises a substrate including a matrix and a mutable colorant composition dispersed in the matrix. As described in detail above, the mutable colorant composition of the present invention comprises a mutable colorant and an ultraviolet radiation transorber which, upon irradiation with ultraviolet radiation, interacts with the colorant to irreversibly mutate the colorant and render the colorant substantially colorless. An image can be printed on the substrate by irradiating selected portions of the substrates with ultraviolet radiation at a wavelength and dosage level sufficient to irreversibly mutable the colorant at the selected portions.

The substrate may further comprise multiple mutable colorant compositions each including a mutable colorant and an ultraviolet radiation transorber. Each mutable colorant has a color and the colors are different from one another before mutation. Each colorant is mutable at different ultraviolet radiation wavelengths. Upon irradiation of selected portions of the substrate with ultraviolet radiation at the different wavelengths and at dosage levels sufficient to irreversibly mutate the colorants, multi-color images can be printed on the articles corresponding to the selected portions. The article is desirably printed by irradiating the substrate with incoherent, pulsed ultraviolet radiation emitted from a dielectric barrier discharge excimer lamp. The substrate can be directly printed with a mask having openings corresponding to the image desired to be printed. The openings in the mask direct the ultraviolet radiation to the selected portions of the substrate. High resolution printing, particularly on highly contoured surfaces, may require controlled sweeping of a tightly focused beam of ultraviolet radiation such as from an excimer laser. For example, electrophotography techniques can be used to irradiate the selected portions of the plastic article to create the desired image. Corresponding pending U.S. patent application Ser. No. 08/258,858, now abandoned, discloses techniques for using mutable colorants in electrophotography and is expressly incorporated herein by reference. Photoerasing can be conducted in two or more stages or can be done simultaneously with the appropriate excimer ultraviolet lamps to achieve multicolor effects.

For example, the colored article for printing can be a white sheet of paper, and the paper can also be the substrate and matrix of the article. If the paper comprises two mutable colorants, one blue before mutation and the other red before mutation, and corresponding ultraviolet radiation transorbers dispersed in the paper, selective photoerasing of the sheet of paper with ultraviolet radiation of the appropriate wavelengths could produce a sheet with regions of blue, red, violet, purple, and white.

Desirably, for full color printing, the matrix is colored with a mutable cyan colorant, a mutable magenta colorant, and a mutable yellow colorant, each of the colorants being mutable at a different wavelength of ultraviolet radiation. The matrix can take the form of a single layer comprising a mixture of all three colorants or could comprise three separate layers, each comprising a different colorant stacked one on top of the other. By directing radiation of a wavelength and dosage level suitable to mutate one of the colorants at a particular portion of the substrate, one of the colorants is erased, and a color which is a result of the remaining two colorants is left. The portion of the substrate that is exposed to all three wavelengths is clear. A portion of the substrate that is unexposed is black. Different colors are created at the remaining locations by exposing each location to a ultraviolet radiation at one or more wavelengths. For example, a location exposed to radiation wavelengths capable of mutating the cyan and yellow colorant would result in the location being magenta. This can be achieved by simultaneous exposure of selected portions of the substrate to ultraviolet radiation of the different wavelengths such as with three ultraviolet radiation excimer lasers or can be achieved by exposure of the substrate to ultraviolet radiation of different wavelengths in stages using three masks.

The article substrate may be clear, opaque, or translucent and may be colored with non-mutable (nonphotoerasable) colorants in addition to the mutable colorant so that when the mutable colorant is erased in selected portions, the selected portions have the color of the non-mutable colorant.

Suitable articles include a variety of items such as plastic containers, plastic films, and paper. Contoured or glossy plastic containers are particularly suitable articles as are transparent films for use in making transparencies or slides for visual projection. Suitable substrates include the article itself or a film adhered or otherwise attached to the article. Suitable matrix materials which form the substrate include the polymer of the plastic container or film or can be the paper when the substrate is a sheet of paper. The matrix should transmit a sufficient amount of ultraviolet light for mutation of the colorant. It is to be understood that the colorant composition of the present invention may be admixed with the matrix, and therefore is in the substrate, or it may be present as a layer on a surface of the substrate formed by the matrix. Colored plastic articles of the present invention alleviate the need for labels and adhesives and allow printing on contoured plastic surfaces and glossy plastic surfaces, which are not amenable to contact printing, labeling, or xerography.

Suitable matrix material can include a variety of polymers. The matrix polymer must transmit ultraviolet light, and suitable ones include gelatin, gelatin derivatives, cellulose derivatives, polysaccharides, polyvinyl compounds, acrylamide polymers, polymers of alkylacrylates and methacrylates, acrylic acid, sulfoalkylacrylates, poly (vinylbutyral), cellulose acetate, butyrate, poly (methylmethacrylate), ethylcellulose, polystyrene, poly (vinylchloride), polyiosbutylene, butadiene-styrene copolymers, vinyl chloride, polyvinyl alcohol, cellulose acetate hydrogenphthalate, and polyolefins such as polyethylene and polypropylene, and similar polymers.

According to a particular embodiment of the present invention, a color plastic article is provided comprising a plastic substrate comprising a first polymer, and a plastic first film laminated to the substrate and comprising a second polymer which transmits ultraviolet radiation, and the mutable colorant composition of the present invention dispersed in the second polymer. An image can be printed on the plastic article by irradiating selected portions of the first film with ultraviolet radiation at a wavelength and dosage level sufficient to irreversibly mutate the colorant at the selected portions. More particularly, in another embodiment of the present invention, a transparency comprises a first film laminated to a second film, the first film comprising the mutable colorant composition of the present invention. For multicolor effects, the second film can include a mutable colorant composition of another color.

Figure 10:
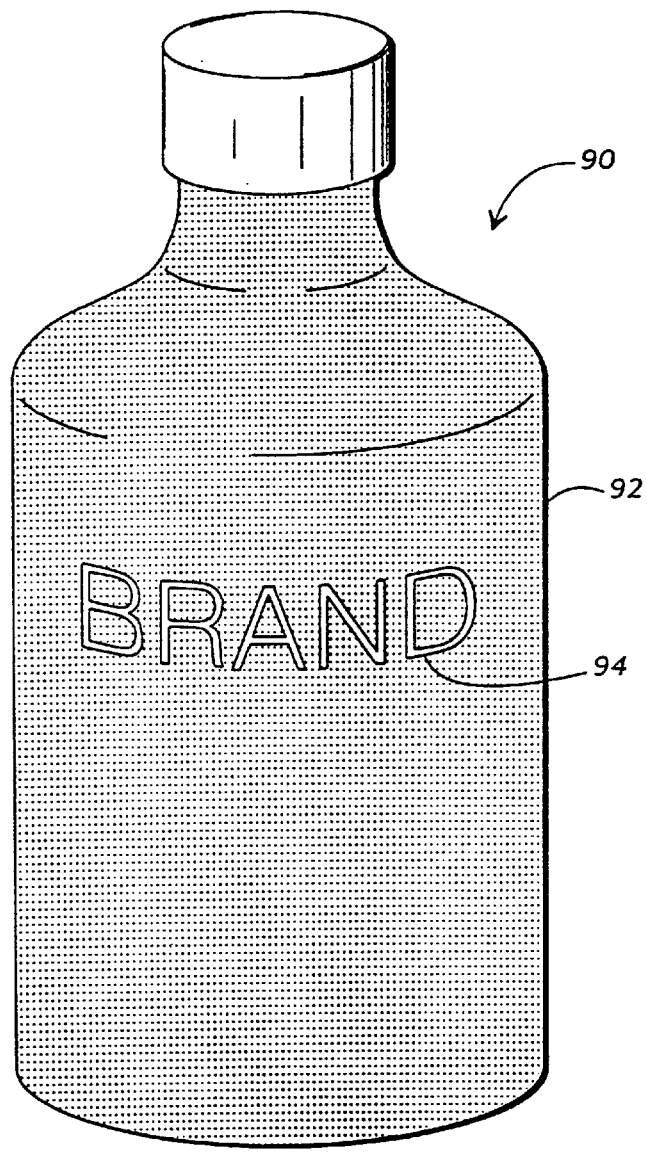
FIG. 10 is a printed plastic container made in accordance to an embodiment of present invention.

A printed plastic bottle 90 printed in accordance with an embodiment of the present invention is illustrated in FIG. 10. The bottle 90 is formed by a plastic substrate 92 which includes mutable colorant composition dispersed therein and has a printed image 94 formed therein by irradiating selected portions of the substrate with ultraviolet radiation.

Figure 11:
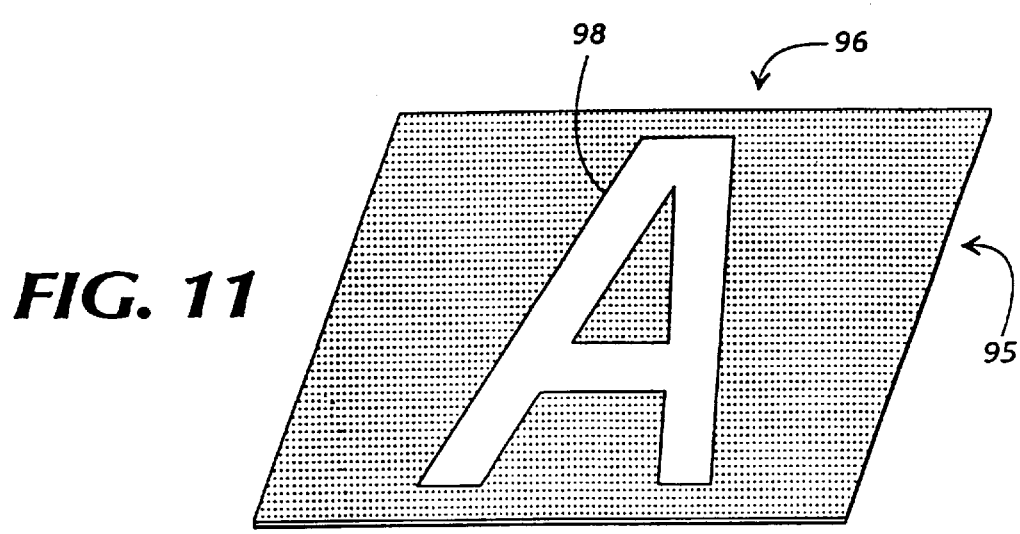
FIG. 11 is a direct printed transparency made in accordance with an embodiment of the present invention.

A transparency 95 printed in accordance with an embodiment of the present invention is illustrated in FIG. 11. The transparency 95 comprises a substrate 96 including a mutable colorant composition of the present invention dispersed therein and an image 98 formed therein by irradiating selected portions of the substrate with ultraviolet radiation. Transparencies such as the one shown in FIG. 11 can be made in a variety of sizes and can be used to generate banners, signs, bumper stickers, slides, and the like. The method of the present invention for producing slides allows a presenter to change and print slides just moments before a presentation. This process of the present invention can even be used to directly produce microfilm and microfiche materials.

Figure 12:
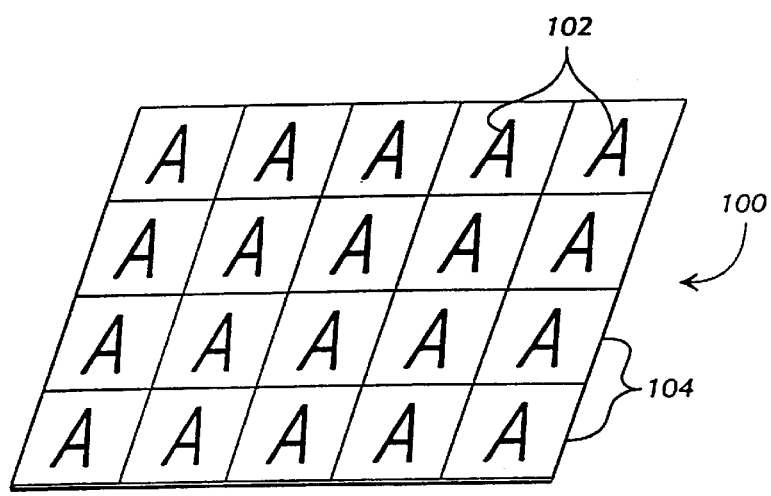
FIG. 12 is a printed transparency made in accordance with an embodiment of the present invention. This transparency is printed with multiple, discrete images for production of 35 mm slides.

FIG. 12 illustrates an embodiment of the present invention comprising a transparency 100 printed with a plurality of discrete images 102 on separate sections of the film 104 to form a plurality of slides such as 35 mm slides for visual projection. The printed slides are cut out of the film and mounted in slide holders. Using multiple mutable colorants or combinations of mutable colorants and a non-mutable colorant, multicolor slides can be produced in accordance with this process of the present invention.

Having thus described the invention, numerous changes and modifications hereof will be readily apparent to those having ordinary skill in the art, without departing from the spirit or scope of the invention.

What is claimed is:

1. A document comprising:

a substrate having a surface;

indicia on the surface; and an opaque layer covering the indicia; and wherein the opaque layer comprises: a mutable colorant, a molecular includant, and an ultraviolet radiation transorber adapted, upon irradiation with ultraviolet radiation, to interact with the colorant to render the colorant substantially colorless whereby the opaque layer becomes substantially transparent and the indicia is revealed.

2. The document of claim 1 wherein the molecular includant is a clathrate, a zeolite, or a cyclodextrin.

3. The document of claim 1 wherein the mutable colorant and the ultraviolet radiation transorber are associated with the molecular includant.

4. The document of claim 1 wherein the colorant is at least partially included within a cavity of the molecular includant.

5. The document of claim 4 wherein the ultraviolet radiation transorber is outside of the cavity.

6. The document of claim 1 wherein the ultraviolet radiation transorber comprises, in combination, a wavelength-selective sensitizer and a photoreactor.

7. The document of claim 6 wherein the wavelength-selective sensitizer is covalently coupled to the photoreactor.

8. The document of claim 1 wherein the mutable colorant is stable to natural light and artificial light.

9. The document of claim 1 wherein the document is a gaming ticket for a player and the message indicates the status of the player.

10. A method of overprinting, comprising:

providing a substrate having a surface with indicia thereon; and applying an opaque layer on the surface, the opaque layer comprising a mutable colorant, a molecular includant, and an ultraviolet radiation transorber adapted, upon irradiation with ultraviolet radiation, to interact with the colorant to render the colorant substantially colorless whereby the opaque layer becomes substantially transparent and the indicia is revealed.

11. The method of claim 10 wherein the molecular includant is a clathrate, a zeolite, or a cyclodextrin.

12. The method of claim 10 wherein the mutable colorant and the ultraviolet radiation transorber are associated with the molecular includant.

13. The method of claim 10 wherein the colorant is at least partially included within a cavity of the molecular includant.

14. The method of claim 13 wherein the ultraviolet radiation transorber is outside of the cavity.

15. The method of claim 10 wherein the ultraviolet radiation transorber comprises, in combination, a wavelength-selective sensitizer and a photoreactor.

16. The method of claim 15 wherein the wavelength-selective sensitizer is covalently coupled to the photoreactor.

17. The method of claim 10 wherein the mutable colorant is stable to natural light and artificial light.

18. A method of erasing overprinting, comprising:

providing a substrate having a surface with indicia thereon, wherein the surface is covered by an overprinting layer such that the indicia are not visible, the overprinting layer comprising a mutable colorant, a molecular includant, and an ultraviolet radiation transorber adapted, upon irradiation with ultraviolet radiation, to interact with the colorant to render the colorant substantially colorless whereby the overprinting layer becomes substantially transparent; and irradiating the overprinting layer such that the layer becomes substantially transparent and the underlying indicia is visible.

19. A document comprising:

a substrate having a surface;

indicia on the surface; and an opaque layer covering the indicia; wherein the opaque layer comprises a mutable colorant, a molecular includant and an ultraviolet radiation transorber adapted, upon irradiation with ultraviolet radiation, to interact with the colorant to render the colorant substantially colorless whereby the opaque layer becomes substantially transparent and the indicia is revealed, and wherein the ultraviolet radiation transorber is covalently coupled to the molecular includant.

20. A method of overprinting, comprising:

providing a substrate having a surface with indicia thereon; and applying an opaque layer on the surface, the opaque layer comprising a mutable colorant, a molecular includant, and an ultraviolet radiation transorber adapted, upon irradiation with ultraviolet radiation, to interact with the colorant to render the colorant substantially colorless whereby the opaque layer becomes substantially transparent and the indicia is revealed, and wherein the ultraviolet radiation transorber is covalently coupled to the molecular includant.

* * * * *